United States Patent
Shiloh (12)

(10) Patent No.: US 6,200,749 B1
(45) Date of Patent: *Mar. 13, 2001

(54) MUTATED FORMS OF THE ATAXIA-TELANGIECTASIA GENE AND METHOD TO SCREEN FOR A PARTIAL A-T PHENOTYPE

(75) Inventor: Yosef Shiloh, Tel Aviv (IL)

(73) Assignee: Ramot-University Authority for Applied Research and Industrial Development Ltd., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 08/642,274

(22) Filed: May 3, 1996

Related U.S. Application Data

(63) Continuation-in-part of application No. 08/629,001, filed on Apr. 8, 1996, which is a continuation-in-part of application No. 08/441,822, filed on May 16, 1995, now Pat. No. 5,756,288.

(51) Int. Cl.[7] .............................. C12Q 1/68; C07H 21/04
(52) U.S. Cl. ............................................... 435/6; 536/23.5
(58) Field of Search .......................... 435/6, 91.2, 91.21; 536/23.5

(56) References Cited

U.S. PATENT DOCUMENTS

| | | | |
|---|---|---|---|
| 3,791,932 | 2/1974 | Schuurs et al. ................ | 195/103.5 R |
| 3,839,153 | 10/1974 | Schuurs et al. ................ | 195/103.5 R |
| 3,850,578 | 11/1974 | McConnell ............................ | 424/23 |
| 3,850,752 | 11/1974 | Schuurs et al. ................ | 195/103.5 R |
| 3,853,987 | 12/1974 | Dreyer .................................. | 424/23 |
| 3,867,517 | 2/1975 | Ling ...................................... | 424/1 |
| 3,879,262 | 4/1975 | Schuurs et al. ........................ | 195/99 |
| 3,901,654 | 8/1975 | Gross .................................... | 424/23 |
| 3,935,074 | 1/1976 | Rubenstein et al. ............. | 195/103.5 |
| 3,984,533 | 10/1976 | Uzgiris .................................. | 424/23 |
| 3,996,345 | 12/1976 | Ullman et al. ........................ | 424/23 |
| 4,034,074 | 7/1977 | Miles .................................... | 424/12 |
| 4,098,876 | 7/1978 | Piasio et al. ............................ | 424/1 |
| 4,736,866 | 4/1988 | Leder et al. ............................ | 800/1 |
| 4,879,219 | 11/1989 | Wands et al. ............................ | 435/7 |
| 5,011,771 | 4/1991 | Bellet et al. ........................ | 435/7.94 |
| 5,175,383 | 12/1992 | Leder et al. ............................ | 800/2 |
| 5,175,384 | 12/1992 | Krimpenfort et al. .................. | 800/2 |
| 5,175,385 | 12/1992 | Wagner et al. .......................... | 800/2 |
| 5,221,778 | 6/1993 | Byrne et al. ............................ | 800/2 |
| 5,281,521 | 1/1994 | Trojanowski et al. ................ | 435/7.5 |
| 5,288,846 | 2/1994 | Quertermous et al. ........... | 435/172.3 |
| 5,298,422 | 3/1994 | Schwartz et al. .................. | 435/320.1 |
| 5,347,075 | 9/1994 | Sorge ...................................... | 800/2 |
| 5,360,735 | 11/1994 | Weinshank et al. ............... | 435/240.2 |
| 5,387,742 | 2/1995 | Cordell .................................. | 800/2 |
| 5,395,767 | 3/1995 | Murnane et al. .................. | 435/320.1 |
| 5,464,764 | 11/1995 | Capecchi et al. .................. | 435/172.3 |
| 5,487,992 | 1/1996 | Capecchi et al. .................. | 435/172.3 |

FOREIGN PATENT DOCUMENTS

| | | | |
|---|---|---|---|
| WO93/4200 | 7/1993 | (WO) . | |
| WO940057 | 2/1994 | (WO) | .............................. C12N/1/68 |
| WO9406908 | 3/1994 | (WO) . | |
| WO9423049 | 10/1994 | (WO) . | |
| WO9428123 | 12/1994 | (WO) . | |
| WO9503431 | 2/1995 | (WO) | ........................... C12Q/15/12 |

OTHER PUBLICATIONS

Aksentijevitch et al. "Familial mediterranean fever in Moroccan Jews: demonstration of a founder effect by extended haplotype analysis" *Am. J. Hum. Genet.*, 53:644–651 (1993).

Ambrose et al., "A physical map across chromosome 11q22–23 containing the major locus for ataxia–telangiectasia" *Genomics*, 21:612–619 (1994).

Attree et al., "The Lowe's oculocerebrorenal syndrome gene encodes a protein highly homologous to inositol . . . " *Nature*, 358:239–242 (1992).

Beamish and Lavin, "Radiosensitivity in ataxia–telangiectasia: anomalies in radiation–induced cell cycle delay" *J. Radiat. Biol.*, 65:175–184.

Berger et al., "Isolation of a candidate gene for Norrie disease by positional cloning" *Nature Genet.* 1:199–203 (1992).

Buckler et al., "Exon amplification: a strategy to isolate mammalian genes used on RNA splicing" *Proc. Natl. Acad. Sci. USA*, 88:4005–4009 (1991).

Chakravarti et al., "Nonuniform recombination within the human beta–globin gene cluster" *Am. J. Hum. Genet.*, 36:1239–1258 (1984).

Chelly et al., "Isolation of a candidate gene for Menkes disease that encodes a potential heavy metal binding protein" *Nature Genet.*, 3:14–19 (1993).

Church et al., "Isolation of genes from complex sources of mammalian genomic DNA using exon amplification" *Nature Genet.*, 6:98–104 (1993).

Collins, "Positional cloning: let's not call it reverse anymore" *Nature Genet.*, 1:3–6 (1992).

Duyk et al., "Exon trapping: a genetic screen to identify candidate transcribed sequences in cloned mammalian genomic DNA" *Proc. Natl. Acad. Sci. USA*, 87:8995–8999 (1990).

Foroud et al., "Localization of the AT locus to an 8 cM interval defined by STMY and S132" *Am. J. Hum. Genet.*, 49:1263–1279 (1991).

Frohman, *PCR Methods and Applications*, 4:S40–S58 (1994).

(List continued on next page.)

Primary Examiner—Lisa B. Arthur
(74) Attorney, Agent, or Firm—Kohn & Associates

(57) ABSTRACT

A purified and isolated gene, designated ATM, is described mutations of which cause ataxia-telangiectasia and its genomic organization.

5 Claims, 2 Drawing Sheets

OTHER PUBLICATIONS

Frohman et al., *Proc. Natl. Sci. USA*, 85:8998–9002 (1988).

Gatti et al., "Genetic haplotyping of ataxia–telangiectasia families localizes the major gene to an 850 kb region on chromosome . . . " *Int. J. Radiat. Biol.*, (in press) (1994).

Gatti et al., "Localization of an ataxia–telangiectasia gene to chromosome 11q22–23" *Nature*, 336:577–580 (1988).

Hastbacka et al., "Linkage disequilibrium mapping in isolated founder populations: diastrophic dysplasia in Finland" *Nature Genet.*, 2:204–211 (1992).

Heim et al., "Heterozygous manifestations in four autosomal recessive human cancer–prone syndromes . . . " *Mutat. Res.*, 284:25–36 (1992).

Kastan et al., "A mammalian cell cycle checkpoint pathway utilizing p53 and GADD45 is defective in ataxia–telangiectasia" *Cell*, 71:587–597.

Kerem et al., "Identification of the cystic fibrosis gene: genetic analysis" *Science*, 245:1073–1080 (1989).

Khanna and Lavin, "Ionizing radiation and UV induction of p53 protein by different pathways in ataxia–telangiectasia cells" *Oncogene*, 8:3307–3312 (1993).

Lange et al., "Localization of an ataxia–telangiectasia gene to a 850 kb interval on chromosome 11q23.1 by linkage . . . " (submitted) (1994).

Lehesjoki et al., Localization of the EPM1 gene for progressive myoclonus epilepsy on chromosome 21: linkage disequilibrium . . . *Hum. Mol. Genet.*, 2:1229–1234 (1993).

Litt and Luty, "A hypervariable microsatellite revealed by in vitro amplification of a dinucleotide repeat within the cardiac muscle . . . " *Am. J. Hum. Genet.*, 44:397–401 (1989).

Llerena et al., "Spontaneous and induced chromosome breakage in chorionic villus samples . . . " *J. Med. Genet.*, 26:174–178 (1989).

McConville et al., "Genetic and physical mapping of the ataxia–telangiectasia locus on chromosome 11q22–23" *Int. J. Radiat. Biol.* (1994).

McConville et al., *Hum. Mol. Genet.*, 2:969–974 (1993).

McConville et al., *Nucleic Acids, Res.*, 18:4335–4343 (1990).

Miki et al., "A strong candidate for the breast and ovarian cancer susceptibility gene BRCA1" *Science*, 266:66–71 (1994).

Mitchison et al., "Fine genetic mapping of the Batten Disease locus (CLN3) by haplotype analysis and demonstration . . . " *Genomics*, 16:455–460 (1993).

Morgan et al., "The selective isolation of novel cDNAs encoded by the regions surrounding the human interleukin 4 and 5 genes" *Nucleic Acids Res.*, 20:5173–5179 (1992).

Oskato et al., "Ataxia–telangiectasia: allelic association with 11q22–23 markers in Moroccan–Jewish patients" *43rd Annual Meeting of the American Society of Human Genetics*, New Orleans, LA (1993).

Ozelius et al., "Strong allelic association between the torsion dystonia gene (DYT1) and loci on chromosome . . . " *Am. J. Hum. Genet.*, 50:619–628 (1992).

Parimoo et al., "cDNA selection: efficient PCR approach for the selection of cDNAs encoded in large chromosomal DNA fragments" *Proc. Natl. Acad. Sci. USA*, 88:9623–9627 (1991).

Rotman et al., "Rapid identification of polymorphic CA–repeats in YAC clones" *Molecular Biotechnology* (in press) (1994a).

Rotman et al., "Three dinucleotide repeat polymorphisms at the ataxia–telangiectasia locus" *Human Molecular Genetics* (in press) (1994b).

Rotman et al., "A YAC contig spanning the ataxia–telangiectasia locus (groups A and C) on chromosome 11q22–23" *Genomics* (in press) (1994c).

Rotman et al. "Physical and genetic mapping of the ATA/ATC locus in chromosome 11q22–23" *Int. J. Radiat. Biol.* (in press) (1994d).

Savitsky et al., "A single gene with homologies to phosphatidylinositol 3–kinases and rad3+ is mutated in all . . . " (submitted for publication).

Sirugo et al., "Friedreich ataxia in Louisiana Acadians: demonstration of a founder effect by analysis . . . " *Am. J. Hum. Genet.*, 50:559–566 (1992).

Shiloh, "Ataxia–telangiectasia: closer to unraveling the mystery" *European Journal of Human Genetics* (in press).

Shiloh et al., "Carrier detection in ataxia–telangiectasia" *The Lancet*, I:689 (1986).

Swift et al., "Cancer predisposition of ataxia–telangiectasia heterozygotes" *Cancer Genet. Cytogenet.*, 46:21–27 (1990).

Swift et al., "Incidence of cancer in 1616 families affected by ataxia–telangiectasia" *New Engl. J. Med.*, 325:1831–1836 (1991).

Tagle et al., "Magnetic bead capture of expressed sequences encoded within large genomic segments" *Nature*, 361:751–753 (1993).

The European Polycystic Kidney Disease Consortium, "The polycystic kidney disease 1 gene encodes a 14 kb transcript . . . " *Cell*, 77:881–894 (1994).

The Huntington's Disease Collaborative Research Group, "A novel gene containing a trinucleotide repeat that is expanded . . . " *Cell*, 72:971–983 (1993).

Trofatter et al., "A novel moesin–, ezrin–, radixin–like gene is a candidate for the neurofibromatosis 2 tumor suppressor" *Cell*, 72:791–800 (1993).

Vanagaite et al., "Physical localization of microsatellite markers at the ataxia–telangiectasia locus at 11q22–23" *Genomics*, 22:231–233 (1994a).

Vanagaite et al., "A high–density microsatellite map of the ataxia–telangiectasia locus" *Human Genetics* (in press) (1994b).

Vetrie et al., "The gene involved in X–linked agammaglobulinemia is a member of the src family of protein–tyrosine kinases" *Nature*, 361:226–233 (1993).

Weber and May, "Abundant class of human DNA polymorphisms which can be typed using the polymerase chain reaction" *Am. J. Hum. Genet.*, 44:388–396 (1989).

Ziv et al., "Ataxia–telangiectasia: linkage analysis in highly inbred Arab and Druze families and differentiation . . . " *Hum. Genet.*, 88:619–626 (1992).

Ziv et al., "The ATC (ataxia–telangiectasia complementation group C) locus localizes to 11q22–q23" *Genomics*, 9:373–375 (1991).

Kapp, "Cloning of a candidate gene for Ataxia–Telangiectasia Group D" *Am. J. Hum. Genet.*, 51:45–54 (1992).

Leonardt et al., "Nucleotide sequence analysis of a candidate gene for Ataxia–Telangiectasia Group D (ATDC)" *Genomics*, 19:130–136 (1994).

Burke adn Olson, "Preparation of clone libraries . . . " in *Methods in Enzymology*, vol. 194, "Guide to Yeast Genetics and Molecular Biology" eds. Guthrie and Fink, Academic Press, Chapt. 17, pp. 251–270 (1991).

Byrne et al., "Ataxia–without–telangiectasia" *J. Neurol. Sci.*, 66:307–317 (1984).

Gilboa et al., "Transfer and expression of cloned genes using retroviral vectors" *BioTechniques*, 4(6):504–512 (1986).

Kawasaki, ES. "Amplification of RNA" in *PCR Protocols: A Guide to Methods and Applications* Innis, MA, Gelfand, DH, Sninsky, JJ, White, TJ eds. Academic Press, pp. 21–27 (1990).

Shiloh et al., "Genetic, physical and functional analysis of the ataxia–telangiectasia locus . . . " Slide Session 48: 261. *Am. J. Hum. Genet.*, 55 (suppl.), A49 (1994a).

Shiloh et al., "Genetic physical and functional analysis of the ataxia–telangiectasia locus . . . " 44th Annual meeting of the American Soc. of Human Genetics, Montreal, *Am. J. Hum. Genet.*, 55:A49 (1994b).

Rasio et al., (1995) "Genomic organization of the ATM locus involved in Ataxia–Telangiectasia" *Cancer Research*, 55:6053–6057.

McConville et al. Am J. Hum. Genet. (1996) 59:320–330.

Telater et al. (1996) Am. J. Hum Genet. (1996) 59:40–44.

Lakin et al. (1996) Oncogene 13:2707–2716.

Aicardi et al., "Ataxia–ocularmotor apraxia: A syndrome mimicking ataxia–telangiectasia" *Ann. Neurol.*, 24:497–502 (1988).

Ambrose et al., "Structure and expression of the Huntington's disease gene: evidence against simple inactivation . . . " *Som. Cell. Mol. Genet.*, 20:27–38 (1994b).

Anderson and Kunkel, "The molecular and biochemical basis of Duchenne muscular dystrophy" *Trends Biochem. Sci.*, 17:289–292 (1992).

Ballabio et al., "Molecular heterogeneity of steroid sulfatase deficiency: a multicenter study on 57 unrelated patients . . . " *Genomics*, 4:36–40 (1989).

Barker, "A more robust, rapid alkaline denaturation sequencing method" *BioTechniques*, 14:168–169 (1993).

Barnes, "PCR amplification of up to 35–kb DNA with high fidelity and high yield from lambda bacteriophage templates" *Proc.Natl.Acad.Sci.*, 91:2216–2220 (1994).

Beaudet and Tsui, "A suggested nomeclature for designating mutations" *Hum. Mutat.*, 2:245–248 (1993).

Broughton et al., "Mutations in the xeroderma pigmentosum group D DAN repair/transcription gene in patients . . . " *Nature Genet.*, 7:189–194 (1994).

Broughton et al., "Molecular and cellular analysis of the DNA repair defect in a patient in xeroderma pigmentosum . . . " *Am. J. Hum. Genet.*, 56:167–174 (1995).

Brown et al., "Control of p70 S6 kinase by kinase activity of FRAP in vivo" *Nature*, 377:441–446 (1995).

Capecchi, "Altering the genome by homologous recombination" *Science*, 244:1288–1292 (1989).

Cheng et al., "Effective amplification of long targets from cloned inserts and human genomic DNA" *Proc.Natl.Acad. Sci.*, 91:5695–5699 (1994).

Chessa et al., "Heterogeneity in ataxia–telangiectasia: classical phenotype associated with intermediate cellular . . . " *Am. J. Med. Genet.*, 42:741–746 (1992).

Chillon et al., "Mutations in the cystic fibrosis gene in patients with gongenital absence of the vas deferens" *New Engl. J. Med.*, 332–1475–1480 (1995).

Church et al., "Isolation of genes from complex sources of mammalian genomic DNA using exon amplification" *Nature Genet.*, 6:98 (1994).

Cooper and Krawczak, in *Human Gene Mutation*, BIOS Scientific Publishers, London (1993), Chapters 8 and 10.

Davies et al., "Targeted alterations in yeast artificial chromosomes for inter–species gene transfer" *Nucleic Acids Research*, 20:2693–2698 (1992).

Derry et al., "WASP gene mutations in Wiskott–Aldrich syndrome and X–linked thrombocytopenia" *Hum. Mol. Genet.*, 4:1127–1135 (1995).

Dickinson et al., "High frequency gene targeting using insertional vectors" *Hum. Mol. Genet.*, 2:1299–1302 (1993).

Dietz and Kendzior, "Maintenance of an open reading frame as an additional level of scrutiny during spice site selection" *Nature Genet.*, 8:183–188 (1994).

Fiorilli et al., "Variant of ataxia–telangiectasia with low–level radiosensitivity" *Hum. Genet.*, 70:274–277 (1985).

Fodor et al., "Multiplexed biochemical assays with biological chips" *Nature*, 364:555–556 (1993).

Foord and Rose, "Long–distance PCR" *PCR Methods Appl.*, 3:S149–S161 (1994).

Friedman and Weitberg, "Ataxia–without telangiectasia" *Movement Disorders*, 8:223–226 (1993).

Gatti et al., "Genetic haplotyping of ataxia–telangiectasia families localizes the major gene to an 850 kb region . . . " Int. J. Radiat. Biol., (1994).

Gibson et al., "A nonsense mutation and exon skipping in the Fanconi anaemia group C gene" *Hum. Mol. Genet.*, 2:797–799 (1993).

Gottlieb and Jackson, "Protein kinases and DNA damage" *Trends Biochem. Sci.*, 19:500–503 (1994).

Greenwell et al., "TEL1, a gene involved in controlling telomere length in *Saccaromyces cerevisiae*, is homologous . . . " *Cell*, 82:823–829 (1995).

Harding, "Clinical features and classification of inherited ataxias" *Adv. Neurol.*, 61:1–14 (1993).

Harnden, "The nature of ataxia–telangiectasia: problems and perspectives" *Int. J. Radiat. Biol.*, 66:S13–S19 (1994).

Hogervorst et al., "Rapid detection of BRCA1 mutations by the protein truncation test" Nature Genetics, 10:208–212 (1995).

Huxley et al., "The human HPRT gene on a yeast artificial chromosome is functional when transferred to mouse cells" *Genomics*, 9:742–750 (1991).

Jackson, "A reappraisal of non–consensus mRNA splice sites" *Nucleic Acids Res.*, 19:3795–3798 (1991).

Jakobivits et al., "Germ–line transmission and expression of a human–derived yeast artificial chromosome" *Nature*, 362:255–261 (1993).

James et al., "A radiation hybrid map of 506 STS markers spanning human chromosome 11" *Nature Genet.*, 8:70 (1994).

Jarvi et al., "Cystic fibrosis transmembrane conductance regulator and obstructive azoospermia" *The Lancet*, 345:1578 (1995).

Jasper et al., "Genetic complementation analysis of ataxia telangiectasia and Nijmegen breakage syndrome . . . " *Cytogenet. Cell. Genet.*, 49:259 (1988).

Kolluri et al., "Identification of WASP mutations in patients with Wiskott–Aldrich syndrome and isolated thrombocytopenia . . . " *Hum. Mol. Genet.*, 4:1119–1126 (1995).

Lamb et al., "Introduction and expression of the 400 kilobase precursor amyloid protein gene in transgenic mice" *Nature Genetics*, 5:22–29 (1993).

Lange et al., "Localization of an ataxia–telangiectasia gene to a 850 kb interval on chromosome . . . " *Am. J. Hum. Genet.*, S7:112–119 (1995).

Lichter et al., "High–resolution mapping of human chromosome 11 by in situ hybridization with cosmid clones" *Science*, 247:64–69 (1990).

Liu and Sommer, "Restriction endonuclease fingerprinting (REF): a sensitive method for screening mutations . . . " *BioTechniques*, 18:470–477 (1995).

Lovett et al., "Direct selection: a method for the isolation of CDNAs encoded by large genomic regions" *Proc.Natl.Acad.Sci.USA*, 88:9628 (1991).

Maserati et al., "Ataxia–without–telangiectasia in two sisters with rearrangements of chromosome 7 and 14" *Clin. Genet.*, 34:283–287 (1988).

McConville et al., "Genetic and physical mapping of the ataxia–telangiectasia locus on chromosome 11q22–23" *Int. J. Radiat. Biol.* vol. 66, No. 6, S45–S56 (1994).

Nehls et al. "Exon amplification from complete libraries of genomic DNA using a novel phage vector . . . " *Oncogene*, 9:2169–2175 (1994a).

Nehls et al., "The sequence complexity of exons trapped from the mouse genome" *Current Biology*, 4:983–989 (1994b).

Orita et al., "Detection of polymorphisms of human DNA by gel electrophoresis as single–strand conformation polymorphisms" *Proc.Natl.Acad.Sci.USA*, 86:2766–2770 (1989).

Pease et al., "Light–generated oligonucleotide arrays for rapid DNA sequence analysis" *Proc.Natl.Acad.Sci.USA*, 91(11):5022–5026 (1994).

Richard et al., "A radiation hybrid map of human chromosome 11q22–q23 containing the ataxia telangiectasia disease locus" *Genomics*, 17:1 (1993).

Roberts et al., "Exon structure of the human dystrophin gene" *Genomics*, 16:536–538 (1993).

Rothstein, "Targeting, disruption, replacement, and allele rescue . . . " in *Methods in Enzymology*, vol. 194, eds. C. Guthrie and G. Fink, Academic Press, Inc., Chap. 19, pp. 281–301 (1991).

Rotman et al., "Three dinucleotide repeat polymorphisms at the ataxia–telangiectasia locus" *Hum. Mol. Genet.*, vol. 3, No. 11, 2079 (1994b).

Rotman et al., "A YAC contig spanning the ataxia–telangiectasia locus (groups A and C) on chromosome 11q22–23" *Genomics*, 24:234–242 (1994c).

Rotman et al., "Physical and genetic mapping of the ATA/ATC locus in chromosome 11q22–23" *Int. J. Radiat. Biol.*, (1994d).

Rotman et al., "Rapid identification of polymorphic CA–repeats in YAC clones" *Molecular Biotechnology*, (1995). [n/a—will send].

Savitsky et al., "A single gene with homologies to phosphatidyl–inositol 3–kinases and rad3+ . . . " *Science*, 268:1749–1753 (Jun. 23, 1995a).

Savitsky et al., "The complete sequence of the coding region of the ATM gene reveals similarity to cell cycle . . . " *Hum. Mol. Genet.*, 4:2025–2032 (1995b).

Schedl et al., "A yeast artificial chromosome covering the tyrosinase gene confers copy number–dependent . . . " *Nature*, 362:258–261 (1993).

Sommer, "Recent human germ–line mutations: inferences from patients with hemophilia B" *Trends Gene*, 11:141–147 (1995).

Steingrimsdottir et al., "Mutations which alter splicing in the human hypoxanthine–guanine phosphoribosyl–transferase . . . " *Nucleic Acids Res.*, 6:1201–1208 (1992).

Strauss et al., "Germ line transmission of a yeast artificial chromosome spanning the murine . . . " *Science*, 259:1904–1907 (1993).

Taylor et al., "Genetic and cellular features of ataxia telangiectasia" *Int. J. Radiat. Biol.*, 65:65–70 (1994).

Taylor et al., "Variant forms of ataxia telangiectasia" *J. Med. Genet.*, 24:669–677 (1987).

Weemaes et al., "Nijegan breakage syndrome: a progress report" *Int. J. Radiat. Biol.*, 66:S185–S188 (1994).

Ying and Decoteau, "Cytogenetic anomalies in a patient with ataxia, immune deficiency, and hihg alpha–fetoprotein . . . " *Cancer Genet. Cytogenet.*, 4:311–317 (1983).

Zakian, "ATM–related genes: what do they tell us about functions of the human gene?" *Cell*, 82:685–687 (1995).

Ziv et al., "Ataxia–telangietasia: a variant with altered in vitro phenotype of fibroblast cells" *Mutation Res.*, 210:211–219 (1989).

McConville et al. Am. J. Hum. Genet. (1996) 59:320–330.*

Telatar et al. (1996) Am. J. Hum. Genet. (1996) 59:40–44.*

Lakin et al. (1996) Oncongene 13:2707–2716.*

Vopechovsky et al. Can. Res. 56:2726–2732 (1996).*

* cited by examiner

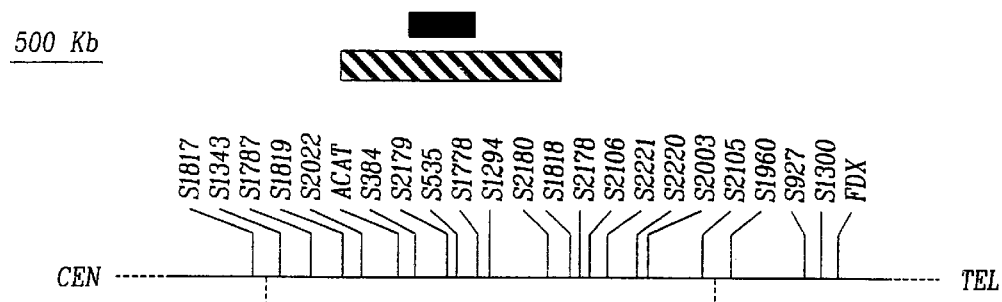
*Fig-1A*
*Fig-1B*
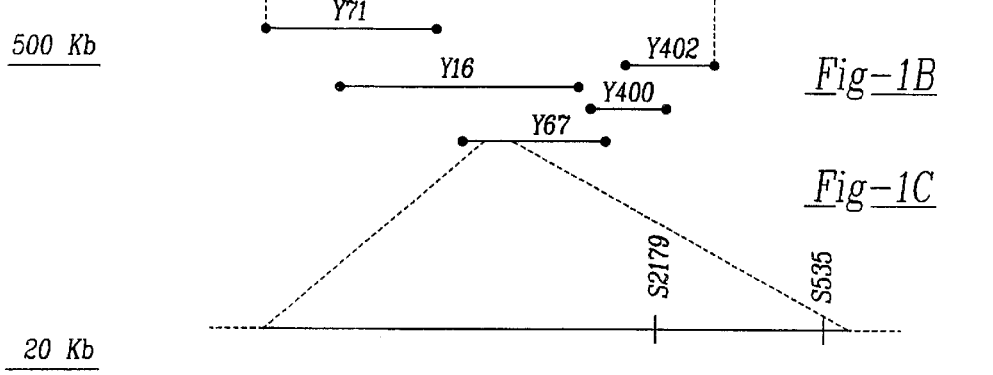
*Fig-1C*
*Fig-1D*
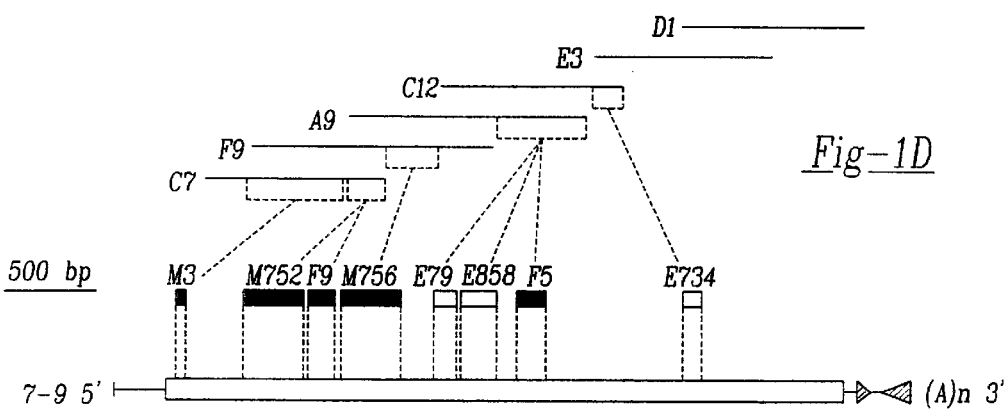
*Fig-1E*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 5912 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (B) CLONE: 7-9

(xi) SEQUENCE DESCRIPTION: SEQ ID NO:1:

```
CATACTTTTT CCTCTTAGTC TACAGGTTGG CTGCATAGAA GAAAAAGGTA GAGTTATTTA      60

TAATCTTGTA AATCTTGGAC TTTGAGTCAT CTATTTTCTT TTACAGTCAT CGAATACTTT     120

TGGAAATAAG GTAATATATG CCTTTTGAGC TGTCTTGACG TTCACAGATA TAAAATATTA     180

AATATATTTT AATTTTGTGC CCTTGCAGAT TGATCACTTA TTCATTAGTA ATTTACCAGA     240

GATTGTGGTG GAGTTATTGA TGACGTTACA TGAGCCAGCA AATTCTAGTG CCAGTCAGAG     300

CACTGACCTC TGTGACTTTT CAGGGGATTT GGATCCTGCT CCTAATCCAC CTCATTTTCC     360

ATCGCATGTG ATTAAAGCAA CATTTGCCTA TATCAGCAAT TGTCATAAAA CCAAGTTAAA     420

AAGCATTTTA GAAATTCTTT CCAAAAGCCC TGATTCCTAT CAGAAAATTC TTCTTGCCAT     480

ATGTGAGCAA GCAGCTGAAA CAAATAATGT TTATAAGAAG CACAGAATTC TTAAAATATA     540

TCACCTGTTT GTTAGTTTAT TACTGAAAGA TATAAAAAGT GGCTTAGGAG GAGCTTGGGC     600

CTTTGTTCTT CGAGACGTTA TTTATACTTT GATTCACTAT ATCAACCAAA GGCCTTCTTG     660

TATCATGGAT GTGTCATTAC GTAGCTTCTC CCTTTGTTGT GACTTATTAA GTCAGGTTTG     720

CCAGACAGCC GTGACTTACT GTAAGGATGC TCTAGAAAAC CATCTTCATG TTATTGTTGG     780

TACACTTATA CCCCTTGTGT ATGAGCAGGT GGAGGTTCAG AAACAGGTAT GGACTTGTT     840

GAAATACTTA GTGATAGATA ACAAGGATAA TGAAAACCTC TATATCACGA TTAAGCTTTT     900

AGATCCTTTT CCTGACCATG TTGTTTTTAA GGATTTGCGT ATTACTCAGC AAAAAATCAA     960

ATACAGTAGA GGACCCTTTT CACTCTTGGA GGAAATTAAC CATTTTCTCT CAGTAAGTGT    1020

TTATGATGCA CTTCCATTGA CAAGACTTGA AGGACTAAAG GATCTTCGAA GACAACTGGA    1080

ACTACATAAA GATCAGATGG TGGACATTAT GAGAGCTTCT CAGGATAATC CGCAAGATGG    1140

GATTATGGTG AAACTAGTTG TCAATTTGTT GCAGTTATCC AAGATGGCAA TAAACCACAC    1200

TGGTGAAAAA GAAGTTCTAG AGGCTGTTGG AAGCTGCTTG GGAGAAGTGG GTCCTATAGA    1260

TTTCTCTACC ATAGCTATAC AACATAGTAA AGATGCATCT TATACCAAGG CCCTTAAGTT    1320

ATTTGAAGAT AAAGAACTTC AGTGGACCTT CATAATGCTG ACCTACCTGA ATAACACACT    1380

GGTAGAAGAT TGTGTCAAAG TTCGATCAGC AGCTGTTACC TGTTTGAAAA ACATTTTAGC    1440

CACAAAGACT GGACATAGTT TCTGGGAGAT TTATAAGATG ACAACAGATC CAATGCTGGC    1500

CTATCTACAG CCTTTTAGAA CATCAAGAAA AAAGTTTTTA GAAGTACCCA GATTTGACAA    1560

AGAAAACCCT TTTGAAGGCC TGGATGATAT AAATCTGTGG ATTCCTCTAA GTGAAAATCA    1620

TGACATTTGG ATAAAGACAC TGACTTGTGC TTTTTTGGAC AGTGGAGGCA CAAAATGTGA    1680
```

```
AATTCTTCAA TTATTAAAGC CAATGTGTGA AGTGAAAACT GACTTTTGTC AGACTGTACT       1740

TCCATACTTG ATTCATGATA TTTTACTCCA AGATACAAAT GAATCATGGA GAAATCTGCT       1800

TTCTACACAT GTTCAGGGAT TTTTCACCAG CTGTCTTCGA CACTTCTCGC AAACGAGCCG       1860

ATCCACAACC CCTGCAAACT TGGATTCAGA GTCAGAGCAC TTTTTCCGAT GCTGTTTGGA       1920

TAAAAAATCA CAAAGAACAA TGCTTGCTGT TGTGGACTAC ATGAGAAGAC AAAAGAGACC       1980

TTCTTCAGGA ACAATTTTTA ATGATGCTTT CTGGCTGGAT TTAAATTATC TAGAAGTTGC       2040

CAAGGTAGCT CAGTCTTGTG CTGCTCACTT TACAGCTTTA CTCTATGCAG AAATCTATGC       2100

AGATAAGAAA AGTATGGATG ATCAAGAGAA AGAAGTCTT GCATTTGAAG AAGGAAGCCA       2160

GAGTACAACT ATTTCTAGCT TGAGTGAAAA AAGTAAAGAA GAAACTGGAA TAAGTTTACA       2220

GGATCTTCTC TTAGAAATCT ACAGAAGTAT AGGGGAGCCA GATAGTTTGT ATGGCTGTGG       2280

TGGAGGGAAG ATGTTACAAC CCATTACTAG ACTACGAACA TATGAACACG AAGCAATGTG       2340

GGGCAAAGCC CTAGTAACAT ATGACCTCGA ACAGCAATC CCCTCATCAA CACGCCAGGC       2400

AGGAATCATT CAGGCCTTGC AGAATTTGGG ACTCTGCCAT ATTCTTTCCG TCTATTTAAA       2460

AGGATTGGAT TATGAAAATA AAGACTGGTG TCCTGAACTA AAGAACTTC ATTACCAAGC       2520

AGCATGGAGG AATATGCAGT GGGACCATTG CACTTCCGTC AGCAAAGAAG TAGAAGGAAC       2580

CAGTTACCAT GAATCATTGT ACAATGCTCT ACAATCTCTA AGAGACAGAG AATTCTCTAC       2640

ATTTTATGAA AGTCTCAAAT ATGCCAGAGT AAAAGAAGTG GAAGAGATGT GTAAGCGCAG       2700

CCTTGAGTCT GTGTATTCGC TCTATCCCAC ACTTAGCAGG TTGCAGGCCA TTGGAGAGCT       2760

GGAAAGCATT GGGGAGCTTT TCTCAAGATC AGTCACACAT AGACAACTCT CTGAAGTATA       2820

TATTAAGTGG CAGAAACACT CCCAGCTTCT CAAGGACAGT GATTTTAGTT TTCAGGAGCC       2880

TATCATGGCT CTACGCACAG TCATTTTGGA GATCCTGATG GAAAAGGAAA TGGACAACTC       2940

ACAAAGAGAA TGTATTAAGG ACATTCTCAC CAAACACCTT GTAGAACTCT CTATACTGGC       3000

CAGAACTTTC AAGAACACTC AGCTCCCTGA AAGGGCAATA TTTCAAATTA AACAGTACAA       3060

TTCAGTTAGC TGTGGAGTCT CTGAGTGGCA GCTGGAAGAA GCACAAGTAT TCTGGGCAAA       3120

AAAGGAGCAG AGTCTTGCCC TGAGTATTCT CAAGCAAATG ATCAAGAAGT GGATGCCAG       3180

CTGTGCAGCG AACAATCCCA GCCTAAAACT TACATACACA GAATGTCTGA GGGTTTGTGG       3240

CAACTGGTTA GCAGAAACGT GCTTAGAAAA TCCTGCGGTC ATCATGCAGA CCTATCTAGA       3300

AAAGGCAGTA GAAGTTGCTG GAAATTATGA TGGAGAAAGT AGTGATGAGC TAAGAAATGG       3360

AAAAATGAAG GCATTTCTCT CATTAGCCCG GTTTTCAGAT ACTCAATACC AAAGAATTGA       3420

AAACTACATG AAATCATCGG AATTTGAAAA CAAGCAAGCT CTCCTGAAAA GAGCCAAAGA       3480

GGAAGTAGGT CTCCTTAGGG AACATAAAAT TCAGACAAAC AGATACACAG TAAAGGTTCA       3540

GCGAGAGCTG GAGTTGGATG AATTAGCCCT GCGTGCACTG AAAGAGGATC GTAAACGCTT       3600

CTTATGTAAA GCAGTTGAAA ATTATATCAA CTGCTTATTA AGTGGAGAAG AACATGATAT       3660

GTGGGTATTC CGACTTTGTT CCCTCTGGCT TGAAAATTCT GGAGTTTCTG AAGTCAATGG       3720

CATGATGAAG AGAGACGGAA TGAAGATTCC AACATATAAA TTTTTGCCTC TTATGTACCA       3780

ATTGGCTGCT AGAATGGGGA CCAAGATGAT GGGAGGCCTA GGATTTCATG AAGTCCTCAA       3840

TAATCTAATC TCTAGAATTT CAATGGATCA CCCCCATCAC ACTTTGTTTA TTATACTGGC       3900

CTTAGCAAAT GCAAACAGAG ATGAATTTCT GACTAAACCA GAGGTAGCCA GAAGAAGCAG       3960

AATAACTAAA AATGTGCCTA ACAAAGCTC TCAGCTTGAT GAGGATCGAA CAGAGGCTGC       4020

AAATAGAATA ATATGTACTA TCAGAAGTAG GAGACCTCAG ATGGTCAGAA GTGTTGAGGC       4080
```

```
ACTTTGTGAT GCTTATATTA TATTAGCAAA CTTAGATGCC ACTCAGTGGA AGACTCAGAG     4140

AAAAGGCATA AATATTCCAG CAGACCAGCC AATTACTAAA CTTAAGAATT TAGAAGATGT     4200

TGTTGTCCCT ACTATGGAAA TTAAGGTGGA CCACACAGGA GAATATGGAA ATCTGGTGAC     4260

TATACAGTCA TTTAAAGCAG AATTTCGCTT AGCAGGAGGT GTAAATTTAC CAAAAATAAT     4320

AGATTGTGTA GGTTCCGATG GCAAGGAGAG GAGACAGCTT GTTAAGGGCC GTGATGACCT     4380

GAGACAAGAT GCTGTCATGC AACAGGTCTT CCAGATGTGT AATACATTAC TGCAGAGAAA     4440

CACGGAAACT AGGAAGAGGA AATTAACTAT CTGTACTTAT AAGGTGGTTC CCCTCTCTCA     4500

GCGAAGTGGT GTTCTTGAAT GGTGCACAGG AACTGTCCCC ATTGGTGAAT TTCTTGTTAA     4560

CAATGAAGAT GGTGCTCATA AAAGATACAG GCCAAATGAT TTCAGTGCCT TTCAGTGCCA     4620

AAAGAAAATG ATGGAGGTGC AAAAAAGTC TTTTGAAGAG AAATATGAAG TCTTCATGGA      4680

TGTTTGCCAA AATTTTCAAC CAGTTTTCCG TTACTTCTGC ATGGAAAAAT TCTTGGATCC     4740

AGCTATTTGG TTTGAGAAGC GATTGGCTTA TACGCGCAGT GTAGCTACTT CTTCTATTGT     4800

TGGTTACATA CTTGGACTTG GTGATAGACA TGTACAGAAT ATCTTGATAA ATGAGCAGTC     4860

AGCAGAACTT GTACATATAG ATCTAGGTGT TGCTTTTGAA CAGGGCAAAA TCCTTCCTAC     4920

TCCTGAGACA GTTCCTTTTA GACTCACCAG AGATATTGTG GATGGCATGG GCATTACGGG     4980

TGTTGAAGGT GTCTTCAGAA GATGCTGTGA GAAAACCATG GAAGTGATGA GAAACTCTCA     5040

GGAAACTCTG TTAACCATTG TAGAGGTCCT TCTATATGAT CCACTCTTTG ACTGGACCAT     5100

GAATCCTTTG AAAGCTTTGT ATTTACAGCA GAGGCCGGAA GATGAAACTG AGCTTCACCC     5160

TACTCTGAAT GCAGATGACC AAGAATGCAA ACGAAATCTC AGTGATATTG ACCAGAGTTT     5220

CGACAAAGTA GCTGAACGTG TCTTAATGAG ACTACAAGAG AAACTGAAAG GAGTGGAAGA     5280

AGGCACTGTG CTCAGTGTTG GTGGACAGGT GAATTTGCTC ATACAGCAGG CCATAGACCC     5340

CAAAAATCTC AGCCGACTTT TCCCAGGATG GAAAGCTTGG GTGTGATCTT CAGTATATGA     5400

ATTACCCTTT CATTCAGCCT TTAGAAATTA TATTTTAGCC TTTATTTTTA ACCTGCCAAC     5460

ATACTTTAAG TAGGGATTAA TATTTAAGTG AACTATTGTG GGTTTTTTTG AATGTTGGTT     5520

TTAATACTTG ATTTAATCAC CACTCAAAAA TGTTTTGATG GTCTTAAGGA ACATCTCTGC     5580

TTTCACTCTT TAGAAATAAT GGTCATTCGG GCTGGGCGCA GCGGCTCACG CCTGTAATCC     5640

CAGCACTTTG GGAGGCCGAG GTGAGCGGAT CACAAGGTCA GGAGTTCGAG ACCAGCCTGG     5700

CCAAGAGACC AGCCTGGCCA GTATGGTGAA ACCCTGTCTC TACTAAAAAT ACAAAAATTA     5760

GCCGAGCATG GTGGCGGGCA CCTGTAGTCC CAGCTACTCG AGAGGCTGAG GCAGGAGAAT     5820

CTCTTGAACC TGGGAGGTGA AGGTTGCTGT GGGCCAAAAT CATGCCATTG CACTCCAGCC     5880

TGGGTGACAA GAGCGAAACT CCATCTCAAA AA                                   5912
```

(2) INFORMATION FOR SEQ ID NO:2:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (viii) POSITION IN GENOME:
        (A) CHROMOSOME/SEGMENT: 11q22-23

(xi) SEQUENCE DESCRIPTION: SEQ ID NO:2:

```
ATGAGTCTAG TACTTAATGA TCTGCTTATC TGCTGCCGTC AACTAGAACA TGATAGAGCT      60

ACAGAACGAA AGAAAGAAGT TGAGAAATTT AAGCGCCTGA TTCGAGATCC TGAAACAATT     120

AAACATCTAG ATCGGCATTC AGATTCCAAA CAAGGAAAAT ATTTGAATTG GGATGCTGTT     180

TTTAGATTTT TACAGAAATA TATTCAGAAA GAAACAGAAT GTCTGAGAAT AGCAAAACCA     240

AATGTATCAG CCTCAACACA AGCCTCCAGG CAGAAAAAGA TGCAGGAAAT CAGTAGTTTG     300

GTCAAATACT TCATCAAATG TGCAAACAGA AGAGCACCTA GGCTAAAATG TCAAGAACTC     360

TTAAATTATA TCATGGATAC AGTGAAAGAT TCATCTAATG GTGCTATTTA CGGAGCTGAT     420

TGTAGCAACA TACTACTCAA AGACATTCTT TCTGTGAGAA ATACTGGTG TGAAATATCT     480

CAGCAACAGT GGTTAGAATT GTTCTCTGTG TACTTCAGGC TCTATCTGAA ACCTTCACAA     540

GATGTTCATA GAGTTTTAGT GGCTAGAATA ATTCATGCTG TTACCAAAGG ATGCTGTTCT     600

CAGACTGACG GATTAAATTC CAAATTTTTG GACTTTTTTT CCAAGGCTAT TCAGTGTGCG     660

AGACAAGAAA AGAGCTCTTC AGGTCTAAAT CATATCTTAG CAGCTCTTAC TATCTTCCTC     720

AAGACTTTGG CTGTCAACTT TCGAATTCGA GTGTGTGAAT TAGGAGATGA AATTCTTCCC     780

ACTTTGCTTT ATATTTGGAC TCAACATAGG CTTAATGATT CTTTAAAAGA AGTCATTATT     840

GAATTATTTC AACTGCAAAT TTATATCCAT CATCCGAAAG GAGCCAAAAC CAAGAAAAA     900

GGTGCTTATG AATCAACAAA ATGGAGAAGT ATTTTATACA ACTTATATGA TCTGCTAGTG     960

AATGAGATAA GTCATATAGG AAGTAGAGGA AAGTATTCTT CAGGATTTCG TAATATTGCC    1020

GTCAAAGAAA ATTTGATTGA ATTGATGGCA GATATCTGTC ACCAGGTTTT TAATGAAGAT    1080

ACCAGATCCT TGGAGATTTC TCAATCTTAC ACTACTACAC AAAGAGAATC TAGTGATTAC    1140

AGTGTCCCTT GCAAAAGGAA GAAAATAGAA CTAGGCTGGG AAGTAATAAA AGATCACCTT    1200

CAGAAGTCAC AGAATGATTT TGATCTTGTG CCTTGGCTAC AGATTGCAAC CCAATTAATA    1260

TCAAAGTATC CTGCAAGTTT ACCTAACTGT GAGCTGTCTC CATTACTGAT GATACTATCT    1320

CAGCTTCTAC CCCAACAGCG ACATGGGGAA CGTACACCAT ATGTGTTACG ATGCCTTACG    1380

GAAGTTGCAT TGTGTCAAGA CAAGAGGTCA AACCTAGAAA GCTCACAAAA GTCAGATTTA    1440

TTAAAACTCT GGAATAAAAT TTGGTGTATT ACCTTTCGTG GTATAAGTTC TGAGCAAATA    1500

CAAGCTGAAA ACTTTGGCTT ACTTGGAGCC ATAATTCAGG GTAGTTTAGT TGAGGTTGAC    1560

AGAGAATTCT GGAAGTTATT TACTGGGTCA GCCTGCAGAC CTTCATGTCC TGCAGTATGC    1620

TGTTTGACTT TGGCACTGAC CACCAGTATA GTTCCAGGAA CGGTAAAAAT GGGAATAGAG    1680

CAAAATATGT GTGAAGTAAA TAGAAGCTTT TCTTTAAAGG AATCAATAAT GAAATGGCTC    1740

TTATTCTATC AGTTAGAGGG TGACTTAGAA AATAGCACAG AAGTGCCTCC AATTCTTCAC    1800

AGTAATTTTC CTCATCTTGT ACTGGAGAAA ATTCTTGTGA GTCTCACTAT GAAAACTGT    1860

AAAGCTGCAA TGAATTTTTT CCAAAGCGTG CCAGAATGTG AACACCACCA AAAAGATAAA    1920

GAAGAACTTT CATTCTCAGA AGTAGAAGAA CTATTTCTTC AGACAACTTT TGACAAGATG    1980

GACTTTTTAA CCATTGTGAG AGAATGTGGT ATAGAAAAGC ACCAGTCCAG TATTGGCTTC    2040

TCTGTCCACC AGAATCTCAA GGAATCACTG GATCGCTGTC TTCTGGGATT ATCAGAACAG    2100

CTTCTGAATA ATTACTCATC TGAGATTACA AATTCAGAAA CTCTTGTCCG TGTTCACGT    2160

CTTTTGGTGG GTGTCCTTGG CTGCTACTGT TACATGGGTG TAATAGCTGA AGAGGAAGCA    2220

TATAAGTCAG AATTATTCCA GAAAGCCAAG TCTCTAATGC AATGTGCAGG AGAAAGTATC    2280
```

```
ACTCTGTTTA AAAATAAGAC AAATGAGGAA TTCAGAATTG GTTCCTTGAG AAATATGATG    2340

CAGCTATGTA CACGTTGCTT GAGCAACTGT ACCAAGAAGA GTCCAAATAA GATTGCATCT    2400

GGCTTTTTCC TGCGATTGTT AACATCAAAG CTAATGAATG ACATTGCAGA TATTTGTAAA    2460

AGTTTAGCAT CCTTCATCAA AAAGCCATTT GACCGTGGAG AAGTAGAATC AATGGAAGAT    2520

GATACTAATG GAAATCTAAT GGAGGTGGAG GATCAGTCAT CCATGAATCT ATTTAACGAT    2580

TACCCTGATA GTAGTGTTAG TGATGCAAAC GAACCTGGAG AGAGCCAAAG TACCATAGGT    2640

GCCATTAATC CTTTAGCTGA AGAATATCTG TCAAAGCAAG ATCTACTTTT CTTAGACATG    2700

CTCAAGTTCT TGTGTTTGTG TGTAACTACT GCTCAGACCA ATACTGTGTC CTTTAGGGCA    2760

GCTGATATTC GGAGGAAATT GTTAATGTTA ATTGATTCTA GCACGCTAGA ACCTACCAAA    2820

TCCCTCCACC TGCATATGTA TCTAATGCTT TTAAAGGAGC TTCCTGGAGA AGAGTACCCC    2880

TTGCCAATGG AAGATGTTCT TGAACTTCTG AAACCACTAT CCAATGTGTG TTCTTTGTAT    2940

CGTCGTGACC AAGATGTTTG TAAAACTATT TTAAACCATG TCCTTCATGT AGTGAAAAAC    3000

CTAGGTCAAA GCAATATGGA CTCTGAGAAC ACAAGGGATG CTCAAGGACA GTTTCTTACA    3060

GTAATTGGAG CATTTTGGCA TCTAACAAAG GAGAGGAAAT ATATATTCTC TGTAAGAATG    3120

GCCCTAGTAA ATTGCCTTAA AACTTTGCTT GAGGCTGATC CTTATTCAAA ATGGGCCATT    3180

CTTAATGTAA TGGGAAAAGA CTTTCCTGTA AATGAAGTAT TTACACAATT TCTTGCTGAC    3240

AATCATCACC AAGTTCGCAT GTTGGCTGCA GAGTCAATCA ATAGATTGTT CCAGGACACG    3300

AAGGGAGATT CTTCCAGGTT ACTGAAAGCA CTTCCTTTGA AGCTTCAGCA AACAGCTTTT    3360

GAAAATGCAT ACTTGAAAGC TCAGGAAGGA ATGAGAGAAA TGTCCCATAG TGCTGAGAAC    3420

CCTGAAACTT TGGATGAAAT TTATAATAGA AAATCTGTTT TACTGACGTT GATAGCTGTG    3480

GTTTTATCCT GTAGCCCTAT CTGCGAAAAA CAGGCTTTGT TTGCCCTGTG TAAATCTGTG    3540

AAAGAGAATG GATTAGAACC TCACCTTGTG AAAAAGGTTT TAGAGAAAGT TTCTGAAACT    3600

TTTGGATATA GACGTTTAGA AGACTTTATG GCATCTCATT TAGATTATCT GGTTTTGGAA    3660

TGGCTAAATC TTCAAGATAC TGAATACAAC TTATCTTCTT TTCCTTTTAT TTTATTAAAC    3720

TACACAAATA TTGAGGATTT CTATAGATCT TGTTATAAGG TTTTGATTCC ACATCTGGTG    3780

ATTAGAAGTC ATTTTGATGA GGTGAAGTCC ATTGCTAATC AGATTCAAGA GGACTGGAAA    3840

AGTCTTCTAA CAGACTGCTT TCCAAAGATT CTTGTAAATA TTCTTCCTTA TTTTGCCTAT    3900

GAGGGTACCA GAGACAGTGG GATGGCACAG CAAAGAGAGA CTGCTACCAA GGTCTATGAT    3960

ATGCTTAAAA GTGAAAACTT ATTGGGAAAA CAGATTGATC ACTTATTCAT TAGTAATTTA    4020

CCAGAGATTG TGGTGGAGTT ATTGATGACG TTACATGAGC CAGCAAATTC TAGTGCCAGT    4080

CAGAGCACTG ACCTCTGTGA CTTTTCAGGG GATTTGGATC CTGCTCCTAA TCCACCTCAT    4140

TTTCCATCGC ATGTGATTAA AGCAACATTT GCCTATATCA GCAATTGTCA TAAAACCAAG    4200

TTAAAAAGCA TTTTAGAAAT TCTTTCCAAA AGCCCTGATT CCTATCAGAA AATTCTTCTT    4260

GCCATATGTG AGCAAGCAGC TGAAACAAAT AATGTTTATA AGAAGCACAG AATTCTTAAA    4320

ATATATCACC TGTTTGTTAG TTTATTACTG AAAGATATAA AAAGTGGCTT AGGAGGAGCT    4380

TGGGCCTTTG TTCTTCGAGA CGTTATTTAT ACTTTGATTC ACTATATCAA CCAAAGGCCT    4440

TCTTGTATCA TGGATGTGTC ATTACGTAGC TTCTCCCTTT GTTGTGACTT ATTAAGTCAG    4500

GTTTGCCAGA CAGCCGTGAC TTACTGTAAG GATGCTCTAG AAAACCATCT TCATGTTATT    4560

GTTGGTACAC TTATACCCCT TGTGTATGAG CAGGTGGAGG TTCAGAAACA GGTATTGGAC    4620

TTGTTGAAAT ACTTAGTGAT AGATAACAAG GATAATGAAA ACCTCTATAT CACGATTAAG    4680
```

-continued

```
CTTTTAGATC CTTTTCCTGA CCATGTTGTT TTTAAGGATT GCGTATTAC TCAGCAAAAA      4740

ATCAAATACA GTAGAGGACC CTTTTCACTC TTGGAGGAAA TTAACCATTT TCTCTCAGTA      4800

AGTGTTTATG ATGCACTTCC ATTGACAAGA CTTGAAGGAC TAAAGGATCT TCGAAGACAA      4860

CTGGAACTAC ATAAAGATCA GATGGTGGAC ATTATGAGAG CTTCTCAGGA TAATCCGCAA      4920

GATGGGATTA TGGTGAAACT AGTTGTCAAT TTGTTGCAGT TATCCAAGAT GGCAATAAAC      4980

CACACTGGTG AAAAGAAGT TCTAGAGGCT GTTGGAAGCT GCTTGGGAGA AGTGGGTCCT       5040

ATAGATTTCT CTACCATAGC TATACAACAT AGTAAAGATG CATCTTATAC CAAGGCCCTT      5100

AAGTTATTTG AAGATAAAGA ACTTCAGTGG ACCTTCATAA TGCTGACCTA CCTGAATAAC      5160

ACACTGGTAG AAGATTGTGT CAAAGTTCGA TCAGCAGCTG TTACCTGTTT GAAAACATT      5220

TTAGCCACAA AGACTGGACA TAGTTTCTGG GAGATTTATA AGATGACAAC AGATCCAATG      5280

CTGGCCTATC TACAGCCTTT TAGAACATCA AGAAAAAAGT TTTTAGAAGT ACCCAGATTT      5340

GACAAAGAAA ACCCTTTTGA AGGCCTGGAT GATATAAATC TGTGGATTCC TCTAAGTGAA      5400

AATCATGACA TTTGGATAAA GACACTGACT TGTGCTTTTT TGGACAGTGG AGGCACAAAA     5460

TGTGAAATTC TTCAATTATT AAAGCCAATG TGTGAAGTGA AAACTGACTT TTGTCAGACT      5520

GTACTTCCAT ACTTGATTCA TGATATTTTA CTCCAAGATA CAAATGAATC ATGGAGAAAT      5580

CTGCTTTCTA CACATGTTCA GGGATTTTTC ACCAGCTGTC TTCGACACTT CTCGCAAACG     5640

AGCCGATCCA CAACCCCTGC AAACTTGGAT TCAGAGTCAG AGCACTTTTT CCGATGCTGT     5700

TTGGATAAAA AATCACAAAG AACAATGCTT GCTGTTGTGG ACTACATGAG AAGACAAAAG     5760

AGACCTTCTT CAGGAACAAT TTTTAATGAT GCTTTCTGGC TGGATTTAAA TTATCTAGAA     5820

GTTGCCAAGG TAGCTCAGTC TTGTGCTGCT CACTTTACAG CTTTACTCTA TGCAGAAATC     5880

TATGCAGATA AGAAAAGTAT GGATGATCAA GAGAAAAGAA GTCTTGCATT TGAAGAAGGA     5940

AGCCAGAGTA CAACTATTTC TAGCTTGAGT GAAAAAAGTA AGAAGAAAC TGGAATAAGT      6000

TTACAGGATC TTCTCTTAGA AATCTACAGA AGTATAGGGG AGCCAGATAG TTTGTATGGC     6060

TGTGGTGGAG GGAAGATGTT ACAACCCATT ACTAGACTAC GAACATATGA ACACGAAGCA     6120

ATGTGGGCA AAGCCCTAGT AACATATGAC CTCGAAACAG CAATCCCCTC ATCAACACGC      6180

CAGGCAGGAA TCATTCAGGC CTTGCAGAAT TTGGGACTCT GCCATATTCT TTCCGTCTAT     6240

TTAAAAGGAT TGGATTATGA AAATAAAGAC TGGTGTCCTG AACTAGAAGA ACTTCATTAC     6300

CAAGCAGCAT GGAGGAATAT GCAGTGGGAC CATTGCACTT CCGTCAGCAA AGAAGTAGAA     6360

GGAACCAGTT ACCATGAATC ATTGTACAAT GCTCTACAAT CTCTAAGAGA CAGAGAATTC     6420

TCTACATTTT ATGAAAGTCT CAAATATGCC AGAGTAAAAG AAGTGGAAGA GATGTGTAAG    6480

CGCAGCCTTG AGTCTGTGTA TTCGCTCTAT CCCACACTTA GCAGGTTGCA GGCCATTGGA     6540

GAGCTGGAAA GCATTGGGGA GCTTTTCTCA AGATCAGTCA CACATAGACA ACTCTCTGAA     6600

GTATATATTA AGTGGCAGAA ACACTCCCAG CTTCTCAAGG ACAGTGATTT TAGTTTTCAG     6660

GAGCCTATCA TGGCTCTACG CACAGTCATT TTGGAGATCC TGATGGAAAA GGAAATGGAC     6720

AACTCACAAA GAGAATGTAT TAAGGACATT CTCACCAAAC ACCTTGTAGA ACTCTCTATA     6780

CTGGCCAGAA CTTTCAAGAA CACTCAGCTC CCTGAAAGGG CAATATTTCA AATTAAACAG     6840

TACAATTCAG TTAGCTGTGG AGTCTCTGAG TGGCAGCTGG AAGAAGCACA AGTATTCTGG     6900

GCAAAAAAGG AGCAGAGTCT TGCCCTGAGT ATTCTCAAGC AAATGATCAA GAAGTTGGAT     6960

GCCAGCTGTG CAGCGAACAA TCCCAGCCTA AAACTTACAT ACACAGAATG TCTGAGGGTT     7020
```

```
TGTGGCAACT GGTTAGCAGA AACGTGCTTA GAAAATCCTG CGGTCATCAT GCAGACCTAT    7080

CTAGAAAAGG CAGTAGAAGT TGCTGGAAAT TATGATGGAG AAAGTAGTGA TGAGCTAAGA    7140

AATGGAAAAA TGAAGGCATT TCTCTCATTA GCCCGGTTTT CAGATACTCA ATACCAAAGA    7200

ATTGAAAACT ACATGAAATC ATCGGAATTT GAAAACAAGC AAGCTCTCCT GAAAAGAGCC    7260

AAAGAGGAAG TAGGTCTCCT TAGGGAACAT AAAATTCAGA CAAACAGATA CACAGTAAAG    7320

GTTCAGCGAG AGCTGGAGTT GGATGAATTA GCCCTGCGTG CACTGAAAGA GGATCGTAAA    7380

CGCTTCTTAT GTAAAGCAGT TGAAAATTAT ATCAACTGCT TATTAAGTGG AGAAGAACAT    7440

GATATGTGGG TATTCCGACT TTGTTCCCTC TGGCTTGAAA ATTCTGGAGT TTCTGAAGTC    7500

AATGGCATGA TGAAGAGAGA CGGAATGAAG ATTCCAACAT ATAAATTTTT GCCTCTTATG    7560

TACCAATTGG CTGCTAGAAT GGGGACCAAG ATGATGGGAG CCTAGGATT TCATGAAGTC     7620

CTCAATAATC TAATCTCTAG AATTTCAATG GATCACCCCC ATCACACTTT GTTTATTATA    7680

CTGGCCTTAG CAAATGCAAA CAGAGATGAA TTTCTGACTA AACCAGAGGT AGCCAGAAGA    7740

AGCAGAATAA CTAAAAATGT GCCTAAACAA AGCTCTCAGC TTGATGAGGA TCGAACAGAG    7800

GCTGCAAATA GAATAATATG TACTATCAGA AGTAGGAGAC CTCAGATGGT CAGAAGTGTT    7860

GAGGCACTTT GTGATGCTTA TATTATATTA GCAAACTTAG ATGCCACTCA GTGGAAGACT    7920

CAGAGAAAAG GCATAAATAT TCCAGCAGAC CAGCCAATTA CTAAACTTAA GAATTTAGAA    7980

GATGTTGTTG TCCCTACTAT GGAAATTAAG GTGGACCACA CAGGAGAATA TGGAAATCTG    8040

GTGACTATAC AGTCATTTAA AGCAGAATTT CGCTTAGCAG GAGGTGTAAA TTTACCAAAA    8100

ATAATAGATT GTGTAGGTTC CGATGGCAAG GAGAGGAGAC AGCTTGTTAA GGGCCGTGAT    8160

GACCTGAGAC AAGATGCTGT CATGCAACAG GTCTTCCAGA TGTGTAATAC ATTACTGCAG    8220

AGAAACACGG AAACTAGGAA GAGGAAATTA ACTATCTGTA CTTATAAGGT GGTTCCCCTC    8280

TCTCAGCGAA GTGGTGTTCT TGAATGGTGC ACAGGAACTG TCCCCATTGG TGAATTTCTT    8340

GTTAACAATG AAGATGGTGC TCATAAAAGA TACAGGCCAA ATGATTTCAG TGCCTTTCAG    8400

TGCCAAAAGA AAATGATGGA GGTGCAAAAA AAGTCTTTTG AAGAGAAATA TGAAGTCTTC    8460

ATGGATGTTT GCCAAAATTT TCAACCAGTT TTCCGTTACT TCTGCATGGA AAAATTCTTG    8520

GATCCAGCTA TTTGGTTTGA GAAGCGATTG GCTTATACGC GCAGTGTAGC TACTTCTTCT    8580

ATTGTTGGTT ACATACTTGG ACTTGGTGAT AGACATGTAC AGAATATCTT GATAAATGAG    8640

CAGTCAGCAG AACTTGTACA TATAGATCTA GGTGTTGCTT TTGAACAGGG CAAAATCCTT    8700

CCTACTCCTG AGACAGTTCC TTTTAGACTC ACCAGAGATA TTGTGGATGG CATGGGCATT    8760

ACGGGTGTTG AAGGTGTCTT CAGAAGATGC TGTGAGAAAA CCATGGAAGT GATGAGAAAC    8820

TCTCAGGAAA CTCTGTTAAC CATTGTAGAG GTCCTTCTAT ATGATCCACT CTTTGACTGG    8880

ACCATGAATC CTTTGAAAGC TTTGTATTTA CAGCAGAGGC CGGAAGATGA AACTGAGCTT    8940

CACCCTACTC TGAATGCAGA TGACCAAGAA TGCAAACGAA ATCTCAGTGA TATTGACCAG    9000

AGTTTCAACA AAGTAGCTGA ACGTGTCTTA ATGAGACTAC AAGAGAAACT GAAAGGAGTG    9060

GAAGAAGGCA CTGTGCTCAG TGTTGGTGGA CAAGTGAATT TGCTCATACA GCAGGCCATA    9120

GACCCCAAAA ATCTCAGCCG ACTTTTCCCA GGATGGAAAG CTTGGGTGTG A             9171
```

(2) INFORMATION FOR SEQ ID NO:3:

(i) SEQUENCE CHARACTERISTICS:
        (A) LENGTH: 3056 amino acids
        (B) TYPE: amino acid
        (C) STRANDEDNESS: single -continued

```
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:3:

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
            85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
            115                 120                 125

Lys Asp Ser Ser Asn Gly Ala Ile Tyr Gly Ala Asp Cys Ser Asn Ile
130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
                180                 185                 190

Ala Val Thr Lys Gly Cys Cys Ser Gln Thr Asp Gly Leu Asn Ser Lys
            195                 200                 205

Phe Leu Asp Phe Phe Ser Lys Ala Ile Gln Cys Ala Arg Gln Glu Lys
210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Val Tyr Ile Trp Thr Gln His Arg Leu Asn
            260                 265                 270

Asp Ser Leu Lys Glu Val Ile Ile Glu Leu Phe Gln Leu Gln Ile Tyr
            275                 280                 285

Ile His His Pro Lys Gly Ala Lys Thr Gln Glu Lys Gly Ala Tyr Glu
            290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
                340                 345                 350

Cys His Gln Val Phe Asn Glu Asp Thr Arg Ser Leu Glu Ile Ser Gln
            355                 360                 365

Ser Tyr Thr Thr Thr Gln Arg Glu Ser Ser Asp Tyr Ser Val Pro Cys
```

-continued

```
            370                 375                 380
Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
                420                 425                 430

Ser Pro Leu Leu Met Ile Leu Ser Gln Leu Leu Pro Gln Gln Arg His
                435                 440                 445

Gly Glu Arg Thr Pro Tyr Val Leu Arg Cys Leu Thr Glu Val Ala Leu
                450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Lys Gln Ala Glu Asn Phe Gly Leu Leu Gly Ala Ile Ile
                500                 505                 510

Gln Gly Ser Leu Val Glu Val Asp Arg Glu Phe Trp Lys Leu Phe Thr
                515                 520                 525

Gly Ser Ala Cys Arg Pro Ser Cys Pro Ala Val Cys Cys Leu Thr Leu
                530                 535                 540

Ala Leu Thr Thr Ser Ile Val Pro Gly Ala Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
                580                 585                 590

Thr Glu Val Pro Pro Ile Leu His Ser Asn Phe Pro His Leu Val Leu
                595                 600                 605

Glu Lys Ile Leu Val Ser Leu Thr Met Lys Asn Cys Lys Ala Ala Met
                610                 615                 620

Asn Phe Phe Gln Ser Val Pro Glu Cys Glu His His Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
                660                 665                 670

Lys His Gln Ser Ser Ile Gly Phe Ser Val His Gln Asn Leu Lys Glu
                675                 680                 685

Ser Leu Asp Arg Cys Leu Leu Gly Leu Ser Gln Leu Leu Asn Asn
                690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
                740                 745                 750

Met Gln Cys Ala Gly Glu Ser Ile Thr Leu Phe Lys Asn Lys Thr Asn
                755                 760                 765

Glu Glu Phe Arg Ile Gly Ser Leu Arg Asn Met Met Gln Leu Cys Thr
                770                 775                 780

Arg Cys Leu Ser Asn Cys Thr Lys Lys Ser Pro Asn Lys Ile Ala Ser
785                 790                 795                 800
```

```
Gly Phe Phe Leu Arg Leu Leu Thr Ser Lys Leu Met Asn Asp Ile Ala
            805                 810                 815

Asp Ile Cys Lys Ser Leu Ala Ser Phe Ile Lys Lys Pro Phe Asp Arg
            820                 825                 830

Gly Glu Val Glu Ser Met Glu Asp Asp Thr Asn Gly Asn Leu Met Glu
            835                 840                 845

Val Glu Asp Gln Ser Ser Met Asn Leu Phe Asn Asp Tyr Pro Asp Ser
        850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
                900                 905                 910

Thr Asn Thr Val Ser Phe Arg Ala Ala Asp Ile Arg Arg Lys Leu Leu
            915                 920                 925

Met Leu Ile Asp Ser Ser Thr Leu Glu Pro Thr Lys Ser Leu His Leu
        930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn Leu Gly Gln Ser Asn Met Asp Ser
        995                 1000                1005

Glu Asn Thr Arg Asp Ala Gln Gly Gln Phe Leu Thr Val Ile Gly Ala
        1010                1015                1020

Phe Trp His Leu Thr Lys Glu Arg Lys Tyr Ile Phe Ser Val Arg Met
1025                1030                1035                1040

Ala Leu Val Asn Cys Leu Lys Thr Leu Leu Glu Ala Asp Pro Tyr Ser
                1045                1050                1055

Lys Trp Ala Ile Leu Asn Val Met Gly Lys Asp Phe Pro Val Asn Glu
            1060                1065                1070

Val Phe Thr Gln Phe Leu Ala Asp Asn His His Gln Val Arg Met Leu
        1075                1080                1085

Ala Ala Glu Ser Ile Asn Arg Leu Phe Gln Asp Thr Lys Gly Asp Ser
        1090                1095                1100

Ser Arg Leu Leu Lys Ala Leu Pro Leu Lys Leu Gln Gln Thr Ala Phe
1105                1110                1115                1120

Glu Asn Ala Tyr Leu Lys Ala Gln Glu Gly Met Arg Glu Met Ser His
                1125                1130                1135

Ser Ala Glu Asn Pro Glu Thr Leu Asp Glu Ile Tyr Asn Arg Lys Ser
            1140                1145                1150

Val Leu Leu Thr Leu Ile Ala Val Val Leu Ser Cys Ser Pro Ile Cys
        1155                1160                1165

Glu Lys Gln Ala Leu Phe Ala Leu Cys Lys Ser Val Lys Glu Asn Gly
        1170                1175                1180

Leu Glu Pro His Leu Val Lys Lys Val Leu Glu Lys Val Ser Glu Thr
1185                1190                1195                1200

Phe Gly Tyr Arg Arg Leu Glu Asp Phe Met Ala Ser His Leu Asp Tyr
                1205                1210                1215
```

-continued

```
Leu Val Leu Glu Trp Leu Asn Leu Gln Asp Thr Glu Tyr Asn Leu Ser
        1220                1225                1230

Ser Phe Pro Phe Ile Leu Leu Asn Tyr Thr Asn Ile Glu Asp Phe Tyr
        1235                1240                1245

Arg Ser Cys Tyr Lys Val Leu Ile Pro His Leu Val Ile Arg Ser His
        1250                1255                1260

Phe Asp Glu Val Lys Ser Ile Ala Asn Gln Ile Gln Glu Asp Trp Lys
1265                1270                1275                1280

Ser Leu Leu Thr Asp Cys Phe Pro Lys Ile Leu Val Asn Ile Leu Pro
        1285                1290                1295

Tyr Phe Ala Tyr Glu Gly Thr Arg Asp Ser Gly Met Ala Gln Gln Arg
        1300                1305                1310

Glu Thr Ala Thr Lys Val Tyr Asp Met Leu Lys Ser Glu Asn Leu Leu
        1315                1320                1325

Gly Lys Gln Ile Asp His Leu Phe Ile Ser Asn Leu Pro Glu Ile Val
        1330                1335                1340

Val Glu Leu Leu Met Thr Leu His Glu Pro Ala Asn Ser Ser Ala Ser
1345                1350                1355                1360

Gln Ser Thr Asp Leu Cys Asp Phe Ser Gly Asp Leu Asp Pro Ala Pro
        1365                1370                1375

Asn Pro Pro His Phe Pro Ser His Val Ile Lys Ala Thr Phe Ala Tyr
        1380                1385                1390

Ile Ser Asn Cys His Lys Thr Lys Leu Lys Ser Ile Leu Glu Ile Leu
        1395                1400                1405

Ser Lys Ser Pro Asp Ser Tyr Gln Lys Ile Leu Leu Ala Ile Cys Glu
        1410                1415                1420

Gln Ala Ala Glu Thr Asn Asn Val Tyr Lys Lys His Arg Ile Leu Lys
1425                1430                1435                1440

Ile Tyr His Leu Phe Val Ser Leu Leu Leu Lys Asp Ile Lys Ser Gly
        1445                1450                1455

Leu Gly Gly Ala Trp Ala Phe Val Leu Arg Asp Val Ile Tyr Thr Leu
        1460                1465                1470

Ile His Tyr Ile Asn Gln Arg Pro Ser Cys Ile Met Asp Val Ser Leu
        1475                1480                1485

Arg Ser Phe Ser Leu Cys Cys Asp Leu Leu Ser Gln Val Cys Gln Thr
        1490                1495                1500

Ala Val Thr Tyr Cys Lys Asp Ala Leu Glu Asn His Leu His Val Ile
1505                1510                1515                1520

Val Gly Thr Leu Ile Pro Leu Val Tyr Glu Gln Val Glu Val Gln Lys
        1525                1530                1535

Gln Val Leu Asp Leu Leu Lys Tyr Leu Val Ile Asp Asn Lys Asp Asn
        1540                1545                1550

Glu Asn Leu Tyr Ile Thr Ile Lys Leu Leu Asp Pro Phe Pro Asp His
        1555                1560                1565

Val Val Phe Lys Asp Leu Arg Ile Thr Gln Gln Lys Ile Lys Tyr Ser
        1570                1575                1580

Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
        1605                1610                1615

Leu Arg Arg Gln Leu Glu Leu His Lys Asp Gln Met Val Asp Ile Met
        1620                1625                1630

Arg Ala Ser Gln Asp Asn Pro Gln Asp Gly Ile Met Val Lys Leu Val
```

-continued

```
                1635                1640                1645

Val Asn Leu Gln Leu Ser Lys Met Ala Ile Asn His Thr Gly Glu
1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
                1685                1690                1695

Thr Lys Ala Leu Lys Leu Phe Glu Asp Lys Glu Leu Gln Trp Thr Phe
                1700                1705                1710

Ile Met Leu Thr Tyr Leu Asn Asn Thr Leu Val Glu Asp Cys Val Lys
                1715                1720                1725

Val Arg Ser Ala Ala Val Thr Cys Leu Lys Asn Ile Leu Ala Thr Lys
                1730                1735                1740

Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
                1765                1770                1775

Val Pro Arg Phe Asp Lys Glu Asn Pro Phe Glu Gly Leu Asp Asp Ile
                1780                1785                1790

Asn Leu Trp Ile Pro Leu Ser Glu Asn His Asp Ile Trp Ile Lys Thr
                1795                1800                1805

Leu Thr Cys Ala Phe Leu Asp Ser Gly Gly Thr Lys Cys Glu Ile Leu
                1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
                1845                1850                1855

Ser Trp Arg Asn Leu Leu Ser Thr His Val Gln Gly Phe Phe Thr Ser
                1860                1865                1870

Cys Leu Arg His Phe Ser Gln Thr Ser Arg Ser Thr Thr Pro Ala Asn
                1875                1880                1885

Leu Asp Ser Glu Ser Glu His Phe Phe Arg Cys Cys Leu Asp Lys Lys
                1890                1895                1900

Ser Gln Arg Thr Met Leu Ala Val Val Asp Tyr Met Arg Arg Gln Lys
1905                1910                1915                1920

Arg Pro Ser Ser Gly Thr Ile Phe Asn Asp Ala Phe Trp Leu Asp Leu
                1925                1930                1935

Asn Tyr Leu Glu Val Ala Lys Val Ala Gln Ser Cys Ala Ala His Phe
                1940                1945                1950

Thr Ala Leu Leu Tyr Ala Glu Ile Tyr Ala Asp Lys Lys Ser Met Asp
                1955                1960                1965

Asp Gln Glu Lys Arg Ser Leu Ala Phe Glu Glu Gly Ser Gln Ser Thr
                1970                1975                1980

Thr Ile Ser Ser Leu Ser Glu Lys Ser Lys Glu Glu Thr Gly Ile Ser
1985                1990                1995                2000

Leu Gln Asp Leu Leu Leu Glu Ile Tyr Arg Ser Ile Gly Glu Pro Asp
                2005                2010                2015

Ser Leu Tyr Gly Cys Gly Gly Gly Lys Met Leu Gln Pro Ile Thr Arg
                2020                2025                2030

Leu Arg Thr Tyr Glu His Glu Ala Met Trp Gly Lys Ala Leu Val Thr
                2035                2040                2045

Tyr Asp Leu Glu Thr Ala Ile Pro Ser Ser Thr Arg Gln Ala Gly Ile
                2050                2055                2060
```

```
Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
            2085                2090                2095

Glu Leu His Tyr Gln Ala Ala Trp Arg Asn Met Gln Trp Asp His Cys
        2100                2105                2110

Thr Ser Val Ser Lys Glu Val Glu Gly Thr Ser Tyr His Glu Ser Leu
    2115                2120                2125

Tyr Asn Ala Leu Gln Ser Leu Arg Asp Arg Glu Phe Ser Thr Phe Tyr
2130                2135                2140

Glu Ser Leu Lys Tyr Ala Arg Val Lys Glu Val Glu Met Cys Lys
2145                2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
        2180                2185                2190

Val Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile Met
2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
        2260                2265                2270

Arg Ala Ile Phe Gln Ile Lys Gln Tyr Asn Ser Val Ser Cys Gly Val
    2275                2280                2285

Ser Glu Trp Gln Leu Glu Glu Ala Gln Val Phe Trp Ala Lys Lys Glu
        2290                2295                2300

Gln Ser Leu Ala Leu Ser Ile Leu Lys Gln Met Ile Lys Lys Leu Asp
2305                2310                2315                2320

Ala Ser Cys Ala Ala Asn Asn Pro Ser Leu Lys Leu Thr Tyr Thr Glu
            2325                2330                2335

Cys Leu Arg Val Cys Gly Asn Trp Leu Ala Glu Thr Cys Leu Glu Asn
            2340                2345                2350

Pro Ala Val Ile Met Gln Thr Tyr Leu Glu Lys Ala Val Glu Val Ala
        2355                2360                2365

Gly Asn Tyr Asp Gly Glu Ser Ser Asp Glu Leu Arg Asn Gly Lys Met
    2370                2375                2380

Lys Ala Phe Leu Ser Leu Ala Arg Phe Ser Asp Thr Gln Tyr Gln Arg
2385                2390                2395                2400

Ile Glu Asn Tyr Met Lys Ser Ser Glu Phe Glu Asn Lys Gln Ala Leu
            2405                2410                2415

Leu Lys Arg Ala Lys Glu Glu Val Gly Leu Leu Arg Glu His Lys Ile
        2420                2425                2430

Gln Thr Asn Arg Tyr Thr Val Lys Val Gln Arg Glu Leu Glu Leu Asp
    2435                2440                2445

Glu Leu Ala Leu Arg Ala Leu Lys Glu Asp Arg Lys Arg Phe Leu Cys
2450                2455                2460

Lys Ala Val Glu Asn Tyr Ile Asn Cys Leu Leu Ser Gly Glu Glu His
2465                2470                2475                2480
```

```
Asp Met Trp Val Phe Arg Leu Cys Ser Leu Trp Leu Glu Asn Ser Gly
            2485                2490                2495

Val Ser Glu Val Asn Gly Met Met Lys Arg Asp Gly Met Lys Ile Pro
        2500                2505                2510

Thr Tyr Lys Phe Leu Pro Leu Met Tyr Gln Leu Ala Ala Arg Met Gly
        2515                2520                2525

Thr Lys Met Met Gly Gly Leu Gly Phe His Val Leu Asn Asn Leu
        2530                2535                2540

Ile Ser Arg Ile Ser Met Asp His Pro His His Thr Leu Phe Ile Ile
2545                2550                2555                2560

Leu Ala Leu Ala Asn Ala Asn Arg Asp Glu Phe Leu Thr Lys Pro Glu
            2565                2570                2575

Val Ala Arg Arg Ser Arg Ile Thr Lys Asn Val Pro Lys Gln Ser Ser
        2580                2585                2590

Gln Leu Asp Glu Asp Arg Thr Glu Ala Ala Asn Arg Ile Ile Cys Thr
        2595                2600                2605

Ile Arg Ser Arg Arg Pro Gln Met Val Arg Ser Val Glu Ala Leu Cys
    2610                2615                2620

Asp Ala Tyr Ile Ile Leu Ala Asn Leu Asp Ala Thr Gln Trp Lys Thr
2625                2630                2635                2640

Gln Arg Lys Gly Ile Asn Ile Pro Ala Asp Gln Pro Ile Thr Lys Leu
            2645                2650                2655

Lys Asn Leu Glu Asp Val Val Pro Thr Met Glu Ile Lys Val Asp
        2660                2665                2670

His Thr Gly Glu Tyr Gly Asn Leu Val Thr Ile Gln Ser Phe Lys Ala
            2675                2680                2685

Glu Phe Arg Leu Ala Gly Gly Val Asn Leu Pro Lys Ile Ile Asp Cys
        2690                2695                2700

Val Gly Ser Asp Gly Lys Glu Arg Arg Gln Leu Val Lys Gly Arg Asp
2705                2710                2715                2720

Asp Leu Arg Gln Asp Ala Val Met Gln Gln Val Phe Gln Met Cys Asn
            2725                2730                2735

Thr Leu Leu Gln Arg Asn Thr Glu Thr Arg Lys Arg Lys Leu Thr Ile
            2740                2745                2750

Cys Thr Tyr Lys Val Val Pro Leu Ser Gln Arg Ser Gly Val Leu Glu
        2755                2760                2765

Trp Cys Thr Gly Thr Val Pro Ile Gly Glu Phe Leu Val Asn Asn Glu
        2770                2775                2780

Asp Gly Ala His Lys Arg Tyr Arg Pro Asn Asp Phe Ser Ala Phe Gln
2785                2790                2795                2800

Cys Gln Lys Lys Met Met Glu Val Gln Lys Lys Ser Phe Glu Glu Lys
            2805                2810                2815

Tyr Glu Val Phe Met Asp Val Cys Gln Asn Phe Gln Pro Val Phe Arg
        2820                2825                2830

Tyr Phe Cys Met Glu Lys Phe Leu Asp Pro Ala Ile Trp Phe Glu Lys
        2835                2840                2845

Arg Leu Ala Tyr Thr Arg Ser Val Ala Thr Ser Ser Ile Val Gly Tyr
        2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
            2885                2890                2895

Gly Lys Ile Leu Pro Thr Pro Glu Thr Val Pro Phe Arg Leu Thr Arg
```

-continued

```
                     2900                2905                2910
Asp Ile Val Asp Gly Met Gly Ile Thr Gly Val Glu Gly Val Phe Arg
            2915                2920                2925
Arg Cys Cys Glu Lys Thr Met Glu Val Met Arg Asn Ser Gln Glu Thr
    2930                2935                2940
Leu Leu Thr Ile Val Glu Val Leu Leu Tyr Asp Pro Leu Phe Asp Trp
2945                2950                2955                2960
Thr Met Asn Pro Leu Lys Ala Leu Tyr Leu Gln Gln Arg Pro Glu Asp
            2965                2970                2975
Glu Thr Glu Leu His Pro Thr Leu Asn Ala Asp Asp Gln Glu Cys Lys
        2980                2985                2990
Arg Asn Leu Ser Asp Ile Asp Gln Ser Phe Asp Lys Val Ala Glu Arg
        2995                3000                3005
Val Leu Met Arg Leu Gln Glu Lys Leu Lys Gly Val Glu Glu Gly Thr
    3010                3015                3020
Val Leu Ser Val Gly Gly Gln Val Asn Leu Leu Ile Gln Gln Ala Ile
3025                3030                3035                3040
Asp Pro Lys Asn Leu Ser Arg Leu Phe Pro Gly Trp Lys Ala Trp Val
            3045                3050                3055
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
His Glu Pro Ala Asn Ser Ser Ala Ser Gln Ser Thr Asp Leu Cys
1               5                   10                  15
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Cys Lys Arg Asn Leu Ser Asp Ile Asp Gln Ser Phe Asp Lys Val
1               5                   10                  15
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Pro Glu Asp Glu Thr Glu Leu His Pro Thr Leu Asn Ala Asp Asp Gln
1               5                   10                  15
Glu Cys
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Cys Lys Ser Leu Ala Ser Phe Ile Lys Lys Pro Phe Asp Arg Gly Glu
 1               5                  10                  15

Val Glu Ser Met Glu Asp Asp Thr Asn Gly
                20                  25
```

(2) INFORMATION FOR SEQ ID NO:8:

(i) SEQUENCE CHARACTERISTICS:
        (A) LENGTH: 3607 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 3'UTR
        (B) LOCATION: 1..3607

(xi) SEQUENCE DESCRIPTION: SEQ ID NO:8:

```
TCTTCAGTAT ATGAATTACC CTTTCATTCA GCCTTTAGAA ATTATATTTT AGCCTTTATT      60

TTTAACCTGC CAACATACTT TAAGTAGGGA TTAATATTTA AGTGAACTAT TGTGGGTTTT     120

TTTGAATGTT GGTTTTAATA CTTGATTTAA TCACCACTCA AAAATGTTTT GATGGTCTTA     180

AGGAACATCT CTGCTTTCAC TCTTTAGAAA TAATGGTCAT TCGGGCTGGG CGCAGCGGCT     240

CACGCCTGTA ATCCCAGCAC TTTGGGAGGC CGAGGTGAGC GGATCACAAG GTCAGGAGTT     300

CGAGACCAGC CTGGCCAAGA GACCAGCCTG GCCAGTATGG TGAAACCCTG TCTCTACTAA     360

AAATACAAAA ATTAGCCGAG CATGGTGGCG GGCACCTGTA ATCCCAGCTA CTCGAGAGGC     420

TGAGGCAGGA GAATCTCTTG AACCTGGGAG GTGAAGGTTG CTGTGGGCCA AAATCATGCC     480

ATTGCACTCC AGCCTGGGTG ACAAGAGCGA AACTCCATCT CAAAAAAAAA AAAAAAAAAC     540

AGAAACTTAT TTGGATTTTT CCTAGTAAGA TCACTCAGTG TTACTAAATA ATGAAGTTGT     600

TATGGAGAAC AAATTTCAAA GACACAGTTA GTGTAGTTAC TATTTTTTTA AGTGTGTATT     660

AAAACTTCTC ATTCTATTCT CTTTATCTTT TAAGCCCTTC TGTACTGTCC ATGTATGTTA     720

TCTTTCTGTG ATAACTTCAT AGATTGCCTT CTAGTTCATG AATTCTCTTG TCAGATGTAT     780

ATAATCTCTT TTACCCTATC CATTGGGCTT CTTCTTTCAG AAATTGTTTT TCATTTCTAA     840

TTATGCATCA TTTTTCAGAT CTCTGTTTCT TGATGTCATT TTTAATGTTT TTTTAATGTT     900

TTTTATGTCA CTAATTATTT TAAATGTCTG TACCTGATAG ACACTGTAAT AGTTCTATTA     960

AATTTAGTTC CTGCTGTTTA TATCTGTTGA TTTTTGTATT TGATAGGCTG TTCATCCAGT    1020

TTTGTCTTTT TGAAAAGTGA GTTTATTTTC AGCAAGGCTT TATCTATGGG AATCTTGAGT    1080

GTCTGTTTAT GTCATATTCC CAGGGCTGTT GCTGCACACA AGCCCATTCT TATTTTAATT    1140

TCTTGGCTTT AGGGTTTCCA TACCTGAAGT GTAGCATAAA TACTGATAGG AGATTTCCCA    1200
```

```
                                                    -continued

GGCCAAGGCA AACACACTTC CTCCTCATCT CCTTGTGCTA GTGGGCAGAA TATTTGATTG    1260

ATGCCTTTTT CACTGAGAGT ATAAGCTTCC ATGTGTCCCA CCTTTATGGC AGGGGTGGAA    1320

GGAGGTACAT TTAATTCCCA CTGCCTGCCT TTGGCAAGCC CTGGGTTCTT TGCTCCCCAT    1380

ATAGATGTCT AAGCTAAAAG CCGTGGGTTA ATGAGACTGG CAAATTGTTC CAGGACAGCT    1440

ACAGCATCAG CTCACATATT CACCTCTCTG GTTTTTCATT CCCCTCATTT TTTTCTGAGA    1500

CAGAGTCTTG CTCTGTCACC CAGGCTGGAG TGCAGTGGCA TGATCTCAGC TCACTGAAAC    1560

CTCTGCCTCC TGGGTTCAAG CAATTCTCCT GCCTCAGCCT CCCGAGTAGC TGGGACTACA    1620

GGCGTGTGCC AACACGCCCG GCTAATTTTT TGTATTTTTA TTAGAGACGG AGTTTCACCG    1680

TGTTAGCCAG GATGGTCTCG ATCGCTTGAC CTCGTGATCC ACCCTCCTCG GCCTCCCAAA    1740

GTGCTGGGAT TACAGGTGTG AGCCACCGCG CCCGGCCTCA TTCCCCTCAT TTTTGACCGT    1800

AAGGATTTCC CCTTTCTTGT AAGTTCTGCT ATGTATTTAA AGAATGTTT  TCTACATTTT    1860

ATCCAGCATT TCTCTGTGTT CTGTTGGAAG GGAAGGGCTT AGGTATCTAG TTTGATACAT    1920

AGGTAGAAGT GGAACATTTC TCTGTCCCCC AGCTGTCATC ATATAAGATA AACATCAGAT    1980

AAAAAGCCAC CTGAAAGTAA AACTACTGAC TCGTGTATTA GTGAGTATAA TCTCTTCTCC    2040

ATCCTTAGGA AAATGTTCAT CCCAGCTGCG GAGATTAACA AATGGGTGAT TGAGCTTTCT    2100

CCTCGTATTT GGACCTTGAA GGTTATATAA ATTTTTTTCT TATGAAGAGT TGGCATTTCT    2160

TTTTATTGCC AATGGCAGGC ACTCATTCAT ATTTGATCTC CTCACCTTCC CCTCCCCTAA    2220

AACCAATCTC CAGAACTTTT TGGACTATAA ATTTCTTGGT TTGACTTCTG GAGAACTGTT    2280

CAGAATATTA CTTTGCATTT CAAATTACAA ACTTACCTTG GTGTATCTTT TTCTTACAAG    2340

CTGCCTAAAT GAATATTTGG TATATATTGG TAGTTTTATT ACTATAGTAA ATCAAGGAAA    2400

TGCAGTAAAC TTAAAATGTC TTTAAGAAAG CCCTGAAATC TTCATGGGTG AAATTAGAAA    2460

TTATCAACTA GATAATAGTA TAGATAAATG AATTTGTAGC TAATTCTTGC TAGTTGTTGC    2520

ATCCAGAGAG CTTTGAATAA CATCATTAAT CTACTCTTTA GCCTTGCATG GTATGCTATG    2580

AGGCTCCTGT TCTGTTCAAG TATTCTAATC AATGGCTTTG AAAAGTTTAT CAAATTTACA    2640

TACAGATCAC AAGCCTAGGA GAAATAACTA ATTCACAGAT GACAGAATTA AGATTATAAA    2700

AGATTTTTTT TTGGTAATTT TAGTAGAGAC AGGGTTGCCA TTGTATTCCA GCCTTGGCGA    2760

CAGAGCAAGA CTCTGCCTCA AAAAAAAAAA AAAAAAGGTT TTGCCAAGCT GGAACTCTTT    2820

CTGCAAATGA CTAAGATAGA AAACTGCCAA GGACAAATGA GGAGTAGTTA GATTTTGAAA    2880

ATATTAATCA TAGAATAGTT GTTGTATGCT AAGTCACTGA CCCATATTAT GTACAGCATT    2940

TCTGATCTTT ACTTTGCAAG ATTAGTGATA CTATGCCAAT ACACTGCTGG AGAAATCAGA    3000

ATTTGGAGAA ATAAGTTGTC CAAGGCAAGA AGATAGTAAA TTATAAGTAC AAGTGTAATA    3060

TGGACAGTAT CTAACTTGAA AAGATTTCAG GCGAAAAGAA TCTGGGGTTT GCCAGTCAGT    3120

TGCTCAAAAG GTCAATGAAA ACCAAATAGT GAAGCTATCA GAGAAGCTAA TAAATTATAG    3180

ACTGCTTGAA CAGTTGTGTC CAGATTAAGG GAGATAAATAG CTTTCCCACC CTACTTTGTG    3240

CAGGTCATAC CTCCCCAAAG TGTTTACCTA ATCAGTAGGT TCACAAACTC TTGGTCATTA    3300

TAGTATATGC CTAAAATGTA TGCACTTAGG AATGCTAAAA ATTTAAATAT GGTCTAAAGC    3360

AAATAAAAGC AAAGAGGAAA AACTTTGGAC ATCGTAAAGA CTAGAATAGT CTTTTAAAAA    3420

GAAAGCCAGT ATATTGGTTT GAAATATAGA GATGTGTCCC AATTTCAAGT ATTTTAATTG    3480

CACCTTAATG AAATTATCTA TTTTCTATAG ATTTTAGTAC TATTGAATGT ATTACTTTAC    3540

TGTTACCTGA ATTTATTATA AAGTGTTTTT GAATAAATAA TTCTAAAAGC AAAAAAAAAA    3600
```

(2) INFORMATION FOR SEQ ID NO:9:

(i) SEQUENCE CHARACTERISTICS:
        (A) LENGTH: 884 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 5'UTR
        (B) LOCATION: 1..884

(xi) SEQUENCE DESCRIPTION: SEQ ID NO:9:

```
TCCTCCTTTT AAACGCCCTG AATTGAACCC TGCCTCCTGC GCATCCTCTT TTTGTGTCAC      60

CTTAGGGTTC AGATTTAACT ACGCGACTTG ACTAGTCATC TTTTGATCTC TCTCTCGTAT     120

TTAGTACTTT TAGTCAGCGA GCATTTATTG ATATTTCAAC TTCAGCCTCG CGGTTAAGAG     180

CTTGGGCTCT GGAATCATAC GGCTGGAATT GGAATTCTGT CAGTCGTGTG GCCGCTCTCT     240

ACTGTCTTGT GAAGATAAGT GAGATAATCT TGACCTGTGG TGAGCACTCG TGAGCGTTAG     300

CTGCTGTATT TACCAGGTAC AGATAAGACA ACTACAGTGG ATGATAATGT ATGTGGTGAT     360

AGGGGAGTAC TCTGATGGTA GAGGAGTGAC TTTGGTTCTC TGCAAACTCA GCCTGAGACT     420

ATCAATTCAG TTTGTGGTGA GACCTCGCAG TGTTACCTTG GCAGATGGTA GAAGCCTTCC     480

AGATGGAAGG AAAAATGCGT GTAAAGGCAC AAAGTGTAGA AGGACCCTGA AGCTCCAGCG     540

TGAGGCCTGG CATTGAATGA AATATATTTT GTGGGTTTTC AGCTGCTGAA GTCATAGGAA     600

TGGATGAGAC CAAGAAAACA AAGCTGTTTT TGAGGTATGA GCGGAAGAAG AGATATCAGG     660

AGACTTTCGA AACAGTCATA ACGGAAGTTA ATATGATCAT TGCTAACATT TGCTGTGTTT     720

CAGGCACTGT AAGCATGTAT ATGGGTCCTT AAAGGGACTC ATAGAGAGGC ATACATCACA     780

ATTTGGAATT ATGCATTGGT TTATCAATTT ACTTGTTTAT TGTCACCCTG CTGCCCAGAT     840

ATGACTTCAT GAGGACAGTG ATGTGTGTTC TGAAATTGTG AACC                     884
```

(2) INFORMATION FOR SEQ ID NO:10:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
AGGTAGCTGC GTGGCTAACG GAGAAAAGAA GCCGTGGCCA CGGGAGGAGG CGAGAGGAGT      60

CGGGATCTGC GCTGCAGCCA CCGCCGCGGT TGATACTACT TTGACCTTCC GAGTGCAGTG     120
```

(2) INFORMATION FOR SEQ ID NO:11:

(i) SEQUENCE CHARACTERISTICS:
        (A) LENGTH: 35651 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
   (A) ORGANISM: Homo sapiens (xi) SEQUENCE DESCRIPTION: SEQ ID NO:11:

```
GATCTAGGAG ATGCAGGGAA TTGGGACTGA ATGCTAAGAA GGGATGAGGT TTCTTTTGGG     60
ATGATAAAAA AGTTCTGGGC TGGGCACGGT GGCTCACGCC TGTAATCCCA GCACTATGGG    120
AGGCCGATGC AGGAGGATCA CAAGGTCAGG AGTCTGAGAC TAGGCTGGCC AATATGGTGA    180
AACCCAGTCT CTACTAAAAA AACAAAAATT AGCTGGGCTT GGTGGCAGGC ACCTGTAGTC    240
CCAGCTACTC GGGAGGCTGA TGCAGGAGAA TCACTTGAAC CCGGGAAAGG GAGGTTGCAG    300
TGAGCGGAGA TTGTGCCACT GCACTCCAGC CTGGGTGACA GAGCAAGACT CCATCTCAAA    360
AAAATAAAAA TAAAATAAAA AAAGTTTCCA GAATTAGTGA TGATGGTTGT ACAACATAGT    420
AAAAATACTA AAAACCACTG AAATGTACAA CTCAAAATCG TGATTTTTAT GCTATGTGAA    480
CTCTAGCTTA ATTGCAAAAA AGAAACAGAC TGGGCTTGGT GGCTCATGCC TGTAATCCCA    540
GCACTTTGTA GAATACAGTC GAGTCGAATC GAATCATTAG GGTTAGGGTC ACCTTATTTC    600
CTAGAGACAA TCATTTAAGA ATGAAAAAGT TCATTGTTAG TTTTCAAATA TCTGCAAAAG    660
CATTAACTTT TAAGTTAAAA GGGTAATTCC AAATATTTCT GATAGTTTGA AAGGAATAGT    720
TGCATGTACA GAGTCATTTT ATAGGCTTTT TGTGAGAACA CAGGTTTTAA AAGCCCAAAA    780
TGCCCAGTTT AAAAAAAAAA TTAACAGGAA ATTTCTAAAT GTGACATGAC CTACTTACTG    840
TACCTGGTGA CAGATATCTG CCATCAATTC AATCAAATTT TCTTTGACGG CAATATTACG    900
AAATCCTGAA GAATACTTTC CTCTACTTCC TATATGACTT ATCTCATTCA CTAGCAGATC    960
ATATAAGTTG TATAAAATAC TTCTCCATTT TGTTGATTCA TAAGCACCTG TAATCCAAAA   1020
AATTAAAATG TAATTTTTAT GTATGTACTC TGTTTACACT GCTAGCTCCC ACAAAATTAT   1080
TCAGCTGTCA AGCTGCATCA GCGTTAGAAG ACACCTGGTC CAACCTTCCA TTCAGTACTA   1140
ATGCCTCTTC TGACAAGATC CTTGACAAAC TCTATTTCAT AACTGTCCAT TTTACATTTA   1200
GATAACTGTG TTTCTTATAA ATTTCTTCCA TATTCTGACC TAAAATCTGT CTTTCTCCAA   1260
TTTATTCTCC CACCTGAGGC AAATACAATT AATATGTTCC CTCTTTCATA TGAGGACCAA   1320
GTTCTCCGTA TGCCTTTTTC TGGCCTAAGA GAAAAATATT ACAAGTTCCT TCAACTAGTG   1380
TAAAAATGAC ATATTATTCA GACTTCTCAC CATTTCAGTC ATCTTTCCCA AGACACATTC   1440
CAGTCAACTT AAAATGCTGA CTATACAAAA TCTGGTGAAC ATGGTAATCC AACTGTGGCT   1500
TGACTAGTAT GCGAAACAAA AGGTCTATTA TTTCTCACAA ACAAGGTACT ACAAAATCTA   1560
TTAAAGTAGT CTGAAACTAC ATTAGCTTTT CTGGCATCCT CATCATCCTG CCAATTTTAA   1620
ATTCACCCTA AATATGCAGT TAACTAAATC CCTAAACATA TCATATCACC TCCTAATAAG   1680
CCTGATCTTC ATCCTGGAGA TAAGAGGTGA GTAAAAGATG AAAAACTATT AAAAGTCACT   1740
ATTCTTTCAC TTATAGTAGT TTCATGGGCT ACATATTATC TAGATATACT TATTAGAAGA   1800
GCCCATAAAA CAAATACACA GCTACTTTTG ATAAAAAGTG GCTACACGGC CGGGCACAGT   1860
GGCTCATGCC TGTAATCTCA GCACTTTGGG AGGCTGAGGC GGGTGGATGG TTTGAGGTCA   1920
GGAGCTCAAG GCCAGCTTGG CCAACATGGT GAGACCCCAT CCCTATTAAA ATACAAAAAT   1980
TAGCTGGGCA TGGTGCCGGG CATCTGTAAT CCCAGCTAAT CAGAACGCTG AGGCAGGAGA   2040
ATTGCTTGAA CCCAGGAGGC GGAGGTTGCA GTGAGCTAAC ATTGCGTCAC TGCACTTCAG   2100
```

-continued

```
CCTGGGCGAC AGAGTGAGAC TCTGTCTCAA AAAAAAAAAA AAAAAAAAAG TGGCTACAAG    2160

ACATTTCCTC CATTATAGCT GCTATTACTC AATGTGGTAT GCTGTTTTAA GAAAGTCACT    2220

ATACTAGCCA TGATGAGTTG GTCCAAAGGC TAGTATAAGC CCAAAGGCAA TCATAGACAG    2280

AGCAAGAGGA AACTCCAGTT CCAGCCAATA AAGTTCCTAA CTACAGAAAA GCACTATACC    2340

TTCTGGGCAA TACTCTCTTG GTATAGGACA TATATGAAGG AATTAAGGAG AATAAGTGAT    2400

TCTCCTTAAC AAGTGATACT CTAGGGCAAA CAGGGCCCTA GAGTAACTAT GAGGCTTAAG    2460

GCAGCAATTT CCCTGTTTCT GCCTCAAATT CCTATTAAAG TAATATGTAT GTATCTTCCT    2520

CAGGAGCTGA ATAATCTGAC TGGTTTTAGT CCAATTTACG TATTTTATCT TCTAATAAAA    2580

GTAACAGGTG GATAAACAAG ATCCTGCTTT CTTTAAATTC TTTTGCCCTA CAGTCTGTGT    2640

CAGACCCCTT AGTATCTAAG TATTGATGCA TAAGTAGCTC CTAGAGGGAA CAATGTCTCA    2700

GATTTTTTTG TATTTCCCAT AATACCTAAT ATTGTATTGA ACAAATAGAA AGGCATAACA    2760

GAATCTGCTA CCACTGCTTC AAATTCTAAA AACTCTATGA AAAACATTCT CATGGCTAAG    2820

TAACATTATC AACCAGAGAA ATCCAGAGGA AAGTCATATC CTCCTAAAGA ACACTAATTT    2880

TATACTTAGA CTTCTATGTT TGAATGAAGA AGCAAATTCA AAACAGTAAA CATTTCCTTT    2940

ATACCTTTTT CTTGGGTTTT GGCTCCTTTC GGATGATGGA TATAAATTTG CAGTTGAAAT    3000

AATTCAATAA TGACTTCTTT TAAAGAATCA TTAAGCCTAT GTTGAGTCCA AATATAAAGC    3060

AAAGTGGGAA GAATTTCATC TCCTAATTCA CACACTCGAA TTCGAAAGTT GACAGCCAAA    3120

GTCTTGAGGA AGATAGTAAG AGCTGCTAAG ATATGATTTA GACCTGAAGA GCTCTTTTCT    3180

TGTCTGTGAA GAAACAAACA AGCTCAACTG GGTATAACAG GGGGAACAAA CTGTACAAAC    3240

TGAACAGTTA TGAAGTGGTA TGCTGAAAGA AAAAAAAACA AAACCCTAAT TTTCAAACAG    3300

TAGTCTTAAT TTCAAAACTA TTCATTAAAA AAAAAATCAC AGCATTACTT CACACTGACA    3360

AAAAATTAGT TCTTATTTGG TGTTAAGAGA CCACTTCTGT TAGCTCTCCC TCCTGCTAAA    3420

ACATTGTATA AAAATAAACA AAACTGATTT GTAACACCAT TTATAAAATG TTTCACATTA    3480

TACATTGAGT ACTGCCATAC TAATGTACAA CAGTAATACT TCCAAAATAT TTTCCTATTT    3540

TATTTTATTC TCGGTATATT AAAACCATCC TCAAAATGGG GGAAATGCAA TGACTTAGAG    3600

GATATTTAAC TTTCCTGGTC AACAGAACAT CAGCAAGACA CATCTCCCCC TTGAAAACTT    3660

CACGTAGTGT TCTGCATATT GGATATTCAG AAAGTGTTGG ACTTGGTTGT CTCTTTAGGA    3720

ATCCACTAGT TCTGTTATGA TGGATCAATG TTTTATTTTA AGGTAGAATT TTTAGTTACT    3780

GAGTCTAAAA CATGGTCTTG CAAGATCAAA AGTATTTCAA TACAAAACAA AGAAAAAGA    3840

GATTAGATTA CCTCGCACAC TGAATAGCCT TGGAAAAAAA GTCCAAAAAT TTGGAATTTA    3900

ATCCGTCAGT CTGAGAACAG CATCCTTTGG TAACAGCATG AATTATTCTA GCCACTAAAA    3960

CTCTATGAAC ATCTTGTGAA GGTTTCAGAT AGAGCCTGAA GTACACAGAG AACAATTCTT    4020

AAAAAAAAAA AAAAATTATT AGTCATGATT TTTAAAAAT CAAATGTAT TAAATGTTAC     4080

AATTTAACTT AAATATTCCA TAATCCCATA CAGAAAAAGG ATTTTAAAAC TGCACTAATT    4140

TATTTTTAAC ATAGTAAAAG TACTCCATCA GTATTTAATT TTATCTTATA TAAAATGCCT    4200

TTAAGACAGG AATAACTATA AACTGCTGTG AGAGCACCAG TTTAAGAGCC AGGTCGCAGA    4260

AACATTACTT AACTTCTCTA AGCCTCTGTT CCATCATCTA GGCCTAAGAA AGCACTTACA    4320

GTACATGCTC CATGGGTTTT TCTTTCTTCT GTTTTTTGAG ACAGAATCTT GCTCTGTCGT    4380

CCAGGCTGGA GTGCAATGGT GCAATCTTGG CTCACTGCAA CCTCTGCCTC CTGGGTTCAA    4440

GTGATTCTCA TGCCTCAGTC TCCCAAGTAG CTGGGACCAC AGGCGCACAA AACCATGCCT    4500
```

```
GGCTAATTTT TGTACTGTTA GTAAAGATGG GGTTTCACCG TGTTGGTCAG GCTGGTCTCA      4560

AACTCCTGGC CTCAAGTGAT CTACCCACCT TGGTCTCCCA AAGTGCTGGG ATTATGGGCA      4620

TGAGCCACTG GGCCTGGCCT CCACAGTTTT TTAAAATAAT AATACTGTTT GATTAATAAT      4680

ATGCAAAAAA TGTGTTGAGA CCTATGAAGG GTATGAAATT TTACTCTGCT TGGTTTGTTT      4740

CTTATTTATT TGAGGTAGAG TCTTACTCTG TCACCCAAAC TGGTGTGTGG TGGTAAGATC      4800

ACGGCTCACT GTAGCTTCAA TCTCAGCAGA CTCAGGTAAT CCTCCCACCT TAGCCTCCCA      4860

AGTAGCTGGG TCTAGAGGCC CACACCACCA CACCCAACTG ATTGGTATTT TAGGTAGAGA      4920

CAGGATTTCA CCATGTTGCC CAGGCTGGTC TTGAACTCCT GGGCTCAAGT GATCCACCTG      4980

CTTTGGCCTC CCAAAGTGCT AGGATTACAC GCATAAGCCA CTGTGCCTGG CTGAGATTTT      5040

ATCTACTTGT AACCTAACAA ATTAGCATGA CAGTTTCCTG GGTGCTAGCA GGAAACCTGA      5100

GATTCCTGAT AAGAGAAAAA GGACAGTTTA TTTCTCCCAG TAATGATGGT AGCCAGACTA      5160

CCTTCATTTT TGCATCAGTT CCCCAGTACC AAAGGCAAGG TGAAATGGGA CACTTGACAC      5220

TGCGAAAACA GTGGACTGAG TTATAACAGA GAAACCTCAA GCTTTTTATA ATCAATAGGC      5280

TACAAGTAAA TCTGTCCTGT TTTAGAGGAA GCCATCATCT GACCTTAGAT GATCCACCTG      5340

CCTCAGCCTC CGAAAGTGCT GAGATCACAG GTGTAAGCCA CTGTGCCCAG TCCCAAATA      5400

ACATTATTCA CAATGTTATA CTTGTGTATA TTGGGACTTT ATATATAGAC AATCATGTCA      5460

TCTACAAAGG GGAGTGTTAT TTCTTCCTTT CCAATCTGTA TGCCTTTTAT TTTTCTTGTC      5520

TAACTACCCT GGCTAGAACC TCCAACATAA TGTTGAAAAG GAGTGGTGAG AGTGCACATC      5580

CTTATCTTGT TCCCAATTTG TCTTATGAAA GGCTTTAAAT TATGGATTCA ATTTATTCTC      5640

CTAATAGTTA TGGGACTAGT CAAATTATCT ATTTTATATT GGATGACTTT TGATAATGTA      5700

TGGTTTTGAG GAACTGGCCC ATTTAAATTA ATAGATGTTC ATAGTGTTTC CTTATTATCC      5760

TTTGAATATC TATAGGATCT GCAATTAGAT CTCATTTCAT TTCTAATATC AGTAACTTTG      5820

GTCCTCTTTT TTTTGTTTTT TGTTTTTTTA AGAGACGGAA GTCTCACTAC ACTGCCCAGG      5880

CTAGATTTGG ACTCCTGGGC TCAAGTGATC CTCCCACTTC AGCCTATCAA GCCATAAAAA      5940

GACATCGAGG AGCTGAGAAC GGTGGTTCAC ACCTGTAATC CCAACACTTT GGGAGGCTGA      6000

GTTCAAGCTG CTGGCATAAG CAACATAATA AGACCTTATC TCTACTAAAA ATGAAAAATT      6060

AGCAGGGTGT GATGGCTTGT GTCTGTGGTC ACAGCTACTT GGAAGGGGGT GGGAGGATCA      6120

TTTGAGCTCA GGAGGTCGAA GCTGCAGAGC CATGATCTCA CCACCACACT CCAGCCTGGG      6180

TGACAGAGTG AGGCCCTATC TCAAAAAAAA AAAAAAAAAA AAAAAGAAA GAAAGACAGA      6240

AGAAAGAAA GAGAAAGACA TGGAGGAACC TTAAATGCAT ATTACTAAAT GAAAGAAGGC      6300

AATCTGAAAA TGATACATAC TGTTATGATT CCAACCACAG TCACATACTA CATAACAACA      6360

TTCTATTCAA TGACAAATGG CAATATGAAA AGGTGGTACC GTAAGATTGT ATCAGAACTG      6420

AAAAATTCCT ATTTAAATAC TTAGTGATGT CATAGCACAA GAAATTACTC ACAAGCATTT      6480

GTGGTGATAC TTGTGTAAAA AAACCCACT GCACTGCCAG TCATATAAAA GTATAATACA      6540

TACAATCATG TATAGTACAT AAACCTTGAT AATGATAATA AATGACTAAG TTACTGGTAA      6600

AATGTTAGGT TTATGTACTT ACTCTACTAT GCTTTTTATC ACCATTTTAT ACTATATTCC      6660

TCCTTCTTCT TCTTAAAAAA CAAAACAAAA CAAAACAGTA AACAGTCTC AGGTAGGTCC      6720

TTTAGGAGGT ATTTCAGAAT AAAGCACCAT TATCATAGGA GATGAAAGCT CTGTGCATGT      6780

CCCTGAAGAT CTCCCAGGGG GACAAGATGC AGGGACAGAA GACAGTGATA CTGATGATCC      6840
```

```
TGACCTTATG TAGGCCTAAG CTCATGTGTG TGTTTGTGTC TTTGTTTTCA ACAAAAAAGT    6900

TTAAAGGAAA AAATAGAGTA ATAATAATTT CATTTAAAAA GCTTATAGAA CAAAAGAAAA    6960

AACATCTATA AGTATATAAG GAAAAAATAT TTTTGTACAG CTGTACAATG CATTTGTATT    7020

TTAAGCTAAG TGTTATTACA AAAGAGTCAA AAAGTTTAAA CATTTTTAAA GTTTATAAAG    7080

TAAAAAAGTT ATAGTAGCTA ATGTTACTTT AGTATTGAAG AAAGAAAAAC ATAAATTTTT    7140

AAATTTGGTA CAGAATAAGA GTTTACAAAT TCTACAGTAG TATATAGTAT CCCAGGCCTT    7200

TACATTACCA CACATTTACA TACCCAGAGC AACTTCCAGT CCTGCAAGCT CCATTCATGG    7260

TAAGTGCCCT AGACAGGTGT ACCATGTTTT ATCCTTTATA CTATACTTTT ACTGTACCTC    7320

CTCTATGTTT ATATATGTTT AGAGACACAA ATACTTGCCA TTGTGTTACA GCTGCCTACA    7380

GTATTCAGTA TAGTAACATG CTGCACAGGT TTGTAGTGCA GGAGCAGTAA TACCATATAG    7440

CTTAGGTGCG TAGTGTTATA CCATCTAAGT TTGTATAAAT ACACCCTATG ACGTTCACGC    7500

AACAAAGAAA TTGCCTAATG ATGTATTTCT CAGAACATAT CCACATTGTT AAGAGACGCA    7560

CAACTGTATA TGACATGCTG GAAAAGGCTA AACCATGGAG ATAGCAAAAA GATCCATGGT    7620

TCCCACAGTT TACAAGAAGG AAGAGATGAA AAGGTGAAGC ACAGAGGATT TTTCTGACAG    7680

TGAAAGTATT CTGTATGATT CTGTAATAGT GAAAAATTGT TACCATTCTC TCCCAGAGGA    7740

AAAAAAAATA TGACCATCTC ATTAGATACA GAAAAAGATC TTTAAAAATG TCAAAACACT    7800

TGTCAAAATC CATAGCATAT GTACCACCAA AAGTGAACCT TGGACTCTGG ATAATAATGA    7860

TGTGTCCCAG CATAGGTTTA CTGATGGTAA CAAATGTACC ACTGGTGCAA GATGTTGACA    7920

GTAGGGCATG CTGTGTGTGT CCAGTGGACT TTCCACTCCG TTTTGCTGTA AATTTAAAAT    7980

TCCTCTAAAA GATAAAAGTC AATTTAAAAA AATGGAAACC ACTAGGTTTG AGAAACTGAA    8040

TAATTGACAG TGTAGCTTGA GCACAGAAAT TAGAAGCGCT TTAGTTAAGT TAGACAGGTA    8100

GGAAGAAGCA AAATTATGCA GCACTTTCAA GGCCTAGAAG AGGAATCCTC ATTTTCTATT    8160

AGTTGTGCTA GTGAGAATGT AGAGAAACTG GAACCCTTGT GGGCTGCTGG TGAGAATGTA    8220

AAATGGCGTA GCTCCTGTGT AAAACAGGAT GTTGGTTCCT TAAAAAATTA AATATAGAAT    8280

TACCACATGA TCTAGCAATT CTACTTCTGG GTATATAATC AAAAGACTGA AGCAGGAAA     8340

CTCAGGAGAT GTATACTCAT GTTCACGGCA GCATTATTCA CAATAATCAG AAGGTAGAAA    8400

CAACCCATGT CCACCAATGG ACGAATGAAT TAACAAAATG TGGCATATAC ACAGAACAGA    8460

ATAGTGTTCA GTTTTTAATA AGGGTGAAAT TCTGACAAAA GCTGTAACAC TGATGAGCCT    8520

CAAAGACATT TTGGTAAGTG TAATAAGCAG GTTGCAAAAG GACAAATACT TATAGGAGTC    8580

CTCTACTTCA GGCTGCTATA ACAAAGTATT ATAGGTTAGG TGGCTTAGAA ACCACAGAAA    8640

TTTATTTCTC TCAATTTTGG AGGCTGAAAG CAGCTCAGGT GCCAGCATTG TGGGTTTCTG    8700

GTGAGGGCCC TCTTTGGGGC TGCAGACTAC TGACTTTGAA CTGTATCTTC ACATGGCAGA    8760

AAGACAGCAA GTTAGCTCTC TGGCCTCTTT TCATAAGGGC ATTAATCCCA TCCATGAAGG    8820

CTGGACCCAC AGGACCTAAT TACCTCCTAA ATCCCACACC TCCAAATACC ATCCCTTTGG    8880

GAGTTAGATT TCAACATAAT TGGTGGGACA CAACATTCAA TCCATAAAAA TGAAGTACCC    8940

CAAATAGCCA AATTCATAGA GAGAGAAAGT AGAATGGTAG CTGCCAGGGG ATAGGGGAGG    9000

GGAAAATGGT AAATCATTGT TTACTGAGTA TAGAAAAAAA AGTTCTGGAG ATGGATGGTG    9060

GAGATGATTA CACAACAATA TGAATGCACT TAATACTACA CAACTGTACA CTTAAAAAAG    9120

TTAAAATTAT AAATGTTATA TATATTTTAC CACAATAAAT CACACTGGAG GTCCTAGCCA    9180

ATGTAATAAA GCACAAAAAT AAAATAAAAG CCACATGGCT CAGAAAGAAA GAAAAAAAA     9240
```

-continued

```
TTACTGCTTA CAGAAGACAT GTTTGTCTAC AAAGAAAATC CAAAAGAACA TTCAAAGAAA      9300

GCTACTAGAT TTAGTAAGTG ATTTTAGCAA GGTCCCAAAA TACAAGGTCA CTATACAAAA      9360

ATTAACTGGA CTTCTGTATA ATTTTTGTGC ATTGAACAAT TTGAAAATCA AAATGTTAAA      9420

AACAATGCAA TTACAAACTA CTGCAGTATA AATCTAACAA ACATATACA AAATCTTTAT       9480

GTTTATACAA TTATAAATAA ATGTCAATTT GCAGCTGGGC ATGTTGGCTC ATGCCTATAA      9540

TCCCAACACT TTGGGAGGTC AAGGGAAGGG TATCACTTGA GCCCAGGAGT TTGAGACCAG      9600

CCTAGGCAAC ACAGTGAGAT CCTGTCTCTA TTTTTTTTAA TATATAAAAT TAAAGAAAAA      9660

AATTGTCAAT TTACAACAAA AAATCTATAT GCTGACAATT ATAAAACACT AATGAAAGAA      9720

ATCAAAAAAG ACAAGTGGCC AGACGCGGTG GCTCAAGTCT ATAAACCCAG CACTTTGGGA      9780

GGCTGAGGCA GGTGGATCAC CTGAGGTCAG GAATTCGAGA CCAGCCTGGC CAACATGAGG      9840

AAACCCTGTC TCTACTAAAA ATACAAAAAT TAGCTGGGTG TGGTGGCACA TGCCTGTAAT      9900

CCCAGCTACT CAGGAGGCTG AGGCAGGAGA ATCGCTTGAA CCTAGGAGGT GGAGGTTGCA      9960

GTGAGGTGAG ATCGTGCCAC TGCACTCCAG CCTGGGCAAC AGAGGAGAC TCTGTCTCAA      10020

AAAAACAAAC AAAGAAGCAA AAAAAAAAA AAAAAAACC TAAGTAAATG GAGAGATATA      10080

CAGTGTTCAT GGATTGGAAA ACTCCACATT GTTAAGATTT CTATTCTTCT CAAATTGTGC      10140

AACAGATTCA ATGCAATTAG TATCAAAATC CCAGCAAGAT CTTTTGTAGA AATCAGTAAG      10200

CTGATTCCAA AATTTATATG CAAATGCTGA CTCAATCTTA GGCCATTCTT CTCATCTCAC      10260

ACTAAACTCT ATATACAAAT CTCATCCATA GTCATGGCTT CAGTCACCAC CTGTACCAAA      10320

TATATATTTT GAGCACAGAC TTCGCTTCTT CCACAGAGTC CTCATCTAAG CAAGTTTTAA      10380

AAGGAAGCTA AGTAAAAAAA TACTTTGACA AAAAAGCTAA TTATAAGAAG TAACATCCGG      10440

GAAGAAGTGG CAAAGGTTAG CTTAAATAAA AGAAAAAAG AAAAAAAAAG AAGTAAGAGT      10500

AGTTAGTTTA AAAATAAAAA GGGGGTTTCA GAGAACAAAC TAGATGACAG AATATAGTAA      10560

GCAGACTAGG GGAAAGACTG CCTTTGTTTC AGTGACAGCC ATGGTTGTAA GTGATAATGT      10620

AAAATGACCT AAATATGACC AGCCATACTG GGGAAAGATC TGGTTAGGTA ACCTAGATAT      10680

CACCAGCCTA TTCCCAAAGG CTGTCTCTAG GCTTGTTGAG GGCCCTGTTA CAGACACAGC      10740

CTATCTTGTG TTCAGAGTAA CGTAAAGGCT ACAAATGACT CCTAAGAAAT TAGCTGAGAA      10800

GGCATTTATT CTCAGGGGAA CAGTAGAGTG TAATGCAGGA GTGAGGGTAC TGATTAGGTA      10860

GTAGTTTTGT GGTTCACATG TATCTCATTT TGAAATAATA AAATGGCAAT AAAGAATATG      10920

GACAAATGTC TTTTAATTTA GCTAGCAAAA TTTAGCTTAA ATACTTTCCA TGAAAAAAAA      10980

AAGCTTCTAA ACTTTTAGAG TTCGTGTATT AGAAGACTTT GACATCTGAC TTAAAATCAT      11040

CTTGTTAATG TCAAATCCTA CTTTCACTTA TTCTCAAACC CAGAAATGCT CCATCTTTGA      11100

AACCAACAAA CTGAAGTATT TCAATCTCTG ACCATAACTT CCTTCCTTTG TGGTCTCTCA      11160

GTACCTCCCA GCTATAAACA GGAAACACCA CCAGATTCCT CCCTAGCACA CACTCTACAC      11220

ATCTAATGAA TCACTGGGTT CTGTACATTG TCTTCTAATG CATTCTATTC TAATATATTT      11280

GATTTCCATT ACCTTAGAAG TAGCGTGCTA ACTGCCTCAT CCAATGGATA CTTTTGTGTC      11340

TTATCCTTTC TACAACACTT AAAATGTTGG CCACGCCCCT TTGAACTTTC AACTCTCTTG      11400

CTTTCACTTT TTTTTTTTTT TTTAAATGG AAACAGGGTC TCACTCTGTC ATGGAGGCCG      11460

GAGTGCAGTG TGATCACAGC TCACTGCAGC CTTAACCTCC AGGGCTCAGG TGATCCTCCT      11520

GCCTCAGCCT CCCAAGTAAC TGGGACTACA AGCAAGAGCC ATTACCTCCG CTATTTTTTT      11580
```

```
AAAGACAGAG TTTCACCATG TTGCCCAGGC TGGTCTTGAA CTCCTGAGCT CAAGCAATCC    11640

ACCGGCCTTG GCCTCCCAAA GTGCTAGGAT TACAGGTGTG AGCCACTGCA CCCTGCCTGC    11700

TTTCACTTTT ATGGTACTTC CCTCTCTTGG TTTTCTCCCT TTCTACTTAA ATCATGGTTG    11760

AGTTTAGGTG TCATTGTTTT GTATACCTAC TGAACCCAAA TATGTCTGTA TCACAGCACA    11820

TTATGAACTC TGGTTTACTT GGGTTTTCTT CTGCCACTGT CAACTCCTTG ACGATGGAGA    11880

TGGTATTTTT CAACTGTAAT TCCAGCTCTG ATATCAGGCA CCTGATATAT TATTCATGAC    11940

TTTATTCAAA AGCTACATAA TAAATAAAAA TTAAGGGTCA GTTCGATAAC CATATAATTT    12000

TACTAAAGTA CTGTTAAACT GTCAGGTCAC TTGGGGGATA TAGACAGATA CAGACAGAGT    12060

GCTTTCTTTG GTGAAGTTTC ATTTCATGAG GAAAAATTCA CAAACAACAA CCTTCAAAAC    12120

ATACCTAACC ACTGTTGCTG AGATATTTCA CACCAGTATT TTCTCACAGA AAGAATGTCT    12180

TTGAGTAGTA TGTTGCTACA ATCAGCTCCG TAAATAGCAC CATTAGATGA ATCTTTCACT    12240

GTATCCATGA TATAATTTAA GAGTTCTTGA CATTTTAGCC TAGGTGCTCC TATTTCAAAA    12300

TAAACAAATA AAGAAAAACA TAAATTTGAA CAAAAATAAG ACACTTGGAA TGGCAACTAT    12360

TTAAATAATT CCATTTGGGA AATTACTATT AACTAAACTT CTTTTGTAGA GAAGAAATTG    12420

GCAAATTATG GCCCCAAGCA AAATTCATTT TTTTTTTCTT TGCAAATAAC ATTTTATTGG    12480

AACATAGTCA CAACCATTCA TTTACTTATT GTTTATGGCT GCTTTTGTAA TTAAGACAGA    12540

GGTGACCACA TGGCCTATAA AGTCAAGAAC ATTTACTATC TGGCCTCTTT ACACAGTAAG    12600

TTTGCCAACG CCTCTTTTAT AGGAATATAT AGCAAAAACA ATCATTCTTT TTTTTTTTTT    12660

TTTGAGATGG AATCTTGGTC TGTCACCCAG GCTGGAGTGC AGTGGCACAA ACTCAGCACA    12720

CTGCAGCCTC CACCTCCTGG GTTCAAGTAA TTCTCCCGCC TCAGCCTCCA AGTAGCTGAG    12780

ACTAGAGGCG TGCACCACCA CACCCTGCTA ATTTTTCTAC TTTTAGTAGA GACAGGGTTT    12840

CACCATGTTG ACCAGGCTGG TCTTGAACTC CTGACCTCAA GTGATCTGCT CATCTCGAAA    12900

AGCAATCATT CTTAAACAAT TATAACCTTA ATAATTCACA ATTTCTGGTG TTAGACCAAA    12960

AATGATCCCA AGTTTTTTGG CACTCTTTAT GAAGAATGAA TTTATTAGAA TAACATAAGA    13020

TTACAAGGAG AATATTTACC TTGGAAAGCA AAATTAGTTC TAAGTCCTAT AATAGCATTT    13080

ATGGCATACA AATACCTCAG GTTGTAATTT TTTTTTTTTA AGACAGGGTC TCGCTCTATC    13140

ACCCAGGCTG GTGTGCAGTG GCATGATCAC ACCCAACAGC AGCCTCAACC TCTCAGGCTC    13200

AAGGGATCCT CCCACCTTAG CCTCCTGAGC AACTGGGACT ATAGATGTTG TGCCACCATG    13260

CCCAGCTAAT TTTTTAAATT TTTCATAGAG ACAGAATCTC TCACAATGTT CCCCAGGCTG    13320

GTCTTGAACT CCTGAGCTCA AGGGATTCTC CTGTCTTGGC CTCCCAAAGT GCTGAGACTA    13380

TAGGTATGAG CCACTGTGCT TGACCCCTGT ACCTGTGTCA TTTTTAACAG CATGTTATTT    13440

ACTTACTAGA GATTCTGAAA ACTTGGCATG ACTACACACA TATTCTTGAA GGTAACAAAA    13500

TTACATTTAA AAATAATTTA ATTATCATTT TCAGTAAATT ATATTTACGT CACAGCAGAA    13560

ATGCCATTTT TCCATACTGA CAATCTTAAA ATTGAATATA TTTATTGCCA TAACTATGAG    13620

CAGAACACAA CTCATGTAAA TATGAATATA TTCTGGATTA GGGTTTTCCT ATGATGAAAC    13680

TAGTTATATT CACAGGCTAT GGTAAACAAA TATACACTGA TATAACTGCA AAATCATCTT    13740

CACTTATGGC TCACTTCATA ATTTTAGGCA TTGTCCAGTT ATGAAATGCA CAACCATGTG    13800

ATCCTTTTTT CTAGTACCCT GTGCATTTCT CTTATAGTCC TTGTAACATT TTTCTAATCT    13860

AAAACATCCA TTGTATGATT AGATCCTTAA GGAAAGGAAT TAATCTCTAT ATTCTGACGT    13920

AAAAGCCCAG TGACTGCCCT AATAGCAAAT GCTCAATAAA AATTAATTTG TGTTGAATAA    13980
```

-continued

```
CTACAGAAAT TAATATTATA ATAAAATCCT ATCTTCCTAT GTCCTTTATC CCAATATATC    14040

TCCCTCCTCT ACCAAATATG AGAAGTATTT CAAGAAATGT TGACTTTTTT TCATAGTTTT    14100

GCTTGTTTTT GAGACAGAAT ATCTCGCTCT GTCACCCAAG CTGGAGTGCA GTGGCCCCAT    14160

CATGACTCAC TGCAGCCTTG ACCTCCTGGA CTTAAGGGAT CTACCCATGT CAGCCTCCCA    14220

GGTAGCTAGG ACTACAGGCA AGCACCACTA CACTCAGCTA ATTTTTTTAG TTTTTTTAAA    14280

GATGGGGTCT CCCTATGTTG CCCAGGTTGG TCTCAAACTT CTGGGATCAA ATCTTTCTTA    14340

AAAGTACAAC TAAGTTGCCT GCAGAGACTT TTTTTTTTTT TTTTTTTTTG GACACAGGAT    14400

CTCACTCTGT CACCCAGACT GGAGTGCAAT AGCATGATCG TGGCTCACTG CAACCACTGC    14460

CCCCTGGGCT CAAGCAATCT TCCTCCCTAA GCCTCCTAAG TAGCTGGGAC TACAGGTGGT    14520

CACCACCACA CCTGGCTAAT TTTTGTGTTT TTGTAGAGAT GAGGTCTCAC CATGTTACCC    14580

AGGCTGGTCT CAAAATCCTG TGCTCAAGCA ATCTGCCTGC CTTGGCCTCA CAAAGTACTA    14640

GGATTAGAGA GGCATGAGCC ACTGTGCCCA GCCTACTTAC AGAGACTTTC AGGAATCTTA    14700

TGGAACTTAA CATTTTTCGC AGCTGAGTTT TGCACTATCT AGACTCTATT TAAGCTTTGT    14760

ACAAAAGCAG ACAAATGCTA ACATAAAGAA ATGAACAGGG TGGGCACAGT GGCTCACGCC    14820

TATAAACCCA GCAGTTTGGG ATGACAAGGC AGGTGGATCA CTTGAGGTCA GGAGTTCGAG    14880

ACAAGCCTGA CCAATGTGGT GAAACCCCGT CTCTACTAAA AATACAAAAT TAGCTGGGCA    14940

TGGTGGGGCA TGCCTGTAAT CCCAGTTACT TGGGAAGCTG AGGCGGGAGA ATCGCTTGAG    15000

CCCGGGAGGC GGAGGTTGCA GTGAGCCAAG ATGGCGCCAT TGCACTCTAG CCTGAGCAAC    15060

AAGAGCAAAA CTCTGTCTCA AAAAAAAAAA AAGAAAAGAA ATGAACAGTA GGCTGGGTGT    15120

GTGAGTGTGG TGGCTCACAC CTATAATCCC AGCATATTGG AAGGCAGAGG CAGGCAGATC    15180

ACTTGAGGCC AGGAGTTTGA GACCAGCCTG GCCAACATGG CAAAACCCTC GTCTCTACTA    15240

AAAATACAAA AATTAACCGG GCCTGGCGGC GTGTGCCTAT AGTCCCAGCT ACTCTAGAGG    15300

CTGACACGTG AGAATCGCTT GCGCCCAGGA AGAAGAGGCT GCAGTGAGCC AAGACTGCAC    15360

CACTGCACTC CAGCCTAGGC AACAAAGCAA GACTCTGTCT CAAAAAAAAA AAAAAAAAA    15420

AAAAAAAGGA GAGAAATCAA CAATATTTGC TTACTTGTTT CTTCTCAGCT GCCTTTTACT    15480

TCTTTTTTAC TAATCTCTAT TTCTTTCATC ATACCTTGGA TACCAATGCT AAGCAAGAAT    15540

GGCAAAGTTT AGACATATGT TAAATTTCCA TCAACCCTCC AATCTTTTCG TAAAAAACAA    15600

ACAAACAAAC AAACAAAAAC AACTGAAGTG GGGTGAGGGA ATAGTAACTC CCTGGTTTTG    15660

CCCCAATATT AAAAAGGTTT AAGTAACAAA GTCAAATTTG AAAGAAAAGG AAGCCGTAAA    15720

TAAAAAAACA AATTTTCAAC TACTTACATG ACCAGCATTG ATAATTTCAC CAACTATTTC    15780

TTATAAACCA ACAGGCTGAT GCATTTTCAA ACGTAATCTC CATTGTTAAT GTTGCAATTA    15840

AAAGGTTTGT TCACTGCAAG GCAAAACTAC TGTACACATT GCAAACTTTT CTGGTGGGCT    15900

ACAAAATTGA CATGTTATCT TTCTCTCATT CACTCTTTCA GTAAGTACCT ACTATATCCC    15960

AGCATTATTA GCAAATAAAA TATTTTACTG GATACAAAGC TACTACACAG AGCAAAAGTG    16020

AGTGCAGAAT ATTTTGGTGT AGTTTTCCTT TGTCTCTGCT GGAGTCTCTG ACAAGGGGTT    16080

GAAGCTATCC ACACGAACTC GCATCTCAGA GGAGGTAGAA AATTGACTAA ACCATTATTC    16140

TTTGGACTCA AGTCTCATAC CACCAATCTG AAATATTCAC TAATAATCTG CATACTTCTA    16200

CTAAATATTT ACCAATTTGG GGGCTTTCCT GATTCTTTTT TTTTTTTTT TTTTTTTTG    16260

AGACAGAGTT TCACTCTTGT TGCCCAGGCT GGAGTGCAAT GGCACAATCT CAGCTCACTG    16320
```

```
CAACCTCCAC CTTCCAGGTT CAAGCAATTC TCCTGCCTCA GCTTCTCGAG AAGCTGGGAT   16380

TACAGGCACC CGCCACCACA CCCAGCTATT TTTTGTACTT TTAGTAGAGA TGGGGTTTCG   16440

CTATATTGGC CAGGCTGGTC TCGAACTCCT GACCTCAGGT GATCTGCCCG CCTCAGCTTC   16500

CCAAAGTGCT GGGATTACAG GTGTGAGCAA CCGCGCCTCA CACTCCTGAT TCTTAAATTA   16560

AGAGTTGGTA TCACAAAGCA ACATCCTTAT CTGTGAAGAG CCCAGGAGTC CCTGAACACA   16620

CACTTCTGCC TCTAGCTTTT CAGTATGTGT AAAGCCCATT TCCTTACAAA AGCTTGCCAG   16680

GATCCTGCAT TTTGGTTCCG AAAAATCAAC TCTTCACAAT ATTAATTGTA CAAGTTAAAG   16740

ATGGGAACTA TTTGGCTCAT CAGAAGAAAA AAATATTTTT GGGGGTTGTT TTTTTCCTCA   16800

AATCATAGCA AGTAAAATGT CAGTTAAGTG TTGGTTCTGA CAGCCAAGGA AGCTCACATG   16860

ATCTTAGAAT TAATCAGTAA GAGTACAGAA TGAAAGATAA GCAAGAATTG CTTCACTCTG   16920

TACTAATCAG AATATACCTA AAAGATTGAG TCCTGGCCAG GTGCAAGTGG CTCACGCTTG   16980

TAATCCCAGC ATTTCAGGAG GCCAAGGCGG GAAAATCACT TGAGGTCAGG AGTTTGAGAC   17040

TAGCCTGGCC AACACAGTGA AACCCTGTCT CTATTAAAAA TACAAAAATT AGCCAGACAT   17100

GGTGGCCCAT GCCTATAGTC CCAGCTACTT GGGAGGCTGA GGCAGGAGGA TCACCTGAGC   17160

CTGGGAGGCG GAGGCTGCAG TGAGCCAAGA TCGCACCACT GCATGCACTC CAGCCTGGGC   17220

TACAGAGCAA GAGCCTGTAT TAAAAAAAAT GAGTCCCACA CTTTTTTGTT TGTTTTTCTG   17280

GCCTCTTCCC TGTAAGTAGA GGCCCACACT TTAAGACAGA CAATTAAAGT GAAGAATATT   17340

CAGAGGAGAG TAGCATAAAA CCTAGGTCAC GTGAGCTGAA GAAAGTGAGA TTATGAACTT   17400

TAGAGATGAG GACTTAGGAA ATATTGTGGC TACTTTCAAA CATCTCTAAG GATGTCACAC   17460

TAAAAACATA AATAGGAGTT TTTGATATAC TCTCAGAAGG GAGAAGCAGT AACAAAAGAC   17520

AGGTTTTTAA TACTTTTCTT TTTTTGACAG TCTCGCTCTG TCGCCCAGGA TGGAGTGTAG   17580

TGGCGTAATC TCAGCTCACC ACAACCTCTG CCTCCTGGGT TCAAGCAATT CTAGTGCCTC   17640

AGCCTCCCAA GTAGCTGGAA TTACAAGCGT GCGCCACAAT GCCCAATTAA TTTTTGTATT   17700

TTTAGTAGAG ACGGGGTTTT GCCATGTTGG TCAGGCTGGT CTCGATCTCC TGACCTCAGG   17760

TGATCTGCCT GCCTTGGCCT CCCAAAGTGC TGGGATTACA GGAATGAGCC ACTGCGCCTG   17820

GCCAGTTTTT AATACTGTTA ATGCTATTCA AAGATGAAA AGAAAGCCTT GAAAGTATAT   17880

TCAATCATGA AGACTGCACT TCTACCTAAA GGCTAGGGAC GTAGAGAGGG CATCCAAGAC   17940

TGGGTAGTTA AAACAGTAAT TTTTAATTCC TTCACTGGGC ATGGTGGCTC ACATCTGTAA   18000

TACCAATAAC TAGGGAGGCT GAGCAGGGGG AGGACTGCTT GAGGCCAGGA GTTCAAGATC   18060

AGCCTGGGCA GAACAGTGAA ATAACACCTC TTAAAAAAAA AAAAAAAAAT CAGCCTGGCA   18120

TGGTGATGCA CTTCTGTAGT CCTAGCTACT AGGAAGCCAA GACAGGAGGA TCACTTAGGA   18180

ACAGAGAAGC TTCAGCCTGC AGTGAGCTAT CATCACACCA TTGCACTCCA GCCTGGGTGA   18240

CAGAGTGACA CCCTATCTCT TAAATAAATA AATCCCTTCA ATCCTCAGAT TTCTGTCATT   18300

CTATGCTTGC ATAAATTTCC CCAAATATTT GAACTTGTAA TATTAAAAAT CAGGCTGGCC   18360

TGAGTGCAGT GGTGTTTACA ACGAATTGAT CACAACCAGT TACAGATTTC TTTGTTCCTT   18420

CTAAACTCCC ACTGCTTCAC TTGACTAGCC CTAAAAAAAA ACCTTTTAAT AAAAATAAAA   18480

ATCATTATAT GTACTTACAC TCAACTTTTA TCTTATTCTA TTTAGAACAA ACTTATGCAA   18540

CAGTTAAGTC CTTAAAATGA TCTGAAAAAA AAAAAAAAAC TCACGCGACA GTAATCTGTT   18600

AAGCCATTTA TTTATAATTT ATAACATCAC TTACTTCTGT TTGCACATTT GATGAAGTAT   18660

TTGACCAAAC TACTGATTTC CTGCATCTTT TTCTGCCTGG AGGCTTGTGT TGAGGCTGAT   18720
```

```
ACATTTGGTT TTGCTATTCT CAGACATTCT GTTTCTTTCT GAATATATTT CTGTAAAAAT    18780

CTTCAAGAAA ACAAAATGCA ATTTCAGAAA CTCGTTGAAT ACTTAAATTA TAATAATTTC    18840

AAAAGCTGTT CATGCCATCA CAAAGAGCAA CTTTTAAACC ACCTTGCTTA GATTACTACA    18900

TCAGCTGAAA AAAACAAATA AAACAATTAA ATCTCTCTTT CAAGGCCTAA CTCCTACAAG    18960

ACCAATTTAA TATCTGGTCT GCAAAGCTCT TAATCTTCTA TGACTTTCTA TTGCTTTACT    19020

GCCTGTTTTC TAAATTTGTC ATTAAAAGCT TACAATGCTA GTAAGGACCC TCTCAATCCT    19080

CTCTCAACTC CTTCTGTTAT TCTGTACAGG ATCTACCTGT TTCTTAGGCA GTTGGTAATG    19140

TTGCCAGCCA ATAAATTAAG CCTGCCTAGA AGATATTCAT AACTAGCCAG GAATGCTGGG    19200

TGCATATTTG ACCTACCAGA TCAGCTTATA CAAAATAGTA TTCATCTTCA GGTTGTAATT    19260

ATATTTGTGG TATTTAAAAT AAACTAGAAA ATCAGAGGAA AAACAGCATG CATGTTTCAT    19320

TTTATATGCT TTCAAATCTG TAACAGTCAA TCTAATACCA AACAGGAGCT AAAAATAAAA    19380

CAGAATCTGT CATAAACACT GAAGGACAAC TAAATACACA CTTCCTCTTG ACTACAAATG    19440

TTATTTCTAG TTTATTTAAT ACTCTCAGTA TTTAAAATAC TTTATTCATC TTTCCTAATC    19500

CTTACAATCT GTTTCTAGTT ATAAATGGAT TTCACGGTTG AAAATGATGT CTCAATGTAA    19560

AAATGCATCA ACCCTGTTTG CCACTCCTGT CCAGCAATCA GTTGTGTTTT TTCATTGTTC    19620

GAGGTATTTT TTGTTTTTAA CCAAATTCAT ACACAAGTAT TCCAATCTTC CTTTTACTTG    19680

TTTTATTACA ATTAACACA CAGCATTTAC TTATAATCAG AGTAATATTT AAAGGTGTGA    19740

AAATAATATC CTAACATTTA TTATAATTTT TTCCTCTAAT CTGAAGTCTT GTGAACTAAC    19800

TAAAATGAAA GAAATTCTCT CTCAATTTTG AGTGAGATAT GTCTAAAACA TTTTATTGAA    19860

GAAATAATTT ATAATTTTTA AGTTCTATA TGAACAACCT TTAAAAATTA TGTTTTGGAT    19920

AAATATTAAA TGCCAAATTC ATATGCAAGG CATAATGATA TATAGGAAGC AAAGATAAAT    19980

GTTAAGACTT ACACACAAAA GTAATATCAC AACAGAAATA AATATGAAAG AGAAAAATAA    20040

AGACAGTAAA ATAAATTTGA ATAGAATACC TAAAAACAGC ATCCCAATTC AAATATTTTC    20100

CTTGTTTGGA ATCTGAATGC CGATCTAGAT GTTTAATTGT TTCAGGATCT CGAATCAGGC    20160

GCTTAAATTT CTCAACTTCT TTCTGAAAAT AAAAAGGAAA TAATAATGGG TTACTAATCA    20220

CACATTTCAA GGAAAAATTG AATTTAAGTA ATTTACTACC TTTCGTTCTG TAGCTCTATC    20280

ATGTTCTAGT TGACGGCAGC AGATAAGCAG ATCATTAAGT ACTAGACTCA TGGTTCACAA    20340

TTTCAGAACA CACATCACTG TCTGTAAAAA AAATACATAT AGGTATATAT ATGTATATGT    20400

ATATATGCAT ATATAGAGAG AAAGAGGTGT GAAAAAATGT GTATATAATT ATTTTATACT    20460

GCAGTATTTA TAGTTAGATT TAACTGTACA ATTAGAGGCA CATTCTGGTC AAAGGCACAA    20520

TAATTTTTCT TAACATTTCC GTATTTAAAA TGAGATTTTC TTAAAATCTA TACAAGTAAT    20580

GCTGTAACAC AAAAATGTTT GCCTTGCTTG CAGTAGTAGC AGGATTAAAA TAAAAGTATA    20640

ATTTACACTG GACGCAGTGG CTCACGCCTG TAATCCCAGC ACTTTGGGAG GCCAAGGTGG    20700

GAGGATCACA AGGTCAGGAG TTCGACCAGC CTGACCAACA TGGTGAAACC CTGTCTCTAC    20760

TAAAAATACA AAAATTAGCC GGGCTTGGTG GCGCGCGCCT GTAATCCCAG CTACTCAGGA    20820

GGCTGAGGCA GGAGAATCGC TTGAATCTGG GAGGCAGAGC TTTCAGTGAG CCAAGATCGA    20880

GCCACTGTAC TCCAGCCTGG GCAACAGAGG AAGGCTCTGC GGGGCGGGAG ATGGGGAAG    20940

TATATTTACT TTTTATTACT CTGAGACCAA AGAAACATGA CATTTAAATT GAGACATGAA    21000

AGATGAATAG AAAACAGCCA GGTAAATAAG GAAATGAGCA CTCAAGGATT TAACATTGAC    21060
```

```
AATGAACTAT TTAAAAGCAC TCTTGGCCAG GCGTGGTAGT GTGCTCTTGT AGTCCCAGCT    21120

ACTCAGGAGG CTGAGGTAGG AGAATCGCTT GAACCCAGGA GGCAGAGGTT GCAGTGAGCG    21180

GAGATCGCGC CACTGCACTC CAGCCTGGTG ACAGAGCAAG ACTCCGTCTC AAAGAAAAAA    21240

AAAAAAGCAC TCTTGCTTAT ATGGAGAGAC ATGTCATTTT GCTGAGCCAA AGGCTTAAAA    21300

CATGCTTTGG AGCTGATAAG TAGGAGGTTA TCAGAGCTAG TAAGCTTTGC CTACCACTTC    21360

CATCTCAACT GGTATTAAGG TTCTTATTTA ACACATAACA ATAGGAGTAA AATGACATTT    21420

CTGTTTTAAA AGGAAATGAA GCAAATTCTA TGCTATGGTG GTATCCTTTG CAAATATCAA    21480

GGATCAACTA TATTTTACTA TGCCTTGATT CCACTGAGTA GCTCTCTTCT TTTGGGGCT     21540

TCTGATATAA TCAAACTCTC TTTTGATGTC CTTCAAAAAA ATGTAGTAAG AACAGCATTT    21600

CAACATGGAC ACAAAGATGG GAAGAACAGA GACTGGGGAC TGTTTGAGGG TTGGAAAGAA    21660

AGGGAGGTAT GGCTTGAAGG GCTACCTATC AGGTACTATG CTCACTACCT GAGTGACAGG    21720

ATCATTCGTA CACCAAGCCT CAGCAACATG CAATTTACCC ATGTAACAAA CCCGCACATC    21780

TACCCACAGA ACCTAAAGTA AAATAGAAAA GAAAAAAAAA GAAACAGCAT TCTGTTTTAC    21840

TAGTTCTGAT CTAAACCTTT ATATAATACA AAGAAGTTTT TTATTAAACT ATGAATGTCT    21900

GTAAACAGAG AAAAAATACA TATATTTATG TATATTATAC CTACAAATAA CTATATCTCA    21960

AGAAGTAAAA AGGTAGGGAA AGTCCTTCTC CTATCCATCC ATCTAAATTC TACTTAATCT    22020

TTCAAGATTA AGTATGTTTC TCTGCCCCGA TTCAATCTCA CAGAATCTCA AAATTGGGAG    22080

GAACTAAAAG ACCAGGTCCA ATCTTCCTAT GAAGGAAGGA ATGTCTCTTA CAAAATGAAT    22140

GCCCTGTCTT TGAATATTCT CAGTAAGAGC TGACTACCGG GGCTAGGCGT GGTGGCTCAT    22200

GCCTGTAATC CCAGCACTCT GGGAGGCCGA GGTGGGCGTT CCACGAGGTC AGGAGTTCGA    22260

GACCAGCCAG CCTGGCCAAC ATCGTGAAAC CCCGTCTCTA CTAAAAATAC AAAAATTAAC    22320

CAGGTGTGGT AGCATGTGCC TGCAATCCTA GCTACTGGGG AGACTGAGGT AGGAGACTCA    22380

CTTGAACCCA GGAGGCGGAA AGTGCAGTTA GCTGAGATCA CGCAATTGCA CTCCAGCATG    22440

GGCGACAGAG CGAGACTGTC TCAAAACAAA ACAAGACAAA AAAAACAAAA AGAGCTGACT    22500

ACCCATTTTA TTAGCAGATG GCTCTGATTC TCTTCTCCTT TCATATTCAC TGGTGGTTCT    22560

TCTGACTTCC CCCATCCCCC AACACTATTA CAACTTCCGC TTTACTCTGC TATAGATTAC    22620

AGATTGTTAT TTGAGTTCTT TTCATTTGAT TATATACTTC CTGTGGACAA GTATTATCAT    22680

TTTTGTTTTT CCATTCCTTA TGGTTTTATC TAGGAATCTT CTTACTTCTT CAATCTCAGT    22740

TTAAAGCCCT CTTGAGTCAA TAAGGAAAAT GAAACTGGTA ATCTAACCAA TGAAAATACC    22800

TTAGCAATAT CCAAAGAACC ATAAGGTTTG GCACCTTTAT TCCTAAATAT ACTAAAGATT    22860

TGACACTTCC CGGAAGAGGC AGCCCTAAAC TTGACTTTTT TTTCCCCATG GTGTGACTTC    22920

CTTGAACTTG TTTTTCTTAC CTTCAGCTTA ATGATTACTT TGAAGAAAAC AAAACAGTTC    22980

AGTATTATCT ACATAAACAG AAGATGCTCA TTCACTGATA GATGCAAACA ATATTTACTA    23040

CTTATAGCTA GACAAATAAT GAACTAAACA GATACAAATC CTACCCTCAT GAAGTCATAT    23100

CTGGGCAGCA GGGTGACAAT AAACAAGTAA ATTGATAAAC CAATGCATAA TTCCAAATTG    23160

TGATGTATGC CTCTGAGGAA ACAAAAACAC AGTAATAGAA AATAACTGTA GAGAGAATCA    23220

TTTTAGATAA ACTGTCAGGG AACATATATC TCAGAGGAGT TTATAATAAA GCCAAGATCT    23280

GAACTAACTG GTGCCAATCA AAAAAAGGGC TAGAGGACCA ACACTTCAGG GAAGGAGACT    23340

AGCATAGCCA AAGGGTTCTA CAATGTTAAA GAACACAGTA TGTTGGCGGA ACTGAAAGAA    23400

GGCAGAGGAA CTATTAGGTA GTCAACTAGA GTATGAGTGT CACCATATAA AGATGAACTT    23460
```

```
CACTTATACA TTAATCCAGA ATATCTAGGT TCCACTCAAG GTTCAAACGA AAAGATAAGG    23520

ATTTCCTACT TCCTACGAGC CTCTGAATTG ACGAATTCAG TGTTCCTTTT TAGATCTCAA    23580

CCAAGTTGAC CCCTTTGCAC AACTTGACAA TGACGCTTAT ATCCCATCTT CCTAGAAATA    23640

ACTCTGCCCT TGGCATGCCA TTCTTTTCTA GTGCTAAGGA GTGTGGCCTC TGTAGTCAGA    23700

TTGTATTAGT TCAAATCCTG GTTCAGCCAC TTACAAACTG TATAATCTAG AGCAAGTTCA    23760

CTAATCTCTT CAAACCTCAG TTTCTCAATG ATAAAAGGAA AAACAATACT AGTACCTACC    23820

TCTATGAGTC CCTTTAAGGA CCCATATACA TGCTTACAGT GCCTGAAACA CAGCAAATGT    23880

TAGCAATGAT CATATTAACT TCCGTTATGA CTGTTTCGAA AGTCTCCTGA TATCTCTTCT    23940

TCCGCTCATA CCTCAAAAAC AGCTTTGTTT TCTTGGTCTC ATCCATTCCT ATGACTTCAG    24000

CAGCTGAAAA CCCACAAAAT ATATTTCATT CAATGCCAGG CCTCACGCTG GAGCTTCAGG    24060

GTCCTTCTAC ACTTTGTGCC TTTACACGCA TTTTTCCTTC CATCTGGAAG GCTTCTACCA    24120

TCTGCCAAGG TAACACTGCG AGGTCTCACC ACAAACTGAA TTGATAGTCT CAGGCTGAGT    24180

TTGCAGAGAA CCAAAGTCAC TCCTCTACCA TCAGAGTACT CCCCTATCAC CACATACATT    24240

ATCATCCACT GTAGTTGTCT TATCTGTACC TGGTAAATAC AGCAGCTAAC GCTCACGAGT    24300

GCTCACCACA GGTCAAGATT ATCTCACTTA TCTTCACAAG ACAGTAGAGA GCGGCCACAC    24360

GACTGACAGA ATTCCAATTC CAGCCGTATG ATTCCAGAGC CCAAGCTCTT AACCGCGAGG    24420

CTGAAGTTGA AATATCAATA AATGCTCGCT GACTAAAAGT ACTAAATACG AGAGAGAGAT    24480

CAAAAGATGA CTAGTCAAGT CGCGTAGTTA AATCTGAACC CTAAGGTGAC ACAAAAAGAG    24540

GATGCGCAGG AGGCAGGGTT CAATTCAGGG CGTTTAAAAG GAGGAGGTTA TTGGCCAAGT    24600

CCGCTAAGCA CCCGGAGAGA GGCCAGGAAA GATGGAGTGA GGAGAGGGAG GAGTCAAGGG    24660

CCACTCTGGA GGGGTGCATG AGATTGGCGG TCTGGGGAGA GGACAGACTG GGTCGCACAC    24720

GACTGAATTT CCCAGCGCAG AAGCCGCTGC GTTGCCTCCG CGCCCCTACC ACTGCACTCG    24780

GAAGGTCAAA GTAGTATCAA CCGCGGCGGT GGCTGCAGCG CAGATCCCGA CTCCTCTCGC    24840

CTCCTCCCGT GGCCACGGCT TCTTTTCTCC GTTAGCCACG CAGCTACCTA CTCCCGCTTC    24900

CGGTTCAAAC CCTGCGTGAC TGCCCAGCGC CCACTTCTGG AGGAAGAAGC AACGCCAAGC    24960

AGCCGCAGAA CACGTTATGC CCATGCGCAT CCAGTATCAC GCGGTCTCCG CGCTCAAAAC    25020

ACTGCCCCCA AACATTCGGC CGTCGGAGCA AACGCGCCTG CGCCATGTCC ACCAATGGCC    25080

AGCGACTTAG CGTTTGCGCT CCCTTCGGCT CGGGCTCCGG GGCTCTCACC CACCCTCTTC    25140

GCCCTCGTCG TCCTCCCCGC CCTCCTCATC CCCGCCCCTC CAAGTCTGAG GACGGAAGTG    25200

ACGACAGTTC CGAAGCGAAC GGAGGCGGGT TTCATTTCGG CGCCTTTCTT TCTCTGGCGG    25260

AACGAGTTGG CTGCCGTGAA GCGAAAGAGG CGGGACAAAT TGCCGCGAGT TCAGTGCCGC    25320

CACTGGAACC AGGAGATGCG GCGCAGGAGC TGTCGCTGTG TTTGCTTTAA CCTGAGTCTT    25380

GTTCCTTATT GTGGTTCCTG CTGTGGTTTT GATCATGTTG TTACCCTCGG ACGTAGCCCG    25440

GCTTGTATTG GGTAAGCGCG GACGCGGGAA GGAGGGTTAT TGGACCCGGC TATGCTGGAC    25500

AGAAGGACCT TTGAGGCCAA AGGTTTTCCC TTGGTAGGGA GCTTTGGGG TTTTGCCTCC    25560

CAGCTTACGA GTTGAGACTG GCGGTGATTC TTCGTCATTC GGAGGTTCTG GGCAGTTTAA    25620

GCCTCTTTGT ATGTAGATGC TCCTCTCTTC AGAGGCTGCG TGGCGAGGGG AAGCCCGAGG    25680

GGAAGCTCGG GGTGGAACAC CTGGGGCGGA TTCGGAAGGA AAGTCAGGCC TCCACACTTA    25740

ATTAGGACCC CTGAAAGAGC ATTTGTCTGC ATGACGGACG GATTGCGTGT GCTTCAACCT    25800
```

```
TGGGCGCAAT TTCCTTGGTT CAGTGTTGGG ACCAAAATAG GGCAAATAGG GAGTTCCCCG  25860

GCCCCCCATC TTTGTAGAGA GACCTTCCTG GCGCCCTTCT AATAACCCGC CCTTATAACT  25920

ACGAATTTGG GAGTAGGGGT GATCTTCCTT CTCCATCCTC CACGCAATAC GTCGTCCAGT  25980

GTAGAGGTGT GAAATGCCAG TTGCATATTT TAAAACAGCA ATTCCTGTTC CTTTGATCAG  26040

CGAAAAATTT CAGAGGGTTA ATTGCCTTAA ATTAGTTGAA CGTTTTCTAG CCCTAGTTTT  26100

ACCTTCATTT GAGGAGGGAT TGTTTGTGGG TCACTTGTCT GTCAGGGTGT ATTGTCTGTG  26160

TGAGAGACGG GTTTTGTTGT TGTTTGTCCC CTGAAAGAAT AAAGAGGATT GTACTACAGG  26220

GGACGAGAGC CAGGTAAAGC TCAAAACCCG AGCCAGTAAT TTACGGACGT CGTATGCGAC  26280

GTCCCTAAAA GTAAATGGCA AGCATCTGTG ATGAAACCTC CCATAGTATT CACAGCCATT  26340

ACTACTATTA TTTTATTGTT CGGAAAACCC ATTTGTCTTG TGCCTCTTTT AAATGCCCAG  26400

CGCTGTCCAC AAAAATGTTA TTTGCGCAGG GCTCTTGATA AGCACATTTT GCAGGAAACG  26460

TTAAACGGAA ATGGTTCCAC CATCCATTTT TGAAGAAACT TAATGACAAG TTTAATGTTT  26520

TGTTAATGTC TGATTAATCT TTTGCTTAAG AATTCTGAGT TTTGGCAGTT TGGTAATCTA  26580

GTTGAGTTTC GGTAACTATA GTCTTAAACA TGGTTTCTCA GCCTCAGTAC TGTTAACATT  26640

TTGGGCCTCA TAATTCTTTA TTGTGGGGAG CTATCCTGTG CTCAAACATT GTAGGATGTT  26700

TAGCAGCATT CCTGGCTTCT ATTCACTAGA TTACAGTAGG ACACCCGTTC CCCACCCTAC  26760

CCTTACCCAG TTGTGATCAG TGAAAATGTC TCTAGATATT GCTAGTATGT CCCCTGGAGG  26820

GCAGAATCAC CCCTAGTTAA GAAAGCCCTA AGAAAGCAGT ATCATTTTCT AATTGAAATA  26880

ATTCACATCG ATGTGTGAGT ATTCTTTCTC CACAAACCAG CTACTCTGCT GACTTCCTGC  26940

TTTTCATTTA ATGGACAAAA AACGCCAGCC ATGGTTTTCT TATCTTAAAA ATCTTTGTCA  27000

TTCACATTCC ATTTTCACTG CCACCAATCC CGCAATGTGC CTGCCATTAC TTCTCTTTTG  27060

GACTTCTGTC ATGGCTTCCC AGACAGTTGT CCTCGCAATT CATTTATTT ACTGTTGTTA  27120

CAAATCTCCC TGAAGCTTTC ACACTATACC TTTTAGTCTG AAAGTTGAGA TAATTCTATT  27180

CTTACTAAAA ATTTCAGATG GGCAGGAGTA TACAATACAA AAAAGCCTCC CCATGCCTAA  27240

TGCTCTTACT TTTGTCGTTT ATCATTTTAC ATCTTAAATA GATACATATC GTGTATATCT  27300

TTCTCATATG AGGTTTATTA TTTACTCATG ATTCTTTTCC TATCAGTACC CCCTCGCCAT  27360

CTTCAGCTCC TCTTGTTATT GGTCCCTTCA TAATGTTTTT TTTCTAGCAA ATCTTTGGGT  27420

GCCTAGTATG TTCCAAACAC TGTGCCAATT GCTGAACATA GAGAAGTTAA GTTTTCTCCC  27480

CTTAGTGTTC AGATAATTAG GTTTTTTTTA AATTCTTAAA CATACACACA AAAAAACACT  27540

TTTCTGGACC CCACTAGACA TTAGACACCC ATTAAACAGA ACATTCTGTC TTATGTTCTG  27600

TGTCACCCTT TCACAAGTCA AATTTATTCA AGAACAATG AATTCCACTT AGTTGCTGTT  27660

CTTCACCTAC CTTTTATCCT TCAGGATACT GCACTCTGAC TTTTGCATCT CACTACTCCA  27720

CTTAAGTAGC CCTTATTGCC TTGCTGGGAT TTTACAAAAT GTTGTGTGGG CCAGAATACA  27780

TCAAAGTGTT TGTTGCCTCT GGGCCATCAG TTCAGTTTTT ATCTATTTAT TCAAGGTGCT  27840

CTGTGGAACT GATCCTACCT ACCTCTCCAA CTTGATCTCA ACTTCCTAAC ATCTGTTTTA  27900

TGCTGCAGAC ATGCCAAACG AATTGAAGTT TCTTTGAAAA TTCTTGTATG TATTCTACTT  27960

CTCTTTGGCT TCCTAGTACA CTTCTATTCA AGGTTCAGGT CATGCCTGAT CTCTGAAACT  28020

TCATTCAGCA AGTACAGTCA GTACTTCTTA AATGTTGCCA TAGCATTGTA CTTCTGTTAC  28080

AACCTTATCA TGTCTCATTG TAGATGTGTG TTTACTTTTT TTTGATAAAA TATACTAACA  28140

AAATTCAACA CTTAAAAATG TATAGTTCTT AAAGCCCAAA ACAATGAGTT TGTTGTTGTT  28200
```

```
GTTGTTGTTG TTGTTTGTTT TTAATGTACA GATCAGTAGT GTTAACTATA TTGACATTTT   28260

TCTGCAACCA TCACTACCAT CAGTTTCTGG AACTTTTTCA TCTTCCCAAT TTGAAACTTA   28320

CTTGGTTTTT TGTTTTATTA GTAGTCTTAG TCATGGATGA ATGGACAAGC TTCAAGAGTT   28380

CTGGGAGTCC CCAAAACTAT CATCTGTGAA GGTTTTCTTG AATAGATTTG TTACCTTCTG   28440

TATGAGACAG CATGCAGTAA AAAAGTAGA AACCATTCTG AGTATTTAAC ATGGAAAGAT    28500

TTAATGAGAG AATTCGTTTA CACTGGTGAG AGAAAAGCTA AGACGCCCAG CAGCTTACAA   28560

CTAAGGCATC TCAGTGGTTA GCAACAGTAG GAAGCCACTA TGCTAATGAG AAGGATAAGG   28620

AGAGAGGAAG CAATCAAGAG GCTGGTTTGA CTGCGGAACG TGGAAGACTT GTCTGATGAG   28680

GGAGTGGTAG TCTTAGAGGA GACTCTACTG AGGCAGAAAG GGAATGGGGG AAAAATATGG   28740

CTGCTTCCTC CTGCCCTCCA GCCTCCCACC AGTGCTTCCT ATTTACTGAG CCCAGCCAGT   28800

AGCAGGCCGA CAGAAGAGCT TGGGGAACAT TGCCTATATA GAGTCAAGCT TTATGTCATA   28860

CAGTAGAGAG CGACAGAAGG GTCAAGAACG TGTTTGAGGT CAAACAGGAC CAAAACTGAC   28920

ACACCCCTAA CAGGTCAAGA GCTGCTGGTT CTATTCACCT TTATATCACC AAAACATAGA   28980

TATTTAATAA AACATTTGCA AAAGTATGGC TCTGATTATG ACACTCCTTT GTTTATTTAA   29040

TAATATATGT ACTCATTGCT GTCTAAAACT TTTCATGATC CTTACCCATT TTGTCTTTTC   29100

TGTTGTATCT CCAACTGTTA CCCTTCATAA ACCTTGTGCT GCATCCAAAC TGGACATGTT   29160

CCCCAAATAT GATTGCATAT ATACTTTCTG TCAGCTTCTT TGGGATTCCC AACCATCCTT   29220

CAGTACTCAT CTGCACCTTC AAACATCACA TAATTTCCAA GCTTAGTAGT GGTTTCTCCA   29280

GCCCCTCCCT TCCCATGAAG TGAGTCAGCT CTATTTTCTT ACCATTTTTG CTTTGCATTA   29340

CAGTTATTTG TGTATATATC TTCTATCTCC AAGTAAATTG TAACTTTATA GACAGAAACC   29400

TTGTCCCTGT TATTTGTGGA TCTAGTAATA TAAGACAACA TAAGGTACGG CTTCCTAAGA   29460

ATTATTTGCA TGCTTAAAGA ACATTAAATT ACTAATCTTT CTAGGAAATA ATAAAATATG   29520

TGAAGGAGAT GTTTTCACAT AGCGTGCTTT ACTATCTCTT GCTTGCTTTA AACCTCTCTT   29580

TTTATCTTTC CCTCTCTACA AGTAGGAAGA AAAAATACCC TTCATATAGT TAGGATCTTA   29640

TCCTTTCTTC TCTTTTTCGG TTGTTTCCCC TTCAATTCAT TTAGTTACTC ATTACCACCT   29700

CCACTTATAA TAAAAGTAGG CTGAAGATAA TATTATGTTA AGAAGGAAAC TCAGGCATAC   29760

TTTCTTACCT ATTCAGGGAC CTTTGTCAGT AAGTTTACAC AAAAAAATAC ACTTCTTTTA   29820

TTCTTAAGTT GTTTTTAGGA ATAAAAGGAA AAAACAGTAA TAACTAATAT TAGTTGTAGA   29880

ATAACGATTT GTATTATACT GATAAGAGAT GATTAGTGCC TAGTTTGTAT TTTCTATTTT   29940

ATTTATTTAT TTCTTGAGAC AGAATTGCAC TCTTGTCATC CAGGCTGGGT GCAGCAGTGA   30000

GATCTTGGCT TACTGCAACC TCTGCCTCCC AGGTTCAAGT GATTCTCCTG CCTCAGCCTC   30060

TGAAGTAGCT GGGATTACAG GCGCTCACCA CCACGCCCGG CTAATTTTTG TATTTTTAGT   30120

AGAGACTGGG TTTCACCATA TTGGCCAGGC TGTTCTGGAA CTCCTGACCT CAAGTGATCC   30180

ACGCGCCTCG GCCTCCCAAA GTGCTGGGAT TATAGCCATG AGCCACTGTG CCCAGCCAGT   30240

ATTTTCATCA TATTTGGATT TTCATTCATC TAACACCAGA GATTTAGAAT TAATTTGTGC   30300

CTAAAATTTC CTGTTACCTG ACTGAGAATT GGTTATAGTC AGATACTTAA TGATGATAAA   30360

TAAACATTTT GTAGGCAGAT ACTAATCATA TATATATAGT AAGGCCTAAT TTAATAGGTT   30420

CAATAGGTTC TTGAAAACTG CAACTTTAAG CAAAATGATA TATAATCAAA CTAATTTTAC   30480

CATAGGCTAA CTGATATATA CAAGAATTTC TTCAGCATAT TTTTGGTCAC AAAAATATCA   30540
```

```
CCACACTTGT AAATAAAGTC CAAAACACTT CTAATATTAA ACATTGAAAT ACATGTAAGC    30600

TATATATACA TTTAAGATGG ATTAATAAAA ACAAGATAAT TACTTACCCA GTTAGTCCAG    30660

TTCAAGGTTG CAGGTAGCTA GAGCCTATCC CAGCAGCTTA GGGTGCAAGG CAGGAACTAA    30720

CCCTGGGCAG GATGTCATTC TGTTGAAGGG AGCACTCACA CGCCCACGTA CACTCACTCA    30780

TGCTCACACT GTAATAATTT AGACACACCA GTTAACAACG TGCACATATT TGGAGTTTGG    30840

GAAGAAACGT GTACCTGGAG AAAACCCATG CAGGCATGGG GAAAATGTGT AAACTCCACA    30900

CATACAGTGT CCTCAGCCAG AAATTGATTT TTTTCTCTCA TCAGCAGTAT AACAAAAACA    30960

TTGAACAAAA TGATGGTATT CGAGGACTTG CTATATAATG ATCAGTGAAC ATGAGAGTAG    31020

TCAACTATTT ACTACATTAT TTTGAACTT TTGGGACAAA AGTAAACCAG AATACATCAA     31080

ATCTAATCTA AAATGAGAAC TCAAGATTGC CAAAGTTGGG GCATGTTGTT AAGAGCAGAA    31140

GATAATGTAT CCTAGATATT ACTATTTTGA GATACATTAT AACTTAAACA CTTATTATAG    31200

AGGTAATCTA GCTTTTAACA GCCCCATCTC ATGTGTGTGC TATACAGAGG TATAATGTTT    31260

TATGAAATGC CATGAATTAT CTGTAATGAT TCCTTTCCAG GTTATGCTAG CACAAATGAC    31320

AATATTTTTC TGAAAAAGGT TTACTGTGTA TCACTGTATT CTGTCTGGGG CATTGTTTCT    31380

CAACCTTTAT TTCATTACAC AACTTTAAGG AATCTTCTTA GGCTTTTTTT TTTTCCCTGA    31440

CCCTCCTCTC CTCCCCACAC GAAAGTTTAA TGTTTTAGTG TCATGAATAT ATTGTATATG    31500

TTTATATATC ATGTGTATCT GTGATTTATG CATAAAAAGA GGGAGATTTT CTTCATTCCT    31560

CCCTGCCCCA GAACCAATTT TCAGCCTCTT AGGGCAGTAT GACTCCTTTT GAGAATGCAT    31620

GGTCTAGGGG AAAGCAAATC TACTTTAAGA TAGATAAAAA TCTACTGCAA ATCTATAGTA    31680

GATTTTAATA CCACCGTCTA TCAGAAGTCC CCAAGTGACT GAAGGCATCT AGGGTGATAA    31740

GTACTTGAAA CTCCACCATG AAAAGGAAGT ATATTTGAGG TGTTCAATCT AAATCTTGAA    31800

GCATATGAGG AAAAAGCTCC AACTGTCCTA ATTTTAAGGT GATTCTAATA GTCTGTAGAA    31860

GTTTTAAATT TTTGTGTTTA CAAAAAGCTA GTAACAGCTA ACTCACCTAT TCCAAATATT    31920

ATAACGGTCG GAAAGCCAGC CATCATAAAA ATTACTTTTC AGCCAGCTAG TTTTCACAAA    31980

AAGAGAAGAA AACATTGCAG TGTATCTTTG ATCTAATTAA TTTCACATCT GTGGTTTGAT    32040

GTTCAATGAT AGGAAGATTG AAGTCATGTT ATCTGAGATA AAGCTTTCTT CAGATATCCA    32100

AATGCTTTCT CCAAAACACA ATGCCTTTGG TTTTTGATTT GTATATTTGT TGTTTCTTC     32160

TTATTAGTTA GCAAGAGGTT GGAAAACAGA TTCATCAACA AGTAGAGAGT GGTGAGTTGA    32220

TTCCCAAATC ACAGCTAGGG CATTGCCTGT AACGAGATGA CCATATCCTT GCCCTTTCCT    32280

TTTTAAAACC TTAGTGTATA ATGACTTTGT AGGCAACCTT ATTAGGTTTT TCACCTGTTG    32340

GACCTGGTTA ACGATACAGT TCCAGGTGAA GAGAGTAGAA CGTTATAAAG TTGGAAGAGA    32400

CGTTAGACAT AATTTCTTTT TTTTATCTTT TAAATTCAGG GGTACATGTG CAGGTTTGTT    32460

ATATAGGTAA ACTTGTGTCA TAGGGGTTTG TTGTACGTAT TATTTCATCA CCCAGGTGTT    32520

AAGCCTAGAA CCCATTAGTT ATTTTTCCTG ATCCTCTACC TCCTCCCACC CTTCACCTCC    32580

AATAGGCCCC AGTGTGTGTT GTTCCCTTTA TGTGCCCGTG TGTTCTCATC CTTTAGCTCC    32640

CACTTATAAT TTCAGTAGCT AACAAATACT TACTGACTAT TATGCCAGCA CTGAGATAAG    32700

TGTACTTCAA AGGAAAATAT AAGGGAATAC TTATAAGTAT TAAGTAATAC CTATAAGGGA    32760

ATATTTAATA GTAGGGAATA GGGAGTAATT ATACTAAACT GTGAAGAATG AGTTGAAGAT    32820

AGCTAGGTTA AGAAAAGATT AGCTGCCCAA GCAAAGGAAA TAGAATAAAC AATGGCCTTG    32880

AAATATAATC AATGTGTATC TGTGGGACTG AAAGACCAGT TTGGCTGGAA GCGATGGAAT    32940
```

```
GGTAAAACAT AGGCTGAAGA GGAAATTAGG GTACAAAGCA AGTAGAACCT CATACGACAC    33000

ATTAAAAATT TGAAATCATA GGCCGGGTGC AGTGGCTCAC GCGTGTAATC CCAGCACTTT    33060

GGGAGGCCGA GGCGGGCAAA TCACCTGAGG TCAGGAGTTC AGACCAGCC TGGCCAACAT     33120

GGCAAAACCC CATCTCTACT AAAAATATAA AAATTAGCCA GGCATGGTGG CAGGCGTCTG    33180

TAATCCCAGC TACTTGGGAG GCTGAGGCAG GAGAATCGCT TGAACCTGGG AGGCAGAGGT    33240

TGCAGTGAGC CGAGATTGCA TCATTGCACT CCAGCACAGG TGACAAGAGC GGGACTCCAT    33300

CTCAAAAAAA AAAAAAAAAA ATTGGAATCA TATTTTTTTA TTGAGATATG ATGCACATAC    33360

TACAAAATGT AAACTTCGTT GTTTTTCAGG GTATGAAAAT CCAGGATATT TATGGATTCA    33420

TAATGTGCAG ATATCACCAG TAATTTCAAT ATTTCCATCA CTCCAAAGAG AATCCTTATA    33480

CTATTAAGTC ACTTCCAATT CCCCCTTGCC CCGTCCTCTG CCAACCACAA ATCTACTTTC    33540

TGTATCTATA CATGTGCCTT GCCTGGACAT TGCACATAAA TGAAATAGAA TATTTCGCTT    33600

TTTGTGTCTG ACTTTCACAT AGCATAATGT TTTCAGCCTT ATTCCATGTT GTAGCAGGTA    33660

TTAGTACTTC ATTCCTTTTT ATAGCTGAAT ATTTCATTAT ATGAATATGC CATATTTTGT    33720

TTGTCCATTC ATTAATGGAC ACTGTTATGA AAAATGCAGG CCAGCTGTAA TGGCTCACCC    33780

TGTAATCCCA ACACTTTGGG AGGCCAAGGC AGGAGGATTG CTTGAAGCCA GGGGAGCGAG    33840

ACCAGCCTGG GCAGCATACT GAGACACCCC ATCTGTACCA ATAAGTAAGT AATTAGCTGG    33900

GCATTTATTT GGTGGTACAT GCCTCTAGTC CTAGCTACTG GGTTGGCTGA AGTGGGAGGA    33960

TCACTTCAGC CCAGGAGTTC AAGGTTATAG TGAGCTATGA TTGAGCCACT CTACTTCAGC    34020

CTGGGTGACA GAGCAAGACT CTGTCTCTGA AAAAAAATAA ACTGACCATA AATGTCTGGA    34080

TTCCATGCTT CAGAGTTGAC TAGATAAATA AGAAAGGTCT GGATTTTTTA TTTTGTTCCA    34140

CTAATTTCTG TGTCTAACCT CATGCCAGTA CATCGTCTGG ATTACTGTAG CTTTACAGTA    34200

AGTTTTGAAA TTGGTAAGTG TAAGTGCTTC AACTTTTTCT TCATTTTCAA GATTATTTTG    34260

GCTATTCCAG CCCCCTTGTA TTACCTTAGG AGTTTTAGGA TGTTTGTCAA TTTCTGCACA    34320

AAAGGCAGTT GAGATTATGA TAGGAATTGT GTTGAATGTA TCGGTGAATT TTGGGAGTAT    34380

TGAGTTTTTA ACAATATTGA ACCTTTCAGT CCATGAACAC AGTATGTCTT TGCGTGGATT    34440

TAGGTCTTTA ATTTCCTCCA GTGACGTTTT CCAGTTTTTA GTATGCAAGT CCTTTACTTT    34500

TGTTAAACTT ATTCCTAAGT ATTTTATTTC TTTTGATGCT ATTGTAACTA GCATTGCATT    34560

CTTAATTTTT GGTAGTTCAT TGAGATTTAT TGACTTTTAT ATATTCACTG TGTATCCTGC    34620

AACCTTGTCG AAGTCATTTA TTAGCTCTAA TAGTTTTTGT TTTGTTTCGT TTTGTTTTTG    34680

GGACAGAGTT TCGCTCTTGT TGCCCAGGCT GGAGTGCAAT GGCGCAATCT TGGCTCACCA    34740

CAACCTCTGC CTCCCGGGTT CAAGCGATTC TCCTGCCTCA GCCTCTGGAA TAGCTGGGAT    34800

TACAGGCATG CATCACCTTG CCCAGCTAAC TTTGTATTTT TAGTAGCACC AGGGTTTCTC    34860

CATGTTGGTC AGGCTGGTCT CGAACTCCCG ACCTCAGGTG ATTTGCTGGC CTTGGCCTCC    34920

CAAAGTGCTG GATTATAGGC ATGAGCCACC ATGCCCGCC CAGGGAGGTT TCTTAACTCC     34980

TTTTTTTTTT TTTTTTTTTT TTTTTTGAGA CAGAGTCTTG CTCTGTTGCC CAGGCTGGAG    35040

TGCAATGGCA CCATCTCGGC TCATTGCAAC CTCCACCTCC CTGGTTCAAG TGATTCCCCT    35100

GCCTCAGCCT CCCTAGCAGC TGGGATTAAG GTGGACACCA CCATGCCTGG CTCATTTTTT    35160

TGTATTTTTA GTAGAGACGG GGTTTCACCA TGTTGGCCAG ACTGGTCTCG AACTCCTGAC    35220

CTCAGGCAAT CTGCCTGCCT TGGCCTCCCA GAGTGCTGGG ATTATAGGTA TGAGCCGTGG    35280
```

-continued

```
TGCCTGGCCT CTAATAGTTT TTTTGTTGTT GTTGTTGTTG TTTTTTATGG CTTCCTTAGG    35340

ATTTTCTTTA TAAGACATGT CATCTGCAAA TAGGGGTAAT CTTGATTTTT TCCTTTCCAA    35400

TCTGGATGCT TTTTTTTTTT TTCTTTTGAG ACGGAGTCTC TCTCTGTTGC CCAGGCTAGA    35460

GTGCAGTGGC CCTATCTCAG CTCACTGCAA CCTCCACCTC CCGGATTCAA GCAATTCTCC    35520

TGCCTCTGCC TCCTGAGTAG TTGGCATTAC AGGCATGCAC CACCACACCT GGCTAATTTT    35580

TGTATTTTTA GTAGAGACGG GGTTTCACCA TGTTGAGCAG GCTGGTCTGG AACTCCTGAC    35640

CTCAAATGAT C                                                        35651
```

MUTATED FORMS OF THE ATAXIA-TELANGIECTASIA GENE AND METHOD TO SCREEN FOR A PARTIAL A-T PHENOTYPE

This application is a Continuation-In-Part of U.S. Ser. No. 08/629,001, filed Apr. 8, 1996, which is a Continuation-In-Part of U.S. Ser. No. 08/441,822, filed May 16, 1995 now U.S. Pat. No. 5,756,288.

GRANT SUPPORT

This work was supported in part by grants from the National Institutes of Health Institute of Neurological Disorders and Stroke (NS31763), United States-Israel Binational Science Foundation, A-T Medical Research Foundation, A-T Medical Trust, and the A-T Children's Project.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling cell cycle progression and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference as well as to the reviews by Harnden (1994) and Taylor et al (1994).

Despite extensive investigation over the last two decades, A-T has remained a clinical and molecular enigma. A-T is a multi-system disease inherited in an autosomal recessive manner, with an average worldwide frequency of 1:40,000–1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. The co-occurrence of cerebellar ataxia and telangiectases in the conjunctivae and occasionally on the facial skin—the second early hallmark of the disease—usually establishes the differential diagnosis of A-T from other cerebellar ataxias. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of defective checkpoints at the G1, S and G2 phases of the cell cycle. The G1 and G2 checkpoint defects are evident as reduced delay in cell cycle progression following treatment with ionizing radiation or radiomimetic chemicals, while the rise in the p53 protein level usually associated in normal cells with radiation-induced G1 arrest is delayed in A-T cells. The defective checkpoint at the S phase is readily observed as radioresistant DNA synthesis (RDS). Increased intrachromosomal recombination in A-T cells was also noted recently. Cellular sensitivity to DNA damaging agents and RDS are usually considered an integral part of the A-T phenotype.

Although these clinical and cellular features are considered common to all "classical" A-T patients, variations have been noted. Milder forms of the disease with later onset, slower clinical progression, reduced radiosensitivity and occasional absence of RDS have been described in several ethnic groups (Fiorilli, 1985; Taylor et al., 1987; Ziv et al., 1989; Chessa et al., 1992). Additional phenotypic variability possibly related to A-T is suggested by several disorders that show "partial A-T phenotype" with varying combinations of ataxia, immunodeficiency and chromosomal instability without telangiectases (12–16) (Ying & Decoteau, 1983; Byrne et al., 1984; Aicardi et al., 1988; Maserati et a;., 1988; Friedman & Weitberg, 1993). Still, other disorders display the A-T phenotype and additional features; most notable is the Nijmegen breakage syndrome that combines A-T features with microcephaly, sometimes with mental retardation, but without telangiectases (Weemaes et al., 1994).

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various malignancies, with a 3- to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. The main reason for the unreliability of this assay is the various degrees of overlap between A-T heterozygotes and non-heterozygotes with respect to radiosensitivity. Cytogenetic assays for carriers have the same problems as for prenatal diagnosis, they are labor intensive and not always consistent.

The nature of the protein missing in A-T is unknown. Cell fusion studies have established four complementation groups in A-T, designated A, C, D and E, suggesting the probable involvement of at least four genes or four types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22-23, using linkage analysis. The A-T(C) locus was localized by applicant to the same region of chromosome 11, region q22-23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene, designated ATM, mutations of which cause ataxia-telangiectasia (A-T) has been purified, isolated and sequenced, as well as mutations of the gene and the genomic organization of the gene has been determined.

The present invention further includes the method for identifying carriers of the defective A-T gene in a population and defective A-T gene products.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22-23 (Vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig spanning the S384-S1818 interval, generated by screening a chromosome-11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb cDNA clone, designated 7-9 (SEQ ID No:1), identified in a fibroblast cDNA library using the cDNA fragments and exons in 1D as a probe wherein the open box denotes an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences;

DETAILED DESCRIPTION OF THE PREFERRED EMBODIMENT

The present invention consists of a purified, isolated and cloned nucleic acid sequence (SEQ ID No:11) encoding a gene, designated ATM, mutations in which cause ataxia-telangiectasia and genetic polymorphisms thereof. The nucleic acid can be genomic DNA, cDNA or mRNA.

The complete coding sequence of the ATM gene is set forth in SEQ ID No:2 and was submitted to the GenBank database under accession number U33841. There is extensive alternate splicing at the 5' untranslated region (5'UTR) of the ATM transcript giving rise to twelve different 5' UTRs. The sequence of the longest 5'UTR is set forth in SEQ ID No:9. The first exon in this sequence is designated 1b. There is an alternative leader exon, designated 1a (SEQ ID No:10). The sequence of the complete 3'UTR is set forth in SEQ ID No:8. Together these sequences contain the complete sequence of the ATM transcript. The complete genomic sequence is set forth in SEQ ID No:11.

As shown in Example 4, using long-distance PCR, the genomic organization, i.e. structure, of this gene was determined and the exon-intron boundaries identified. The ATM gene spans approximately 150 kb of genomic DNA and consists of 66 (64 plus two alternative exon 1) exons. The initiation codon falls within the fifth exon. The last exon is 3.6 kb long and contains the stop codon and a 3' untranslated region of about 3400 nucleotides.

Figure 3:
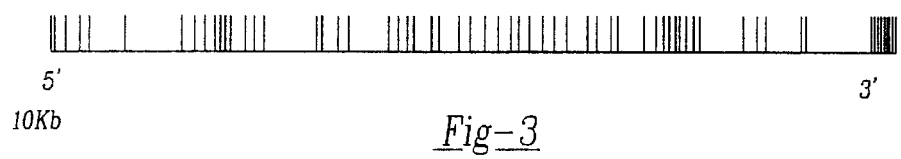
FIG. 3 is a schematic representation of the exon-intron organization of the ATM gene with vertical lines denoting the position of the ATM exons, the 3' exon and all introns are drawn to scale.

The ATM gene is composed of 66 exons (FIG. 3 and Table 1). The first two exons are alternatively spliced, and are designated 1a (SEQ ID No:10) and 1b (SEQ ID No:9). With the exception of the 3' exon, ATM exons range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 52. The first methionine of the open reading frame is located in exon 4, whereas the stop codon is located in the 3' and largest exon of 3.6 kb (Exon 65). This exon includes a 3' untranslated region (UTR)(SEQ ID No:8) of about 3400 nucleotides.

Polymorphisms are variants in the sequence generally found between different ethnic and geographic locations which, while having a different sequence, produce functionally equivalent gene products.

Current mutation data (as shown in Tables 2 and 3) indicate that A-T is a disease characterized by considerable allelic heterogeneity. Mutations imparting defects into the A-T gene can be point mutations, deletions or insertions. The mutations can be present within the nucleotide sequence of either/or both alleles of the ATM gene such that the resulting amino acid sequence of the ATM protein product is altered in one or both copies of the gene product; when present in both copies imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 2 illustrates ten mutations in the ATM gene found in A-T patients. Mutations in the ATM gene were found in all of the complementation groups suggesting that ATM is the sole gene responsible for all A-T cases.

Figure 4:
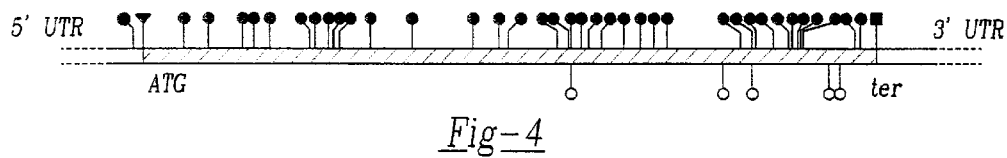
FIG. 4 is a schematic representation of 44 A-T mutations along the open reading frame (diagonal lines) of the ATM transcript, wherein for large deletions the symbols mark the locations of the 5' breakpoints, symbols above the line designate mutations expected to inactivate the ATM protein and symbols below the line designate mutations which a priori may have a milder phenotype, symbols are as follows ● truncations and exon skipping deletions (37), ▼ initiation codon abolished (1), ■ termination codon abolished (1), ○ in-frame genomic deleteions and insertions of ≦9bp (4), and ☐ missense mutations (1).

Table 3 and FIG. 4 illustrate 44 mutations identified to date in applicant's patient cohort and include 34 new ones and 10 previously listed in Table 2. These mutations were found amongst 55 A-T families: many are unique to a single family, while others are shared by several families, most notably the 4 nt deletion, 7517de14, which is common to 6 A-T families from South-Central Italy. The nature and location of A-T mutations, as set forth in Table 3, provide insight into the function of the ATM protein and the molecular basis of this pleiotropic disease.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. Of the 44 A-T mutations identified, 39 (89%) are expected to inactivate the ATM protein by truncating it, by abolishing correct initiation or termination of translation, or by deleting large segments. Additional mutations are four smaller in-frame deletions and insertions, and one substitution of a highly conserved amino acid at the PI 3-kinase domain. The emerging profile of mutations causing A-T is thus dominated by those expected to completely inactivate the ATM protein. ATM mutations with milder effects appear to result in phenotypes related, but not identical, to A-T. In view of the pleiotropic nature of the ATM gene, the range of phenotypes associated with various ATM genotypes may be even broader, and include mild progressive conditions not always defined as clear clinical entities as discussed herein below in Example 3. Screening for mutations in this gene in such cases will reveal wider boundaries for the molecular pathology associated with the ATM gene. The present invention therefore allows the identification of these mutations in subjects with related phenotypes to A-T.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

In cloning the gene for A-T, the strategy used was a standard strategy in identifying a disease gene with an unknown protein product known as positional cloning, as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., 1992; Tagle et al., 1993). In parallel experiments, YAC clones were bound to a solid matrix and used to select cDNA fragments from a heterogeneous cDNA collection representing several human tissues (Parimoo et al., 1993). The cosmids were also used for exon trapping with the pSPL3 vector (Church et al., 1994). The captured cDNA fragments and trapped exons were mapped back to the A-T region by hybridization to several radiation hybrids containing various portions of the 11q22-23 region (Richard et al., 1993; James et al., 1994), and to high-density grids containing all the YACs and cosmids spanning this interval. An extensive transcriptional map of the A-T region was thus constructed (Shiloh et al., 1994a).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the cDNA clone, 7-9, (SEQ ID No:1) obtained from a fibroblast cDNA library.

Hybridization of the 7-9 cDNA clone to the radiation hybrid panel indicated that the entire transcript was derived from the chromosome 11 locus. The full sequence of this clone (SEQ ID No:1) was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these cDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7-9 to northern blots from various tissues and cell lines revealed a major transcript of 12 kb, later shown to be 13 kb, in all tissues and cell types examined, and minor species of various sizes in several tissues, possibly representing alternatively spliced transcripts of the corresponding gene or other homologous sequences. Genomic sequencing later identified the 5' non-coding region of clone 7-9 as sequences of the unspliced adjacent intron. Two other cDNA clones from a leukocyte cDNA library were found to contain this intronic sequence in their 5' ends. These clones may represent splicing intermediates.

Figure 2:
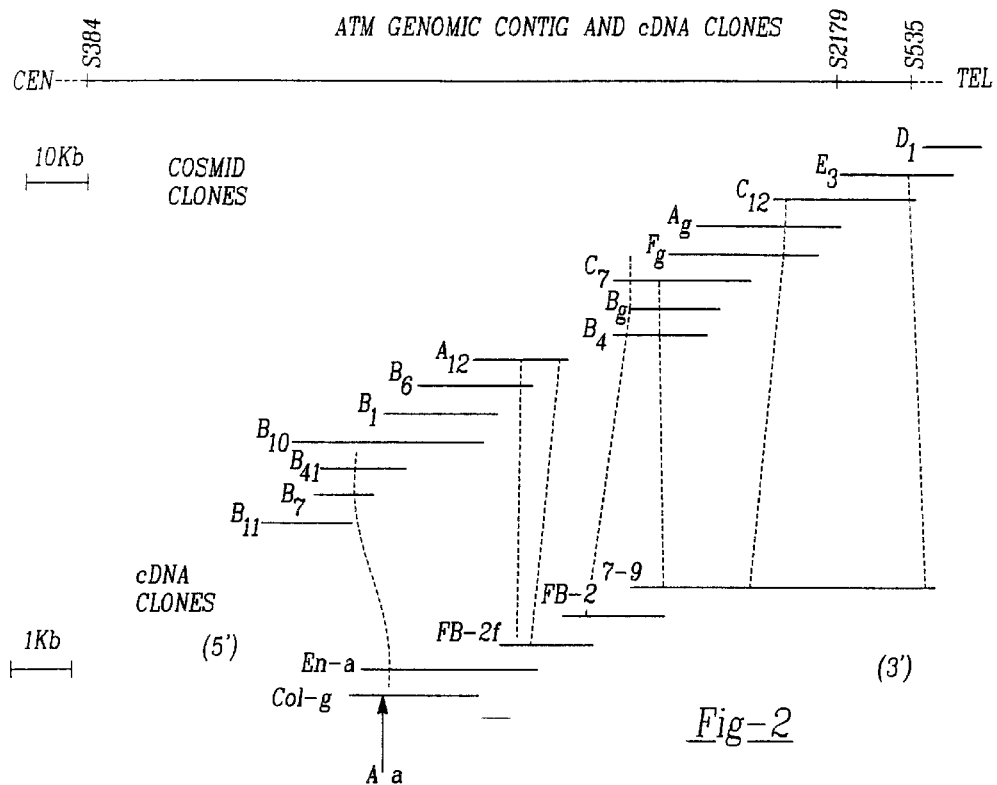
FIG. 2 is a diagram of the physical map of the ATM region and relationship to the cDNA wherein the top line represents a linear map of the region containing known genetic markers (the prefix D11 has been omitted from marker designations) and shown below the linear map is a portion of a cosmid contig spanning the region with the arch between ends of cosmids A12 and B4 represents a genomic PCR product, a contig of cDNA clones which span the ATM ORF is shown at the bottom of the figure, broken lines denote the position of specific cDNA sequences with the cosmid contig.

The 7-9 cDNA clone represents only part of the ATM gene transcript. Successive screening of randomly-primed cDNA libraries identified a series of partly overlapping cDNA clones and enabled the construction of a cDNA contig of about 10 Kb (FIG. 2). The gene coding for this transcript spans about 150 Kb of genomic DNA.

The composite cDNA of 9860 bp (GenBank Accession No. U33841; SEQ ID No:2) includes an open reading frame of 9168 nucleotides, a 538 bp 3' untranslated region (UTR), and a 164 bp 5' UTR containing stop codons in all reading frames. The sequence surrounding the first in-frame initiation codon (ACC<u>ATG</u>A) resembles the consensus sequence proposed by Kozak for optimal initiation of translation, (A/G)CC<u>ATG</u>G (ref. 20 in Savitsky et al, 1995b). No polyadenylation signal was found at the 3' UTR. The same poly(A) tail was found in all cDNA clones and 3' RACE products isolated to date in applicant's laboratory, however, this poly(A) tail most likely belongs to the Alu element contained in the 3' UTR.

Sequencing and PCR analysis of 32 partial ATM cDNA clones, obtained from 11 cDNA libraries representing 8 different tissues, have been colinear over the coding region, except when they contained unspliced intronic sequences. Thus, alternative splicing within the ATM coding region may not occur, or may take place at a very low frequency, or be restricted to a cell type not yet explored.

The invention further provides a purified protein (SEQ ID No:3) as encoded by the ATM gene and analogs and mutations thereof (SEQ ID No:2). The present invention further provides for mutations in SEQ ID No:3 which cause ataxia-telangiectasia, for example, as set forth in Tables 2 and 3.

This product of the ATM Open Reading Frame (SEQ ID No:2) is a large protein of 3056 amino acids, with an expected molecular weight of 350.6 kDa. The ATM gene product (SEQ ID No:3) contains a PI-3 kinase signature at codons 2855–2875, and a potential leucine zipper at codons 1217–1238. The presence of this leucine zipper may suggest possible dimerization of the ATM protein or interaction with additional proteins. No nuclear localization signal, transmembrane domains or other motifs were observed in this protein sequence.

The ATM gene product is a member of a family of large proteins that share a highly conserved carboxy-terminal region of about 300 amino acids showing high sequence homology to the catalytic domain of PI-3 kinases. Among these proteins are Tel1p and Mec1p in budding yeast, rad3p in fission yeast, the TOR proteins in yeast and their mammalian counterpart, FRAP (RAFT1), MEI-41 in *Drosophila melanogaster*, and the catalytic subunit of DNA-dependent protein kinase (DNA-PKcs) in mammals. All of these proteins are implicated in cell cycle control and some of them, like Mec1p, rad3p and DNA-PKcs are involved in response to DNA damage (Table 4). The central core of the PI-3 kinase-like domain contains two subdomains with highly conserved residues present in nearly all kinases, including protein and PI-3 kinases. The residues Asp and Asn (at positions 2870 and 2875 in ATM), and the triplet Asp-Phe-Gly (at positions 2889–2891), which represents the most highly conserved short stretch in the protein kinase catalytic domain, have been implicated in the binding of ATP and phosphotransferase activity. Mutations in the genes encoding these proteins result in a variety of phenotypes that share features with A-T, such as radiosensitivity, chromosomal instability, telomere shortening, and defective cell cycle checkpoints (reviewed by Savitsky et al., 1995a and b; Zakian, 1995).

A possible working model for the ATM protein's function is DNA-PK, a serine/threonine protein kinase that is activated in vitro by DNA double-strand breaks and responds by phosphorylating several regulatory proteins (Gottlieb and Jackson, 1994). The ATM protein may be responsible for conveying a signal evoked by a specific DNA damage to various checkpoint systems, possibly via lipid or protein phosphorylation.

The present invention further includes a recombinant protein encoded by SEQ ID No:2 or SEQ ID No:3. This recombinant protein is isolated and purified by techniques known to those skilled in the art.

An analog will be generally at least 70% homologous over any portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to epitopes on the polypeptide/protein encoded by the ATM gene or mutant epitopes. In preparing the antibody, the protein (with and without mutations) encoded by the ATM gene and polymorphisms thereof is used as a source of the immunogen. Peptide amino acid sequences isolated from the amino acid sequence as set forth in SEQ ID No:3 or mutant peptide sequences can also be used as an immunogen.

The present invention also provides antibodies against the following peptides:
HEPANSSASQSTDLC (SEQ ID No:4),
CKRNLSDIDQSFDKV (SEQ ID No:5),
PEDETELHPTLNADDQEC (SEQ ID No:6), and
CKSLASFIKKPFDRGEVESMEDDTNG (SEQ ID No: 7).

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual,* Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use. The antibody can be bound to a solid support substrate or conjugated with a detectable moiety or be both bound and conjugated as is well known in the art. (For a general discussion of conjugation of fluorescent or enzymatic moieties see Johnstone and Thorpe, *Immunochemistry in Practice,* Blackwell Scientific Publications, Oxford, 1982.) The binding of antibodies to a solid support substrate is also well known in the art. (see for a general discussion Harlow and Lane *Antibodies: A Laboratory Manual,* Cold Spring Harbor Laboratory Publications, N.Y., 1988). The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}$C and iodination.

The present invention provides vectors comprising an expression control sequence operatively linked to the nucleic acid sequence of the ATM gene, SEQ ID No:2 and portions thereof as well as mutant sequences which lead to the expression of A-T. The present invention further provides host cells, selected from suitable eucaryotic and procaryotic cells, which are transformed with these vectors.

Using the present invention, it is possible to transform host cells, including *E. coli,* using the appropriate vectors so that they carry recombinant DNA sequences derived from the ATM transcript or containing the entire ATM transcript in its normal form or a mutated sequence containing point mutations, deletions, insertions, or rearrangements of DNA. Such transformed cells allow the study of the function and the regulation of the A-T gene. Use of recombinantly transformed host cells allows for the study of the mechanisms of A-T and, in particular it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1992), in Ausubel et al., *Current Protocols in Molecular Biology,* John Wiley and Sons, Baltimore, Md. (1989), Chang et al., *Somatic Gene Therapy,* CRC Press, Ann Arbor, Mich. (1995), Vega et al., *Gene Targeting,* CRC Press, Ann Arbor, Mich. (1995) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. See also U.S. Pat. Nos. 5,487,992 and 5,464,764. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that exhibit the phenotypic manifestations of A-T. The present invention provides for transgenic ATM gene and mutant ATM gene animal and cellular (cell lines) models as well as for knockout ATM models. The transgenic models include those carrying the sequence set forth SEQ ID Nos:2,8,9 (or 10). These models are constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information. See also in general Hogan et al "Manipulating the Mouse Embryo" Cold Spring Harbor Laboratory Press, 2nd Edition (1994).

According to the present invention, there is provided a method for diagnosing and detecting carriers of the defective gene responsible for causing A-T. The present invention further provides methods for detecting normal copies of the ATM gene and its gene product. Carrier detection is especially important since A-T mutations underlie certain cases of cancer predisposition in the general population. Identifying the carriers either by their defective gene or by their missing or defective protein(s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

Briefly, the methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

More specifically, the method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins from a cell line established from the subject) with appropriate primers derived from the gene sequence by techniques well known in the art. The PCR product would then be tested for the presence of appropriate sequence variations in order to assess genotypic A-T status of the subject.

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase—polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Tables 2 and 3) indicate that A-T is a disease characterized by considerable allelic heterogenicity. It is not surprising that there are hundreds (or even thousands) of ATM mutations (as is the case for cystic fibrosis and BRCA1) as shown in Table 3. Thus, it will be important for a successful mutation screen to be able to detect all possible nucleotide alterations in the ATM gene, rather than being focused on a limited subset. Methods including direct sequencing of PCR amplified DNA or RNA or DNA chip hybridization (Fodor et al., 1993; Pease et al., 1994) can be applied along with other suitable methods known to those skilled in the art.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook, 1992) which can be detected by methods well known in the art such as autoradiography. Oligomer probes can also be labelled by non-radioactive methods such as chemiluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

Functional assays can be used for detection of A-T carriers or affected individuals. For example, if the ATM protein product is shown to have PI 3-kinase or a protein kinase biochemical activity which can be assayed in an accessible biological material, such as serum, peripheral leukocytes, etc., then homozygous normal individuals would have approximately normal biological activity and serve as the positive control. A-T carriers would have substantially less than normal biological activity, and affected (i.e. homozygous) individuals would have even less biological activity and serve as a negative control. Such a biochemical assay currently serves as the basis for Tay-Sachs carrier detection.

The present invention also provides a kit for diagnosis and detection of the defective A-T gene in a population. In general the population will be one that has been characterized for ATM mutations. For example Moroccan Jews in which only one mutation is known, or a population such as the Amish in which also one mutation is known. Each kit would be customized to the population being screened. The kit includes a molecular probe(s) complementary to genetic sequences of the defective gene which causes ataxia-telangiectasia (A-T) in that population and suitable labels for detecting hybridization of the molecular probe and the defective gene thereby indicating the presence of the defective gene. The molecular probe has a DNA sequence complementary to mutant sequences. Alternatively, the kit can contain reagents and antibodies for detection of mutant proteins.

The above discussion provides a factual basis for the use and identification of the ataxia-telangiectasia gene and gene products and identification of carriers as well as construction of transgenic organisms. The methods used in the present invention can be shown by the following non-limiting example and accompanying figures.

EXAMPLES

Materials and Methods

General methods in molecular biology: Standard molecular biology techniques known in the art and not specifically described were generally followed as in Sambrook et al., *Molecular Cloning: A Laboratory Manual,* Cold Springs Harbor Laboratory, New York (1989, 1992), and in Ausubel et al., *Current Protocols in Molecular Biology,* John Wiley and Sons, Baltimore, Md. (1989).

Patient and family resources: A cell line repository was established containing 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who have also established extensive repositories of A-T families. Linkage analysis was conducted on a pool of 176 families.

Example 1

Definition of the A-T interval by genetic analysis: Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994a; McConville et al., 1994) (see also Shiloh, 1995, and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. These experiments led to the localization of 12 microsatellites at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers is a useful tool for the fine localization of disease genes (Chakravarti et al., 1984; Kerem et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD ($p<0.02$–$p<0.001$) between A-T and markers along the D11S1817–D11S927 region in the patients of the sixteen Moroccan-Jewish A-T families identified in Israel (Oskato et al., 1993). Further analysis with the new markers narrowed the peak of linkage disequilibrium to the D11S384–D11S1818 region as shown in FIG. 1.

Haplotype analysis indicated that all of the mutant chromosomes carry the same D11S384–D11S1818 haplotype, suggesting a founder effect for A-T in this community, with one mutation predominating.

Example 2

Sequencing the ATM Gene

Cloning the disease locus in a contig (set of overlapping clones) was essential in isolating the A-T disease gene. The entire A-T locus and flanking region in a contig of yeast artificial chromosomes (YACS) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384–D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene: Transcribed sequences were systematically identified based on two complementary methods:

1. Use of an improved direct selection method based on magnetic bead capture (MBC) of cDNAs corresponding to genomic clones (Morgan et al., 1992; Tagle et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0–1.5 Kb fraction was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the initial identification and isolation of a cDNA clone designated 7-9 (Savitsky et al, 1995a), the complete sequence of which is set forth in SEQ ID No:1 and which is derived from a gene located under the peak of cumulative location score obtained by linkage analysis as shown in FIG. 1. The gene extends over some 300 kilobases (kb) of genomic DNA and codes for two major mRNA species of 12 kb and 10.5 kb in length. The 7-9 clone is 5.9 kb in length and, therefore, is not a full length clone.

An open reading frame of 5124 bp within this cDNA encodes a protein with signature motifs typical of a group of signal transduction proteins known as phosphatidylinositol 3-kinases (PI 3-kinases). PI 3-kinases take part in the complex system responsible for transmitting signals from the outer environment of a cell into the cell. It is not clear yet whether the protein product of the corresponding gene encodes a lipid kinase or a protein kinase.

The gene encoding the 7-9 cDNA clone was considered a strong A-T candidate and mutations were sought in patients. Southern blotting analysis revealed a homozygous deletion in this gene in affected members of Family N., an extended Palestinian Arab A-T family which has not been assigned to a specific complementation group. All the patients in this family are expected to be homozygous by descent for a single A-T mutation. The deletion includes almost the entire genomic region spanned by transcript 7-9, and was found to segregate in the family together with the disease. This finding led to a systematic search for mutations in the 7-9 transcript in additional patients, especially those previously assigned to specific complementation groups.

The restriction endonuclease fingerprinting (REF) method (Liu and Sommer 1995) was applied to reverse-transcribed and PCR-amplified RNA (RT-PCR) from A-T cell lines. Observation of abnormal REF patterns was followed by direct sequencing of the relevant portion of the transcript and repeated analysis of another independent RT product. In compound heterozygotes, the two alleles were separated by subcloning of RT-PCR products and individually sequenced. Genomic sequencing was conducted in some cases to confirm the sequence alteration at the genomic level. Additional family members were studied when available.

Ten sequence alterations (Table 2) were identified in the 7-9 transcript in 13 A-T patients including two sibling pairs. Most of these sequence changes are expected to lead to premature truncation of the protein product, while the rest are expected to create in-frame deletions of 1–3 amino acid residues in this protein. While the consequences of the in-frame deletions remain to be investigated, it is reasonable to assume that they result in impairment of protein function. In one patient, AT3NG, the loss of a serine residue at position 1512 occurs within the PI3-kinase signature sequence. This well conserved domain is distantly related to the catalytic site of protein kinases, hence this mutation is likely to functionally affect the 7-9 protein.

In view of the strong evidence that mutations in this gene are responsible for A-T, it was designated ATM (A-T, Mutated). Since these patients represent all complementation groups of the disease and considerable ethnic variability, these results indicate that the ATM gene alone is responsible for all A-T cases.

In order to complete the cloning of the entire ATM open reading frame, fetal brain and colon random-primed libraries obtained from Stratagene (San Diego, Calif.) and an endothelial cell random-primed library (a gift of Dr. David Ginsburg, University of Michigan) were screened. A total of $1 \times 10^6$ pfu were screened at a density of 40,000 pfu per 140 mm plate, and replicas were made on Qiabrane filters (Qiagen), as recommended by the manufacturer. Filters were prehybridized in a solution containing 6×SSC, 5× Denhardt's, 1% N-laurylsarcosyl, 10% dextran sulfate and 100 µg/ml salmon sperm DNA for 2 hours at 65° C. Hybridization was performed for 16 hrs under the same conditions with $1 \times 10^6$ cpm/ml of $^{32}$P-labelled probe, followed by final washes of 30 minutes in 0.25×SSC, 0.1%

SDS at 60° C. Positive clones were plaque-purified using standard techniques and sequenced. DNA sequencing was performed using an automated DNA sequencer (Applied Biosystems, model 373A), and the sequence was assembled using the AutoAssembler program (Applied Biosystems Division, Perkin-Elmer Corporation). In the final sequence, each nucleotide represents at least four independent readings in both directions.

Database searches for sequence similarities were performed using the BLAST network service. Alignment of protein sequences and pairwise comparisons were done using the MACAW program, and the PILEUP and BESTFIT programs in the sequence analysis software package developed by the Genetics Computer Group at the University of Wisconsin.

Example 3

Detection of Mutations

Determination of mutations: The recently discovered ATM gene is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

Materials and Methods

RT-PCR: Total RNA was extracted from cultured fibroblast or lymphoblast cells using the Tri-Reagent system (Molecular research Center, Cincinnati, Ohio). Reverse transcription was performed on 2.5 ug of total RNA in a final volume of 10 ul, using the Superscript II Reverse Transcriptase (Gibco BRL, Gaithersburg, Md.) in the buffer recommended by the supplier, and in the presence of 125 U/ml of RNAsin (Promega) and 1 mM dNTPs (Pharmacia). Primers were either oligo(dT) (Pharmacia) or a specifically designed primer. The reaction products were used as templates for PCR performed with specific primers. These reactions were carried out in 50 $\mu$l containing 2 units of Taq DNA Polymerase (Boehringer Mannheim, Mannheim, Germany), 200 $\mu$M dNTPs, 0.5 $\mu$M of each primer, and one tenth of the RT-PCR products. The products were purified using the QIA-quick spin system (Qiagen, Hilden, Germany).

Restriction endonuclease fingerprinting: The protocol of Liu and Sommer (1995) was followed with slight modifications. RT-PCR was performed as described above, using primers defining PCR products of 1.0–1.6 kb. One hundred ng of amplified DNA was digested separately with 5 or 6 restriction endonucleases in the presence of 0.2 units of shrimp alkaline phosphatase (United States Biochemicals, Cleveland, Ohio). Following heat inactivation at 65° C. for 10 minutes, the digestion products corresponding to the same PCR product were pooled, denatured at 96° C. for 5 minutes and immediately chilled on ice. Ten ng of this fragment mixture was labeled in the presence of 6 $\mu$Ci of [$\gamma$-$^{33}$P]ATP and 1 unit of T4 polynucleotide kinase (New England Biolabs, Beverly, Mass.) at 37° C. for 45 minutes. Twenty $\mu$l of stop solution containing 95% formamide, 20 mM EDTA, 0.05% bromophenol blue, 0.05% xylene cyanol, and 10 mM NaOH were added, and the samples were boiled for 3 minutes and quick-chilled on ice. Electrophoresis was performed in 5.6% polyacrylamide gels in 50 mM Tris-borate, pH 8.3, 1 mM EDTA at constant power of 12 W for 3 hours at room temperature, with a fan directed to the glass plates, keeping them at 22–24° C. The gels were dried and subjected to autoradiography.

Direct sequencing of PCR products: Five hundred ng of PCR products was dried under vacuum, resuspended in reaction buffer containing the sequencing primer, and the mixture was boiled and snap-frozen in liquid nitrogen. The Sequenase II system (Unites States Biochemicals) was used to carry out the sequencing reaction in the presence of 0.5 $\mu$g of single-strand binding protein (T4 gene 32 protein, United States Biochemicals). The reaction products were treated with 0.1 $\mu$g of proteinase K at 65° C. for 15 minutes, separated on a 6% polyacrylamide gel, and visualized by autoradiography.

Using the methods described herein above the ATM transcript was scanned for mutations in fibroblast and lymphoblast cell lines derived from an extended series of A-T patients from 13 countries, all of whom were characterized by the classical A-T phenotype. The analysis was based on RT-PCR followed by restriction endonuclease fingerprinting (REF). REF is a modification of the single-strand conformation polymoprphism (SSCP) method, and enables efficient detection of sequence alterations in DNA fragments up to 2 kb in length (Liu and Sommer, 1995).

Briefly, after PCR amplification of the target region, multiple restriction endonuclease digestions are performed prior to SSCP analysis, in order to increase the sensitivity of the method and enable precise localization of a sequence alteration within the analyzed fragment. The coding sequence of the ATM transcript, which spans 9168 nucleotides (SEQ ID No:2) (Savitsky et al., 1995b), was thus divided into 8 partly overlapping portions of 1.0–1.6 Kb, and each one was analyzed separately. Sequence alterations causing abnormal REF patterns were located and disclosed by direct sequencing. Mutations identified in this way were reconfirmed by repeating the RT-PCR and sequencing, or by testing the presence of the same mutations in genomic DNA.

In compound heterozygotes, the two alleles were separated by subcloning and individually sequenced. In some cases, agarose gel electrophoresis showed large deletions in the ATM transcript manifested as RT-PCR products of reduced sizes. The breakpoints of such deletions were delineated by direct sequencing of these products.

The 44 mutations identified to date in our patient cohort (Table 3, FIG. 4) include 34 new ones and 10 previously identified ones (Table 2). (Mutations in Table 3 are presented according to the nomenclature proposed by Beaudet & Tsui (1993); nucleotide numbers refer to their positions in the sequence of the ATM transcript (accession number U33841); the first nucleotide of the open reading frame was designated +1.) These mutations were found amongst 55 A-T families: many are unique to a single family, while others are shared by several families, most notably the 4 nt deletion, 7517del4, which is common to 6 A-T families from South-Central Italy (Table 3). According to this sample, there is a considerable heterogeneity of mutations in A-T, and most of them are "private". The proportion of homozygotes in this sample is relatively high due to a high degree of consanguinity the populations studied. It should be noted, however, that apparently homozygous patients from non-consanguineous families may in fact be compound heterozygotes with one allele not expressed.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. This phenomenon usually results from sequence alterations at splice junctions or within introns, or mutations within the skipped exons, mainly of the nonsense type (Cooper and Krawczak, 1993; Sommer, 1995; Steingrimsdottir et al., 1992; Gibson et al., 1993; Dietz and Kendzior, 1994). One large deletion spans about 7.5 Kb of the transcript and represents a genomic deletion of about 85 Kb within the ATM gene. Of these deletions and insertions, 25 are expected to result in frameshifts. Together with the 4 nonsense mutations, truncation mutations account for 66% of the total number of mutations in this sample. Seven in-frame deletions span long segments (30–124 aa) of the protein, and similarly to the truncation mutations, are expected to have a severe effect on the protein's structure. It should be noted that two base substitutions abolish the translation initiation and termination codons. The latter is expected to result in an extension of the ATM protein by an additional 29 amino acids. This mutation may affect the conformation of the nearby PI 3-kinase-like domain.

While the effect of the 4 small (1–3 aa) in-frame deletions and insertions on the ATM protein remains to be studied, it should be noted that one such deletion (8578de13) leads to a loss of a serine residue at position 2860. This amino acid is part of a conserved motif within the PI 3-kinase-like domain typical of the protein family to which ATM is related, and is present in 7 of 9 members of this family. The single missense mutation identified in this study, which leads to a Glu2904Gly substitution, results in a nonconservative alteration of another extremely conserved residue within this domain, which is shared by all of these proteins. The patient homozygous for this mutation, AT41RM, shows the typical clinical A-T phenotype. Measurement of radioresistant DNA synthesis in the patient's cell line revealed a typical A-T response, demonstrating that this patient has the classical A-T cellular phenotype.

As discussed herein above, the ATM gene of the present invention is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

A technical explanation for this bias towards deletions and insertions could be a greater ability of the REF method to detect such lesions versus its ability to detect base substitution. Liu and Sommer (1995) have shown, however, that the detection rate of this method in a sample of 42 point mutations in the factor IX gene ranged between 88% and 100%, depending on the electrophoresis conditions. The 7 base substitutions detected directly by the REF method in the present study (Table 2), indicate that such sequence alterations are detected in our hands as well.

Since the expected result of most of these mutations is complete inactivation of the protein, this skewed mutation profile might represent a functional bias related to the studied phenotype, rather than a structural feature of the ATM gene that lends itself to a particular mutation mechanism. The classical A-T phenotype appears to be caused by homozygosity or compound heterozygosity for null alleles, and hence is probably the most severe expression of defects in the ATM gene. The plethora of missense mutations expected in the large coding region of this gene is probably rarely represented in patients with classical A-T, unless such a mutation results in complete functional inactivation of the protein. By inference, the only missense identified in this study, Glu2940Gly, which substitutes a conserved amino acid at the PI 3-kinase domain and clearly gives rise to a classical A-T phenotype, points to the importance of this domain for the biological activity of the ATM protein. Mutations in this domain abolish the telomere-preserving function of the TELL protein in S. cerevisiae (Greenwell et al., 1995), a protein which shows a particularly high sequence similarity to ATM (Savitsky et al., 1995b; Zakian, 1995). Another member of the family of PI 3-kinase-related proteins that includes ATM is the mammalian FRAP. Mutations in the PI 3-kinase domain abolish its autophosphorylation ability and biological activity (Brown et al., 1995). These observations, together with the mutation shown here, suggest that this domain in ATM is also likely to include the catalytic site, which may function as a protein kinase.

Genotype-phenotype relationships associated with the ATM gene appear therefore to extend beyond classical A-T. There are several examples of genes in which different mutations lead to related but clinically different phenotypes. For example, different combinations of defective alleles of the ERCC2 gene may result in xeroderma pigmentosum (group D), Cockayne's syndrome or trichothiodystrophy—three diseases with different clinical features involving UV sensitivity (Broughton et al., 1994, 1995).

Different mutations in the CFTR gene may lead to full-fledged cystic fibrosis, or only to congenital bilateral absence of the vas deferens which is one feature of this disease (Chillon et al., 1995; Jarvi et al., 1995). A particularly interesting example is the X-linked WASP gene responsible for Wiskott Aldrich syndrome (WAS), characterized by immunodeficiency, eczema and thrombocytopenia. Most of the mutations responsible for this phenotype cause protein truncations; however, certain missense mutations may result in X-linked thrombocytopenia, which represents a partial WAS phenotype, while compound heterozygosity for a severe and mild mutation results in females in an intermediate phenotype (Kolluri et al., 1995; Derry et al., 1995).

In a similar manner, genotypic combinations of mutations with different severities create a continuous spectrum of phenotypic variation in many metabolic diseases.

Which phenotypes are most likely to be associated with milder ATM mutations? Since cerebellar damage is the early and severe manifestation of A-T, it is reasonable to assume that the cerebellum might also be affected to some extent in phenotypes associated with milder ATM mutations. Such phenotypes may include cerebellar ataxia, either isolated (Harding, 1993) or coupled with various degrees of immunodeficiency. The latter combination has indeed been described, sometimes with chromosomal instability, and is often designated "ataxia without telangiectasia" (Ying and Decoteau, 1983; Byrne et al., 1984; Aicardi et al., 1988; Maserati, 1988; Friedman and Weitberg, 1993). Friedman and Weitberg (1993) recently suggested a new clinical category of "ataxia with immune deficiency" that would include A-T as well as other cases of cerebellar degeneration with immune deficits. Evaluation of patients with cerebellar disorders with the present invention may reveal a higher frequency of such cases than previously estimated. However, in view of the pleiotropic nature of the ATM gene, the range of phenotypes associated with various ATM genotypes may be even broader, and include mild progressive conditions not always defined as clear clinical entities. Screening for mutations in this gene in such cases may reveal wider boundaries for the molecular pathology associated with the ATM gene.

Example 4

Determination of Genomic Organization

The exon/intron boundaries and the intron sizes were determined using long-distance PCR (Barnes, 1994; Cheng et al., 1994; Foord and Rose, 1994). Primers were designed based on the ATM cDNA sequence (Savitsky et al., 1995a,b) at 200–300 bp intervals. Templates for these reactions were cosmid and YAC clones, and human genomic DNA. PCR products were obtained in all cases, including those that span the largest intron, of 11 kb. In the large majority of cases, PCR products of the same size were obtained with all templates, and those obtained from genomic DNA were used for sequencing of the exon-intron junctions. Following initial reactions, new primers were designed as needed, based on the evolving knowledge of the gene structure. Exon-intron boundaries were determined at the sites where genomic and cDNA sequences diverged. Typical splice acceptor and donor sequences were found around these sites in all cases. During the search for the A-T gene, six exons were isolated by exon trapping (Shiloh et al., 1994b) using the vectors pSPL3 (Church et al., 1994) and éGET (Nehls et al., 1994a,b). Their boundaries coincided with those obtained by long-distance PCR.

Parallel with these experiments, an effort was initiated to sequence the entire ATM gene (Example 5). The sequence of one cosmid, B10, was the first completed. This cosmid spans a portion of the gene containing the first 10 exons and upstream sequences. Comparison of this genomic sequence to the cDNA sequence yielded exon boundaries which coincided with those obtained by long-distance genomic PCR as seen in Table 1.

The ATM gene is composed of 66 exons (FIG. 3 and Table 1). The first two exons are alternatively spliced, and are designated 1a (SEQ ID No:10) and 1b (SEQ ID No:9). With the exception of the 3' exon, ATM exons range in size from 64 to 372 bp, with an average of 149 bp. The introns vary considerably in size, from 100 bp to about 11 kb, with the majority in the range of 1–3 kb. The consensus dinucleotides GT and AG were found at the donor and acceptor splice sites of all introns, except for a variant donor site with a GC dinucleotide (reviewed in Jackson, 1991) present in the intron 3' to exon 51. The first methionine of the open reading frame is located in exon 3, whereas the stop codon is located in the 3' and largest exon of 3.6 kb. This exon includes a 3' untranslated region (UTR)(SEQ ID No:8) of about 3400 nucleotides.

The ATM gene contains one of the largest number of exons reported to date for a human gene. However, these exons are spread over a relatively compact genomic region of about 150 kb. The dystrophin gene, for example, consists of 79 exons spanning 2.4 Mb of genomic DNA (Roberts et al., 1993), while the Huntington's disease gene consists of 67 exons spread over 180 Kb (Ambrose et al., 1994b).

Example 5

Determination of Genomic Sequence of ATM Gene

The complete genomic sequence is set forth in SEQ ID No:11. The cosmid contig shown in FIG. 1C was sequenced using automated sequencing equipment. The entire sequence of 170 kb of DNA containing the ATM gene was obtained. Alignment of the genomic sequence with the cDNA sequence, as shown in Table 5, confirmed the exon-intron boundaries obtained as shown in Example 4. In Table 5, the alignment format will be as follows:

```
        intron      exon        intron      exon
cDNA:   ...........AGCTATAG..........TACATGA.....
genomic AAATGCTTCTTAGCTATAGACTTGCTTATTTACATGACCT
```

Throughout this application various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

EXON-INTRON ORGANIZATION OF THE ATM GENE

| Exon No. | 5" intronic sequence | Exon First Base* | Exon length (bp) | Exon Last Base* | 3" intronic sequence | Size of 3"intron (kb) |
|---|---|---|---|---|---|---|
| 1a§ |  |  | AGGTAG | 120 | GCAGTG | -915 | -796 | gtaggggcgcggagcaacgcagcgcttc | 0.18 |
| 1b§ | tgatcattgctaacattgctgtgtttcag | TCCTCC | 634 | TACCAG | -795 | -162 | gtatgagcggaagaagagatcaggagac | 0.09 |
| 2 | ttttctattactgtgttttgttcctcag | GCACTG | 43 | ATAGAG | -161 | -119 | gtaggtactagtattgttttcctttatc | 0.65 |
| 3 | tatatataccatatgtatttttttacag | AGGCAT | 88 | ATGAGG | -118 | -31 | gtaggatttgtatctgtttagttcattat | 2.75 |
| 4 | aacccattattattcctttttattttcag | ACAGTG | 102 | CGAAAG | -30 | 72 | gtagtaattactaattcattttttcct | 0.08 |
| 5 | tttctgaaattgcatttgtttcttgaag | AAAGAA | 113 | TTTTAG | 73 | 185 | gtattcattcaaatttatttactgtctt | 1.30 |
| 6 | gttttcttattgttaatttgttatttcag | ATTTTT | 146 | ACAGAA | 186 | 331 | gtaagtgtgttataattataataatggc | 6.35 |
| 7 | catgactaataatttttttttttttag | GAGCAC | 165 | GGTTAG | 332 | 496 | gtatgtttgaaggtgtgtttgtgaattt | 8.10 |
| 8 | cccagtgagctgtgttgtttctcacag | AATTGT | 166 | TGCGAG | 497 | 662 | gtaatcaatctctttttcttttgttttgtattg | 0.67 |
| 9 | aaaattacatttaattttttgattacag | ACAAGA | 239 | AAAAAG | 663 | 901 | gtataaggaatgtttactgtttgaattt | 1.94 |
| 10 | gaaaaaagtggattttatttttatttcag | GTGCTT | 164 | CACCAG | 902 | 1065 | gtacagtaagtaggtcatgtcacatttaga | 1.80 |
| 11 | ttcaaataacccttttgtcttttttttag | GTTTTT | 170 | GCCTTG | 1066 | 1235 | gtaaagtgttaccatttctcattcagtgt | 1.60 |
| 12 | ttttcacaattgtccttgtttgttatag | GCTACA | 372 | TTCATG | 1236 | 1607 | gtaagttcagcatgcattagcatgctgctgtt | 0.80 |
| 13 | ctaagtgaagcttttgtttttcttgtag | TCCTGC | 195 | TCACAG | 1608 | 1802 | gtaatttaagtcattagcatgctgctgtt | 0.80 |
| 14 | ttatattaaagatcttactcttctgaag | TAATTT | 96 | AGAATG | 1803 | 1899 | gtatgttatctaataatgctcttatcatt | 0.90 |
| 15 | tatattttttattgtggttacttaag | TGAACA | 226 | TCTGAG | 1899 | 2124 | gtgagattttttaaaaagaactaagctt | 2.20 |
| 16 | aatttgcatttttccttctattcacaatag | ATTACA | 126 | GCCAAC | 2125 | 2250 | gtaggagaattttatactaataaagtttcgg | 1.15 |
| 17 | ttgcttggtctttgttgtcttaattgcag | TCTCTA | 126 | ACCAAG | 2251 | 2376 | gtaagatttttcttcttcttgtttttt | 1.40 |
| 18 | cttgaacatcttttgttctctcttgaag | AAGAGT | 90 | AGTTTA | 2377 | 2466 | gtaatatgcttcctgttttgctatcatat | 8.10 |
| 19 | ttagtgttaatgagtgctgttttattttag | GCATCC | 172 | CCATAG | 2467 | 2638 | gtaaatacatattactacttggatttct | 1.10 |
| 20 | cctgattttttccctcctaccatcttag | GTGCCA | 200 | CATATG | 2639 | 2838 | gtggttacgttaaatgaagaagctcttgg | 2.50 |
| 21 | aagtgaactttttttttttttttaccacag | TATCTA | 83 | ACTATC | 2839 | 2921 | gtaagaaattaaaaccttatgttatgttca | 0.10 |
| 22 |  | CAATGT | 156 | ATTTTG | 2922 | 3077 | gtaggtacagctctatttgtggtcctatt | 1.20 |

TABLE 1-continued

EXON-INTRON ORGANIZATION OF THE ATM GENE

| Exon No. | 5" intronic sequence | Exon First Base* | Exon length (bp) | Exon Last Base* | 3" intronic sequence | size of 3"intron (kb) |
|---|---|---|---|---|---|---|
| 23 | tttaacttggaaactactgatttcag | 3078 | GCATCT | 76 | CTTGAG | 3153 | gtgagttttgcatttttagtaagatct | 0.10 |
| 24 | tcatatttaaccacagtgtctttcccgtag | 3154 | GCTGAT | 131 | CAATAG | 3284 | gtaatgggtcaaatattcatgaagtatttg | 7.00 |
| 25 | tttcattgtttcttcctcctgtcttaag | 3285 | ATTGTT | 118 | GAAATG | 3402 | gtaatttaagtaacatgtatttgctgtta | 1.30 |
| 26 | ttacaatttttttttaaattcttttaag | 3403 | TCCCAT | 174 | AAAAAG | 3576 | gtatatatggatgagtatttattagaagc | 1.50 |
| 27 | cttaacacattgactttttggttcgtgcag | 3577 | GTTTTA | 170 | CTATAG | 3746 | gtaagtttatacatgacatatgtgaaattt | 1.35 |
| 28 | aacctgtatttaaattttctatttttag | 3747 | ATCTTG | 247 | AAACAG | 3993 | gtatgcttcattttatgtactttcat | 3.01 |
| 29 | taaatatatttaatttgtgcccttgcag | 3994 | ATTGAT | 116 | TTCAGG | 4109 | gtatgtacattttaaactagagaactagc | 1.30 |
| 30 | tgactgtatttttccccttaactctgttag | 4110 | GGATTT | 127 | AGCCCT | 4236 | gtaagtacatgatgagttaataataga | 0.50 |
| 31 | aagttttactaaatctgttatttctag | 4237 | GATTCC | 200 | CCAAAG | 4436 | gtaaataacatattagaccaataatataag | 2.80 |
| 32 | ttgttgtgttttttttctccctatattag | 4437 | GCCTTC | 175 | AAACAG | 4611 | gtaatttctgactcatctcaaaatggta | 0.52 |
| 33 | tataattttttctttttaaattatatttag | 4612 | GTATTG | 165 | TTGGAG | 4776 | gtaataaaattcatcatctactattttt | 1.45 |
| 34 | gttaaaagcaagtacattttctctttag | 4777 | GAAATT | 133 | CTCAGG | 4909 | gtgctaatttaaatgacatggctattt | 2.25 |
| 35 | ttaaactaatttttaaaaatattctag | 4910 | ATAATC | 96 | TTCTAG | 5005 | gtaaactacagtcatgcgctgcgtgacattt | 2.35 |
| 36 | ctgaaatagaatttctatatgtag | 5006 | AGGCTG | 172 | AGATTG | 5177 | gtgagtatttattgataacctttatatgtaat | 1.76 |
| 37 | cttgataggcatttgaattgttttttcag | 5178 | TGTCAA | 142 | AAAAAG | 5319 | gtctcttaagtaataaatgttattgaata | 1.05 |
| 38 | atttcacatttttctaatccctttcttctag | 5320 | TTTTTA | 177 | TGTGAA | 5496 | gtaagaagattaatagtcctgataattc | 1.65 |
| 39 | tattggtggattttgttgtatatctag | 5497 | GTGAAA | 178 | ATTCAG | 5674 | gtattcattaattttaacattaatact | 3.05 |
| 40 | ggactgagggagatatttttgttgtcag | 5675 | AGTCAG | 88 | AAAGAG | 5762 | gtaatgaatgagtgttgcttcttacgttt | 2.15 |
| 41 | tgaatgacattatatctcatttttcttag | 5763 | ACCTTC | 156 | GAAAAG | 5918 | gtaatggaattagaattttggttttaa | 2.10 |
| 42 | cattaaaagaggtgttcttgtgacaaacag | 5919 | AAGTCT | 88 | TTACAG | 6006 | gtaaatattagaggctctattatttatgac | 3.30 |
| 43 | cttcattttgttgttccatgtttcag | 6007 | GATCTT | 89 | TACTAG | 6095 | gtaaattgcattttcaaacaacggtatag | 0.10 |
| 44 | cccaaagctattttcacaatctttcttatag | 6096 | ACTACG | 103 | ATTCAG | 6198 | gtacatttttcccagattggtaaagcca | 1.26 |
| 45 | aacttaaaacaataaccctgttag | 6199 | GCCTTG | 149 | CGTCAG | 6347 | gtaagaaatttgactgattttttttttt | 2.50 |

TABLE 1-continued

EXON-INTRON ORGANIZATION OF THE ATM GENE

| Exon No. | 5" intronic sequence | Exon First Base* | Exon length (bp) | Exon Last Base* | 3" intronic sequence | size of 3"intron (kb) |
|---|---|---|---|---|---|---|
| 46 | gtatattttttcttgactatctcacag | CAAAGA | 6348 | 105 | TGCCAG | gtattatgaaagacaaagtactgtatttt | 1.25 |
| 47 | tttcagagtgtcttttcttttgctactag | AGTAAA | 6453 | 120 | CTCAAG | gtatgtaattcgtatgactgttatccta | 4.00 |
| 48 | cttacatgaactctatgtcgtggcattcag | ATCAGT | 6573 | 235 | ACTCAG | gtaaatacaattaaactatgtcatctta | 4.00 |
| 49 | atttattcccatatgtcatttcatttcag | CTCCCT | 6808 | 168 | GCAGCG | gtttgttttttttattggctggattagtgt | 1.40 |
| 50 | tatatttaagatttgcctttctatacag | AACAAT | 6976 | 114 | GAAAAG | gtaagattttggagcaaccttaagatag | 1.30 |
| 51 | tataatttaaattggtgtgttttcttgaag | GCAGTA | 7090 | 218 | AAACAG | gtaactaggttctacaagtgacaattta | 1.00 |
| 52 | ttgtgtttacctaattattctatgcaag | ATACAC | 7308 | 208 | ATGAAG | gcaagtgttactcagcccaatattctaccc | 1.00 |
| 53 | cttaatttgtgtcttttttttaatggtag | AGAGAC | 7516 | 114 | AATAAT | gtaagtaaactgaaaatcaaaccacaata | 0.32 |
| 54 | tgcataaatctaatagtctcttttcttacag | CTAATC | 7630 | 159 | GATGAG | gtatttggattaaacatacgtacctttag | 0.70 |
| 55 | tatgtaatgtttttgttttttattaatag | GATCGA | 7789 | 139 | AGAGAA | gtatgttttttttaagaagaaacgttact | 1.00 |
| 56 | tcactaaaatctctcattttaaatacag | AAGGCA | 7928 | 83 | ATTAAG | gtaatttgcaattaactcttgatttttttt | 1.00 |
| 57 | ctattatcaatcatgttatactttttattag | GTGGAC | 8011 | 141 | GTTAAG | gtgagcctccctcctctcgtgcttagccctt | 0.80 |
| 58 | acttgtttattcatgcttaattattctgaag | GGCCGT | 8152 | 117 | TATAAG | gtaactatttgtacttctgttagttcacca | 7.50 |
| 59 | aattaaaagtattaatcgtaactccag | GTGGTT | 8269 | 150 | ATGATG | gtgagtgacaccaaaattaaaggtattg | 2.40 |
| 60 | aaaaattaatatatatctctatttaaag | GAGGTG | 8419 | 166 | CTATTG | gtaatctcttgtacatatagattgag | 1.40 |
| 61 | tttcagattgtttgtttctttttttccag | TTGGTT | 8585 | 87 | ATCTAG | gtaagtaataaatctatgtatctattctt | 6.00 |
| 62 | cctcctaacttcactgtattctttacttag | GTGTTG | 8672 | 115 | CAGAAG | gtaagtgatatgaagtaaggaggaat | 1.00 |
| 63 | atccgtatttataatgtgttttgactctag | ATGCTG | 8787 | 64 | GTAGAG | gtaaagtatttataaggaggaggactttatttt | 11.0 |
| 64 | aagaacagatctctctgttag | GTCCTT | 8851 | 137 | TCTCAG | gtgagcagtattttaagaaggtcctgttgt | 0.10 |
| 65 | actggaacctttgtgttttgtccttag | TGATAT | 8988 | ~3600 | | | |

*The first nucleotide of the open reading frame was designated +1. §1a and 1b are alternatively spliced 5" non-coding exons.

TABLE 2 illustrates several mutations found in A-T patients

| Patient[1] | Ethnic/geographic origin | Complementation group[4] | Mutation mRNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[5] | 1512 | Compound heterozygote |
| AT15LA | Philippine | A | Insertion, +A | Frameshift, truncation | 557 | Compound heterozygote |
| AT3LA[2] AT4LA[2] | African-American | C | Deletion of 139 nt[6]/ Deletion of 298 nt[6] | Frameshift, trunction | 1196 | Compound heterozygotes |
| AT2BR | Celtic/Irish | C | Deletion, 9 nt | Deletion, 3 residues | 1198-1200 | Homozygote |
| AT1ABR AT2ABR | Australian (Irish/British) | E | Deletion, 9 nt | Deletion, 3 residues | 1198-1200 | Homozygote |
| AT5BI[2] AT6BI[2] | Indian/English | D | Deletion, 6 nt | Deletion, 2 residues | 1079-1080 | Compound heterozygotes |
| F-2079[3] | Turkish | ND | Insertion, +C[8] | Frameshift, truncation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients in both of whom the same mutation was identified.
[3]Patient expected to be homozygous by descent for an A-T mutation.
[4]According to the methods of Jaspers et al. (1988) ND: not determined.
[5]An identical sequence change was observed in genomic DNA
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N.
[8]The deleted serine residue is located within the PI3-kinase signature sequence (1507–1527 of SEQ ID No:2).
[10]In all the compound heterozygotes, the second mutation is still unidentified.

TABLE 3

Mutations in the ATM gene in patients with classical A-T.

| mRNA sequence change[1] | Predicted protein alteration | Codon[8] | Patient | Ethnic/ geographical origin | Genotype[11] |
|---|---|---|---|---|---|
| Truncations and exon skipping deletions: | | | | | |
| 9001de1AG | Truncation | 3001 | 91RD90[9] | Turkish | Hmz |
| 8946insA | Truncation | 2983 | AT103LO | American | Hmz |
| 8307G->A | Trp->ter; truncation | 2769 | AT2SF | American | Compd Htz |
| 8283delTC | Truncation | 2762 | AT28RM | Italian | Compd Htz |
| 8269del403[2] | Truncation | 2758 | AT12RM | Italian | Hmz |
| 8269del1503 | Del, 50 aa | 2758 | F-2086 | Turkish | Compd Htz |
|  |  |  | GM9587 | American | Compd Htz |
| 8140C->T | Gln->ter; truncation | 2714 | IARC12/AT3 | French | Hmz |
| 7883del5 | Truncation | 2628 | ATF104 | Japanese | Hmz |
|  |  |  | JCRB316 | Japanese | Compd Htz |
| 7789del139/7630del298[4,b] | Truncation | 2544 | AT4LA | Carribean Black | Comp Htz |
| 7630del159[3] | Del, 53 aa | 2544 | F-2086 | Turkish | Compd Htz |
|  |  |  | AT13BER |  | Compd Htz |
| 7517del4 | Truncation | 2506 | AT43RM[10] | Italian | Hmz |
|  |  |  | AT59RM[10] | Italian | Hmz |
|  |  |  | AT22RM[10] | Italian | Hmz |
|  |  |  | AT57RM[10] | Italian | Compd Htz |
|  |  |  | AT7RM[10] | Italian | Compd Htz |
|  |  |  | AT8RM[10] | Italian | Compd Htz |
| 6573del5 | Truncation | 2192 | AT12ABR | Australian | Compd Htz |
| 6348del105[3] | Del, 35 aa | 2116 | IARC15/AT4 | French | Hmz |
| 6199del149[3] | Truncation | 2067 | WG1101 | Canadian | Hmz |
| 5979del5 | Truncation | 1994 | AT5RM | Italian | Compd Htz |
| 5712insA | Truncation | 1905 | AT15LA | Philippino | Compd Htz |
| 5554insC | Truncation | 1852 | F-2079[9] | Turkish | Hmz |
| 5539del11 | Truncation | 1847 | AT2RO[9] | Arab | Hmz |
| 5320del355[6] | Truncation | 1774 | AT7RM | Italian | Compd Htz |
| 5320del7 | Truncation | 1774 | AT2SF | American | Compd Htz |
| 5178del142[3] | Truncation | 1727 | AT50RM | Italian | Compd Htz |
| 4612del165[3] | Del, 55 aa | 1538 | ATL105 | Japanese | Hmz |
| 44437del175[3] | Truncation | 1480 | AT29RM | Italian | Hmz |

TABLE 3-continued

Mutations in the ATM gene in patients with classical A-T.

| mRNA sequence change[1] | Predicted protein alteration | Codon[8] | Patient | Ethnic/ geographical origin | Genotype[11] |
|---|---|---|---|---|---|
| 4110del127[3] | Truncation | 1371 | AT2TAN[9] | Turkish | Hmz |
| 3403del174[3] | Del, 58 aa | 1135 | F-2095 | Turkish | Compd Htz |
| 2839del83[3] | Truncation | 947 | F-2080[9] | Turkish | Hmz |
|  |  |  | AT10TAN[9] | Turkish | Hmz |
| 2467del372[3,5] | Del, 124 aa | 823 | AT6LA | English/Irish | Hmz |
| 2377del90[3] | Del, 30 aa | 793 | AT21RM[9] | Italian | Hmz |
| 22284delCT | Truncation | 762 | F-169[9] | Palestinian Arab | Hmz |
| 2125del125[3] | Truncation | 709 | F-2078[9] | Turkish | Hmz |
| 2113delT | Truncation | 705 | AT5RM | Italian | Compd Htz |
| 1563delAG[5] | Truncation | 522 | AT8LA[9] | Swiss/German | Hmz |
| 1339C->T | Arg->ter; truncation | 447 | F-2005[9] | Druze | Hmz |
| 1240C->T | Gln->ter; truncation | 414 | AT26RM | Italian | Hmz |
| 755delGT | Truncation | 252 | AT24RM | Italian | Hmz |
| 497del7514[7] | Truncation | 166 | F-596[9] | Palestinian-Arab | Hmz |
| −30del1215 | Incorrect initiation | 5' UTR | F-303 | Bedouine | Hmz |
| In-frame genomic deletions and insertions: |  |  |  |  |  |
| 8578del3 | Del, 1 aa | 2860 | AT3NG | Dutch | Compd Htz |
| 7636del9 | Del, 3 aa | 2547 | AT2BR | Celtic/Irish | Hmz |
|  |  |  | AT1ABR | Australian (Irish) | Hmz |
|  |  |  | AT1SF | American | Compd Htz |
| 7278del6[5] | Del, 2 aa | 2427 | AT5BI | Indian/English | Compd Htz |
|  |  |  | GM5823 | English | Compd Htz |
| 5319ins9 | Ins, 3 aa | 1774 | 251075-008T | Finnish | Compd Htz |
| Other base substitutions: |  |  |  |  |  |
| 9170G->C | ter->Ser Extension of protein by 29 amino acids | ter | F-2089[9] | Turkish | Hmz |
| 8711A->G | Glu2904Gly | 2904 | AT41RM | Italian | Hmz |
| 2T->C | Met->Thr Initiation codon abolished | 1 | AT8BI | British | Compd Htz |

[1]Presented according to the nomenclature proposed by Beaudet & Tsui (1993). Nucleotide numbers refer to their positions in the sequence of the ATM transcript (accession number U33841). The first nucleotide of the open reading frame was designated +1.
[2]Three adjacent exons skipped.
[3]One exon skipped.
[4]This allele produces two transcripts, with one or two ajacent exons skipped.
[5]The same mutation was found in two affected siblings.
[6]Two exons skipped.
[7]This transcript is produced by an allele containing a large genomic deletion spanning approximately 85 Kb within the ATM gene in Family ISAT 9 (Savitsky, et al., 1995a).
[8]For deletions, the number of the first codon on the amino terminus side is indicated. Codon numbers are according to the ATM protein sequence published by Savitsky et al. (1995b). In each section of the table, the mutations are ordered according to the codon numbers in this column, beginning with the one closest to the carboxyl terminus.
[9]Consanguineous family.
[10]All patients are from the same region.
[11]Genotypic combinations in which the mutation was found. Hmz: homozygote; Compd Htz: compound heterozygote. Each patient represents one family.

TABLE 4

Comparison of the ATM protein to related proteins in different species

| Protein | Size (aa) | Species | % identity/similarity | |
|---|---|---|---|---|
|  |  |  | Carboxy terminus* | Rest of protein** |
| TEL1 | 2789 | S. cerevisiae | 45/67 | 19/44 |
| MEC1 | 2368 | S. cerevisiae | 37/63 | 20/46 |
| rad3 | 2386 | S. pombe | 38/59 | 21/46 |
| MEI-41 | 2356 | D. melanogaster | 37/59 | 22/47 |
| TOR1 | 2470 | S. cerevisiae | 33/58 | 19/45 |
| TOR2 | 2473 | S. cerevisiae | 35/60 | 20/45 |
| mTOR | 2549 | R. norvegicus | 32/59 | 18/44 |
| DNA-PK$_{cs}$ | 4096 | H. sapiens | 28/51 | 18/43 |

*350 aa of the carboxy terminus, containing the PI-3 kinase-like domain.
**The entire protein excluding the carboxy terminal 350 aa. An average value is given, since the values obtained for different parts of the proteins vary only by 1–3%.

TABLE 5

GENOMIC ORGANIZATION
Each exon and its flanking intron sequences are listed
separately with the exon underlined. Exons are separated by a
row of ****. Example primers are in bold.

Exon 3 (SEQ ID NO:11)

```
  1  AGGCATACAT CACAATTTGG AATTATGCAT TGGTTTATCA ATTTACTTGT
 51  TTATTGTCAC CCTGCTGCCC AGATATGACT TCATGAGGGT AGGATTTGTA
101  TCTGTTTAGT TCATTATTTG TCTAGCTATA AGTAGTAAAT ATTGTTTGCA
151   ACTATCAGTG AATGAGCATC TTCTGTTTAT GTAGATAATA  CTGAACTG
```

****************************************************************

Exons 4-5 (SEQ ID NO:12)

```
  1  TTACAGCATT ACTTGTATAG ATTTTAAGGA GATCTCATTT TAAATACGGA
 51  AATGTTAAGA AAAATTATTG TGCCTTTGAC CAGAATGTGC CTCTAATTGT
101  ACAGATAAAT CTAACTATAA ATGCTGCAGT ATAAAATAAT TACATACACA
151  TTTTTTCACA CCTCTTTCTC TCTATATATG CATATATACA TACACATATA
201  TATACCTATA TGTATTTTTT TTACAGACAG TGATGTGTGT TCTGAAATTG
251  TGAACCATGA GTCTAGTACT TAATGATCTG CTTATCTGCT GCCGTCAACT
301  AGAACATGAT AGAGCTACAG AACGAAAGGT AGTAAATTAC TTAAATTCAA
351  TTTTTCCTTG AAATGTGTGA TTAGTAACCC ATTATTATTT CCTTTTTATT
401  TTCAGAAAGA AGTTGAGAAA TTTAAGCGCC TGATTCGAGA TCCTGAAACA
451  ATTAAACATC TAGATCGGCA TTCAGATTCC AAACAAGGAA AATATTTGAA
501  TTGGGATGCT GTTTTTAGGT ATTCTATTCA AATTTATTTT ACTGTCTTTA
551  TTTTTCTCTT TCATATTTAT TTCTGTTGTG ATATTACTTT TGTGTGTAAG
601  TCTTAACATT TATCTTTGAT TCCTATATAT CATTATGCCT TGCATATGAT
651  TTTGGCATTT AATATTTATC CAAACATAA TTTTTAAAGG TTGTTCATAT
701  AGAAACTTAA AAATTATAAA TTATTTCTTC AATAAAATGT TTTAGACATA
```

****************************************************************

Exon 6 (SEQ ID NO:13)

```
351  GCAGTAAAGC AATAGAAAGT CATAGAAGAT TAAGAGCTTT GCAGACCAGA
401  TATTAAATTG GTCTTGTAGG AGTTAGGCCT TGAAAGAGAG ATTTAATTGT
451  TTTATTTGTT TTTTTCAGCT GATGTAGTAA TCTAAGCAAG GTGGTTTAAA
501  AGTTGCTCTT TGTGATGGCA TGAACAGCTT TTGAAATTAT TATAATTTAA
551  GTATTCAACG AGTTTCTGAA ATTGCATTTT GTTTTCTTGA AGATTTTTAC
601  AGAAATATAT TCAGAAAGAA ACAGAATGTC TGAGAATAGC AAAACCAAAT
651  GTATCAGCCT CAACACAAGC CTCCAGGCAG AAAAAGATGC AGGAAATCAG
701  TAGTTTGGTC AAATACTTCA TCAAATGTGC AAACAGAA
```

****************************************************************

Exon 7 (SEQ ID NO:14)

```
  1  GAGCACCTAG GCTAAAATGT CAAGAACTCT TAAATTATAT CATGGATACA
 51  GTGAAAGATT CATCTAATGG TGCTATTTAC GGAGCTGATT GTAGCAACAT
101  ACTACTCAAA GACATTCTTT CTGTGAGAAA ATACTGGTGT GAAATATCTC
151  AGCAACAGTG GTTAGGTATG TTTTGAAGGT TGTTGTTTGT GAATTTTTCC
201  TCATGAAATG AAACTTCACC AAAGAAAGCA CTCTGTCTGT ATCTGTCTAT
251  ATCCCCCAAG TGACCTGACA GGTTTAACAG TACTTTAGTA AAATTATATG
301   GTTATCGAAC TGACCCTTAA TTTTTATTTA TTATGTAGCT TTTGAATAA
```

****************************************************************

Exon 8 (SEQ ID NO:15)

```
  1  AATTGTTCTC TGTGTACTTC AGGCTCTATC TGAAACCTTC ACAAGATGTT
 51  CATAGAGTTT TAGTGGCTAG AATAATTCAT GCTGTTACCA AAGGATGCTG
101  TTCTCAGACT GACGGATTAA ATTCCAAATT TTTGGACTTT TTTTCCAAGG
151  CTATTCAGTG TGCGAGGTAA TCTAATCTCT TTTTCTTTGT TTGTATTGA
201  AATACTTTTG ATCTTGCAAG ACCATGTTTT AGACTCAGTA ACTAAAAATT
251  CTACCTTAAA ATAAAACATT GATCCATCAT AACAGAACTA GTGGATTCCT
301  AAAGAGACAA CCAAGTCCAA CACTTTCTGA ATATCCAATA TGCAGAACAC
351   TACGTGAAGT TTTCAAGGGG GAGATGTGTC TTGCTGAT
```

****************************************************************

Exon 9 (SEQ ID NO:16)

```
  1  ACAGAGTGGT CTCTTACACC AAATAAGAAC TAATTTTTTG TCAGTGTGAA
 51  GTAATGCTGT GATTTTTTTT TTAATGAATA GTTTTGAAAT TAAGACTACT
101  GTTTGAAAAT TAGGGTTTTG TTTTTTTTTC TTTCAGCATA CCACTTCATA
151  ACTGTTCAGT TTGTACAGTT TGTTCCCCCT GTTATACCCA GTTGAGCTTG
201  TTTGTTTCTT CACAGACAAG AAAAGAGCTC TTCAGGTCTA AATCATATCT
```

TABLE 5-continued

GENOMIC ORGANIZATION
Each exon and its flanking intron sequences are listed
separately with the exon underlined. Exons are separated by a
row of ****. Example primers are in bold.

```
251  TAGCAGCTCT TACTATCTTC CTCAAGACTT TGGCTGTCAA CTTTCGAATT
301  CGAGTGTGTG AATTAGGAGA TGAAATTCTT CCCACTTTGC TTTATATTTG
351  GACTCAACAT AGGCTTAATG ATTCTTTAAA AGAAGTCATT ATTGAATTAT
401  TTCAACTGCA AATTTATATC CATCATCCGA AAGGAGCCAA AACCCAAGAA
451  AAAGGTATAA AGGAAATGTT TACTGTTTTG AATTTGCTTC TTCATTCAAA
501  CATAGAAGTC TAAGTATAAA ATTAGTGTTC TTTAGGAGGA TATGACTTTC
551  CTCTGGATTT CTCTGGTTGA TAATGTTACT TAGCCATGAG AATGTTTTC
601  ATAGAGTTTT T
```

****************************************************************

Exon 10 (SEQ ID NO:17)

```
  1  GTGCTTATGA ATCAACAAAA TGGAGAAGTA TTTTATACAA CTTATATGAT
 51  CTGCTAGTGA ATGAGATAAG TCATATAGGA AGTAGAGGAA AGTATTCTTC
101  AGGATTTCGT AATATTGCCG TCAAAGAAAA TTTGATTGAA TTGATGGCAG
151  ATATCTGTCA CCAGGTACAG TAAGTAGGTC ATGTCACATT TAGAAATTTC
201  CTGTTAATTT TTTTTTTAAA CTGGGCATTT GGGCTTTTAA AACCTGTGTT
251  CTCACAAAAA GCCTATAAAA TGACTCTGTA CATGCAACTA TTCCTTTCAA
301  ACTATCAGAA ATATTTGGAA TTACCCTTTT AACTTAAAAG TTAATGCTTT
351  TGCAGATATT TGAAAACTAA CAATGAACTT TTTCATTCTT AAATGATTGT
401  CTCTAGGAAA TAAGGTGACC CTAACCCTAA TGATTCGATT CGACTCGA
```

****************************************************************

Exon 11 (SEQ ID NO:18)

```
  1  GGTTGTGGTT ATACGAGATC GTGCTGTTCC ACTCCAACCT GGGCAACAAC
 51  AGCGAAATCT GGCTCAAAAA AAAAAAAAAA GAAAAAAGTG GATTTATTTT
101  TATTTTACAG GTTTTTAATG AAGATACCAG ATCCTTGGAG ATTTCTCAAT
151  CTTACACTAC TACACAAAGA GAATCTAGTG ATTACAGTGT CCCTTGCAAA
201  AGGAAGAAAA TAGAACTAGG CTGGGAAGTA ATAAAAGATC ACCTTCAGAA
251  GTCACAGAAT GATTTTGATC TTGTGCCTTG GTAAAGTGTT ACCATTTTCT
301  CATTCAGTGT CATTTTAATC TCTTGTATGT TATTTTTCAG AAAACTTTCA
351  GTGGAATCCT TTCATCTCAA CCAGAACTAA GTCATTTGTC TACCCCCAAA
401  CCTATTACTA GCAAAGGGAT ATGTGATTGC CATGACAAAT GAGATCAATC
451  ATTAATGGCT CATTTGCTTG GGCCAAGTGC AGGGCCACCT ATTTTAATCA
```

****************************************************************

Exon 12 (SEQ ID NO:19)

```
  1  AACTATTAAC AGCCAGTTTA TTTTTAGAGT ACTATGGAAA TGATGGTGAT
 51  TTCTAATTAG GATATTGTAA GAGTACCATG TCTATATATT TCCTTTTAGT
101  TTGTTAATGT GATGGAATAG TTTTCAAATA TCCTTTTTTT TTTTTTTTA
151  GGCTACAGAT TGCAACCCAA TTAATATCAA AGTATCCTGC AAGTTTACCT
201  AACTGTGAGC TGTCTCCATT ACTGATGATA CTATCTCAGC TTCTACCCCA
251  ACAGCGACAT GGGGAACGTA CACCATATGT GTTACGATGC CTTACGGAAG
301  TTGCATTGTG TCAAGACAAG AGGTCAAACC TAGAAAGCTC ACAAAAGTCA
351  GATTTATTAA AACTCTGGAA TAAAATTTGG TGTATTACCT TTCGTGGTAT
401  AAGTTCTGAG CAAATACAAG CTGAAAACTT TGGCTTACTT GGAGCCATAA
451  TTCAGGGTAG TTTAGTTGAG GTTGACAGAG AATTCTGAGA GTTATTTACT
501  GGGTCAGCCT GCAGACCTTC ATGGTAAGTT CAGCATGCAT TATGTCTGAC
551  TTACAGATAA ACACACACAG ACACACACAC ACTCACATAT CCCTGATCAT
601  TTCCATAGTT TGTTACTTCA GTTAAAGATG TCAAATTCTA TTTCAGATGC
651  TTTTCTTGTT TGGCCGAGAA GACTTAATAA ATGCATAAGT GAATTTAGTT
701  TCAAATGTTG ACAAATTATT AAAGACTAAT GTTAAGGAAT TTCTTTTT
```

****************************************************************

Exon 13 (SEQ ID NO:20)

```
  1  AGAATTATGA AGAGTTTAAA TTTCTTTTAT GTGCAATTTA TCATTATTTA
 51  TTAAATAGCC ATGTTTAAAT TGTAGTACTA TGCACTGTTA ATAAACGAGC
101  TATTTTTTAA TCAAGAATCT TCCCAAATGT AATCAGACTT TTAACAGTTT
151  TTATGTTCAT TTAGTCACCT TAACTAAATG TATGTGCCAG GCACTGTCCT
201  GATAGATAAA GTCTTTGCCC CTCCAATAGC TTGCTTTTCA CAATTGTCCT
251  TTGTTTTGTT ATAGTCCTGC AGTATGCTGT TTGACTTTGG CACTGACCAC
301  CAGTATAGTT CCAGGAACGG TAAAAATGGG AATAGAGCAA AATATGTGTG
351  AAFTAAAATAG AAGCTTTTCT TTAAAGGAAT CAATAATGAA ATGGCTCTTA
401  TTCTATCAGT TAGAGGGTGA CTTAGAAAAT AGCACAGAAG TGCCTCCAAT
451  TCTTCACAGG TAATTTAAGT TCATTAGCAT GCTGCTGTTT TTTTTGTTTG
501  TTTTATCAGG CTCTCTCCAC TTATTTGATG CCAGATGGCT TTATTTTATA
551  ATAATAATGC AGAATTTCCC AGATCTAACC TTAATTATTA AATATTATGT
```

TABLE 5-continued

GENOMIC ORGANIZATION
Each exon and its flanking intron sequences are listed
separately with the exon underlined. Exons are separated by a
row of ****. Example primers are in bold.

```
    601  TTGTTTTTAC AGtTATCTGT GTCTTTATGC CTGATTGCTT CTGAAATAAA
    651   GGGTTGTCTC ACTGTGAGAA TATGGGGGAT GTGCATGAAA AATGCACAT
```

****************************************************************

Exon 14 (SEQ ID NO:21)

```
      1  TGGATCCAAT TAAAGTACTT TTGCTTTAAT TTTACAACCT TTTATTTATT
     51  TCAGAAATAA TGTTAAACAT GCTGTTTCTA AACAGTATTG GAAATGATAA
    101  TAACAATGGT TGTCCTCCTT AAATTGTCCT TTTAGATATT AAGAAATTTA
    151  GTATAGATGA AAGCAATTTT AATCTAGGAT CCAAATTTTA GAAGTCAAGA
    201  TTTATAGCTA AACATGGATG TTAAAGTTTA AAGTATTCTT TACATGGCTT
    251  TTGGTCTTCT AAGTGAAGCT TTTTGTTTTT CTTTGTAGTA ATTTTCCTCA
    301  TCTTGTACTG GAGAAAATTC TTGTGAGTCT CACTATGAAA AACTGTAAAG
    351  CTGCAATGAA TTTTTTCCAA AGCGTGCCAG AATGGTATGT TATCTAATAA
    401  TGCTCTTTAT CATTTTAAGC TATAGCTTTA ATTACAAAGA TGATAATTTT
    451  CGCTGGGTAG tAGCTGCATC TTAATAANGG TCACCTAACT TGGTCCAAAA
    501   AAATTGCAAC TGTTAGCCAG GGAAGAGGTT GTTTTAATTC AGTGATTGT
```

****************************************************************

Exon 15 (SEQ ID NO:22)

```
      1  TTTCTACTGA ATAATGACAT TTGATATAAG TAGGTCTCAA AGTCCGAAGA
     51  AGAGAAGGCA TTTAAAAGAA TAATCTATTA ATTATATGAA GTAGTCTTTG
    101  AATGATGTAG ATACTAGGTT AATGTTTTCC TTTGTAATAT ATTGCTAATA
    151  CATATAAGGC AAAGCATTAG GTACTTGGTT TATATATTAA AGATCTTACT
    201  TTCTTGAAGT GAACACCACC AAAAAGATAA AGAAGAACTT TCATTCTCAG
    251  AAGTAGAAGA ACTATTTCTT CAGACAACTT TTGACAAGAT GGACTTTTTA
    301  ACCATTGTGA GAGAATGTGG TATAGAAAAG CACCAGTCCA GTATTGGCTT
    351  CTCTGTCCAC CAGAATCTCA AGGAATCACT GGATCGCTGT CTTCTGGGAT
    401  TATCAGAACA GCTTCTGAAT AATTACTCAT CTGAGGTGAG ATTTTTTAAA
    451  AAAAGAACTA AGCTTATATA TGATTCAACT TTGGTAAACT GTTAGGAAGG
    501  AGAAATAGGG GCAGGAAAAA CAGCAAGGAT GGTGGGAGGC TTCATTTTAA
    551  AAGCAAAGTG GCAGTAAAGG GCTCTAAATT GGACAACTTA GCATAATTAA
    601   AGGAAAACTC AAGAATAATA ATTTGAGTAC TTCCTTT
```

****************************************************************

Exon 16 (SEQ ID NO:23)

```
      1  CCATCAGGAG ATACTTAGGC TATTTTTCTT GAGAATCCTG GTTATAATTC
     51  TACAGTGATC TCCTAGTTGT TTTTAGAGCT ATCCAGGATA TGCCACCTTT
    101  AACTCAGTTA ACTGAACTTT TGTTTTTTAA TATGTATGTA GAATTTGTTC
    151  TTACAAAAGA TAGAGTATAC TAAATTATTT ATGAAATATA TATATTTTTA
    201  TTTGTGGTTT ACTTTAAGAT TACAAATTCA GAAACTCTTG TCCGGTGTTC
    251  ACGTCTTTTG GTGGGTGTCC TTGGCTGCTA CTGTTACATG GGTGTAATAG
    301  CTGAAGAGGA AGCATATAAG TCAGAATTAT TCCAGAAAGC CAAGGTAGGA
    351  GAATTTATAC TAATAAAGTT TCGGATAAAT TTGAATGAAA TGTATTCCTG
    401  TGAAAATTAT TACATTTGTT TGGAAGACAT TAAATTGTAT GCAGGTTAAC
    451  CCTTTCTCTT TTATTTATGT AATGTGAGAA GAAATTATAC TATGTATTTT
    501  TTAAATTGTT TTAATTGTTT AATTTTTAAT TATTATTATA CTTTAAGTTC
    551   TGGGGTACAT GATGCAGA
```

****************************************************************

Exon 17 (SEQ ID NO:24)

```
      1  AAGATTTGCC ATTTTAAAAA ATTGTTAATG AGTTTTGCTT AAACTGTATG
     51  ACCACGTGGA ACTTCTAAAA ACATTTCATT TTTTCTCTTA AGTGCACTTT
    101  ATTTTTTATT TTATAGTATG TCCAAGATCA AAGTACACTG TAAAAAGCAA
    151  TACTAAACTA TAATTTAAC TGGAATTTGC ATTTTTCCTT CTATTCACAA
    201  TAGTCTCTAA TGCAATGTGC AGGAGAAAGT ATCACTCTGT TTAAAAATAA
    251  GACAAATGAG GAATTCAGAA TTGGTTCCTT GAGAAATATG ATGCAGCTAT
    301  GTACACGTTG CTTGAGCAAC TGTACCAAGG TAAGATTTTC TTCTTCTTGT
    351  TTTGTTTTTT GAGATAGGAT CTTTCTCTGT CACCCAGGCT GGAGTGCAGT
    401  GGGATTGTCA CAACTCATTG TAGCCTTGAC CTCCTGGTTT CCAGCAATTC
    451  TCCTGCCTCA GTCTCCCAAG TAATTGGGAC TACAGGCATG TACCACCTAG
    501   CTAAAATTTT CTTTTTACTT GAAAGTGTAG C
```

****************************************************************

Exon 18 (SEQ ID NO:25)

TABLE 5-continued

GENOMIC ORGANIZATION
Each exon and its flanking intron sequences are listed
separately with the exon underlined. Exons are separated by a
row of ****. Example primers are in bold.

```
  1 TGTTGTTAAA GCACAATGAA AGATGTACAG TATAGTTATT ATAACTCTAA
 51 GAAAAGATGT GTTTTTGAAG CAGCATATAT ATTGGCCCTA ATAGTAAACT
101 ATTTATCTAC ATTCCATTCA AGATAGAGAA AACACTGTCT GCCAAGAATA
151 ATTGTTTTTA TTTCTTTGTT GCTTGGTTCT TTGTTTGTCT TAATTGCAGA
201 AGAGTCCAAA TAAGATTGCA TCTGGCTTTT TCCTGCGATT GTTAACATCA
251 AAGCTAATGA ATGACATTGC AGATATTTGT AAAAGTTTAG TAAGTATGCT
301 TCCTGTTTTG CTATCATATT TTGATTCTAA TAGGCATAAT TTTTTTGTTG
351 AAATATCTTT GTAAATAAGG ATGCATCTCA CAACATATAG CTCTTAACAT
401 TTTTACAAAT GTGGAAATTA AGGCCAGGTG CGGTGGCTCA TGCCTGTAAC
451   CCCAGCACTT TGGGAGGCCG AGGTGG
```

****************************************************************

Exon 19 (SEQ ID NO:26)

```
  1 TTACAGGTGC CCACCACCAC ACCCAGCTAA TTTTTGTATT TTAAATAGAG
 51 ACAAGGTTTC ACCATGTTGG CCAGGCTGGT TTCGAACTCC CGACCTCAGG
101 TGATCCACCT GGCTCAGCCT CCCAAATTGC TGAGATTACA GATGTGAGCC
151 ACTGTGCCCA GCCTGATTAG GTAAATTTTG ACTACAGCAT GCTCCTGCAA
201 GAAGCCATCT TGAACATCTT TGTTTCTCTT CCTTGAAGGC ATCCTTCATC
251 AAAAAGCCAT TTGACCGTGG AGAAGTAGAA TCAATGGAAG ATGATACTAA
301 TGGAAATCTA ATGGAGGTGG AGGATCAGTC ATCCATGAAT CTATTTAACG
351 ATTACCCTGA TAGTAGTGTT AGTGATGCAA ACGAACCTGG AGAGAGCCAA
401 AGTACCATAG GTAAATACAT ATTTACTACT TGGGATTTCT TTTACTTCTT
451 TATATTGATT TGGCAGTATA AGAGGCCTCA TTGATATCAA TTTTGTGCTT
501 ATTTCATTTT CTCTTAGTAT AGCCTTTTAG GATTGTTCCT TTCTTATATA
551 CTTTATTTTT TTTTTATTTT TACTGGAATT TATTAGTTTC ATATTTTATC
601 CTCCATAGAA GGAACTTAAG ATAACTATTA AAGA
```

****************************************************************

Exon 20 (SEQ ID NO:27)

```
  1 TTTAAATTAT TTCTTGACAA CAGAATCTTG GATAATTTTT CAAAAAGACT
 51 TTTGAAGCTT TCAGTATATA ATTAATTTCA CTATAATTTT GCTTTTCATA
101 TACTTTTTTT TGTGAAGAGG AGGAAATTTG AGTTAATATG ACTATATATG
151 GCTGTTGTGC CCTTCTCTTA GTGTTAATGA GTGCTTTTTA TTTTTAGGTG
201 CCATTAATCC TTTAGCTGAA GAATATCTGT CAAAGCAAGA TCTACTTTTC
251 TTAGACATGC TCAAGTTCTT GTGTTTGTGT GTAACTACTG CTCAGACCAA
301 TACTGTGTCC TTTAGGGCAG CTGATATTCG GAGGAAATTG TTAATGTTAA
351 TTGATTCTAG CACGCTAGAA CCTACCAAAT CCCTCCACCT GCATATGGTG
401 AGTTACGTTA AATGAAGAAG CTCTTGGATT TTATCTGATG TTGCTGACTA
451 AATGTAATGA GTTGACATGT AAGAATCACA TGGTGTCTTT GAAGAATTGA
501 AATTGCTTTC TTGAGAAATG AACCTGAGAC TAGTTGGAAA ATAACACTTT
551   TAACGTGCTG TGAGCAAATT TAAGTGGATG CTGAAATATT AAA
```

****************************************************************

Exons 21–22 (SEQ ID NO:28)

```
  1 AGGCGCCTGC CACCACCCCT GGCTAATTTT TGTGTTTTTA GTAGAGATGG
 51 AGTTTCACCA TATTGGCCAG GCTGTTCTCA AACTCCTGAC CTTGTGATCT
101 GCCTGCTTCA GCCTGGGAAA GTGCTGGGAT TACAGGTtG AGCCACTGCA
151 CCCGGCCTAT GTTATATAC TTTTTAAAGT AAATGATTTG TGGATAAACC
201 TGATTTTTTT CCCTCCTACC ATCTTAGTAT CTAATGCTTT TAAAGGAGCT
251 TCCTGGAGAA GAGTACCCCT TGCCAATGGA AGATGTTCTT GAACTTCTGA
301 AACCACTATC GTAAGAAATT AAAACCCTTA TGTTATGTTC ACTTTAAAGT
351 TATAAAATAA CTGATGTGTT CTTAAGCTTA ATAAAGTGGA ACTTTTTTTT
401 TTTTTTTACC ACAGCAATGT GTGTTCTTTG TATCGTCGTG ACCAAGATGT
451 TTGTAAAACT ATTTTAAACC ATGTCCTTCA TGTAGTGAAA AACTAGGTC
501 AAAGCAATAT GGACTCTGAG AACACAAGGG ATGCTCAAGG ACAGTTTCTT
551 ACAGTAATTG GAGCATTTTG GTAGGTACAG TCTATTTTGT GGTCCTATTT
601 TTCTTTTGCT ATCTGTGGAT ACGAATGCAA GTTTTGTATC CACATCAGTG
651 ATTTCTTCTG ATCTGCCTAC ATAGCTAATA CATCTGGAAA GAATAGCAGA
701 ATGTTATTTG TGTTTCCCTC AGTCGCTTGA AGAACTACAT TGCTTTTTGT
751   TTAAGGCTTG GCTTTCTAA
```

****************************************************************

Exons 23–24 (SEQ ID NO:29)

```
  1 ATTCCTTTTA CCACTAATTT CCTTTTAGCT TGAATTTTTG GCAAGGTGAG
 51 TATGTTGGCA TATTCCACAT AATGACAAAT AAGTTTAGCA CAGAAAGACA
101 TATTGGAAGT AACTTATAAT AACCTTTCAG TGAGTTTTCT GAGTGCTTTT
```

TABLE 5-continued

GENOMIC ORGANIZATION
Each exon and its flanking intron sequences are listed
separately with the exon underlined. Exons are separated by a
row of ****. Example primers are in bold.

```
151    ATCAGAATGA TTATTTAACT TTGGAAAACT TACTTGATTT CAGGCATCTA
201    ACAAAGGAGA GGAAATATAT ATTCTCTGTA AGAATGGCCC TAGTAAATTG
251    CCTTAAAACT TTGCTTGAGG TGAGTTTTTG CATTTTTTTA GTAAGATCTC
301    CATTGAAAAT TTTAAAGCAG TCTTTGTTTG TTAATGAGTA ATTTTTCTCT
351    ATTTCATATT TAACCACAGT TCTTTTCCCG TAGGCTGATC CTTATTCAAA
401    ATGGGCCATT CTTAATGTAA TGGGAAAAGA CTTTCCTGTA AATGAAGTAT
451    TTACACAATT TCTTGCTGAC AATCATCACC AAGTTCGCAT GTTGGCTGCA
501    GAGTCAATCA ATAGGTAATG GGTCAAATAT TCATGAAGTA TTTGGAATGC
551    TGCAGATGGC AGTAGAATGT CTTACATAGT AACAGCTCAC AGTTGCAATA
601    TTAAAAATAG CTAACACTTG TTGAGTATAT ACGGTGTGCC TGGCATTTAT
651    GTTTATTCTT AATTCTTATA CTTCTGTCAC TTAGATTCTA TTATTTCCTT
701     CAATTTATAA AT
```

****************************************************************

Exon 25 (SEQ ID NO:30)

```
  1    CTAAGCTGCT GGTCTGAACC TCTTTAAATA AACTCAGGTT TTGTTAGTCT
 51    TTAAGAAAGA GCTAGTATGT TATTATGTCT CACAGAGTGA TTTATTTTTG
101    TTCTGGAATA TGCTTTGGAA AGTAGGGTTT GAAATTAGAA AATTATTTCA
151    CTTTTTGTTT GTTTGTTTGC TTGCTTGTTT TAAGATTGTT CCAGGACACG
201    AAGGGAGATT CTTCCAGGTT ACTGAAAGCA CTTCCTTTGA AGCTTCAGCA
251    AACAGCTTTT GAAAATGCAT ACTTGAAAGC TCAGGAAGGA ATGAGAGAAA
301    TGGTAATTTT AAGTAACATG TATTTGCTGT TATCATATGC TTGCTATGAA
351    TATCCCATAA ATTACTTCAC CAAGTTTGGT ATAAGAGAGT TTATAATCCA
401    GTAGTTTACA GTATAAAGCT GCTCTTCCCC AACTGTATGA ATTGATTGAA
451    ACTGCATTCT TTCTGGGTCA CAATGGGTCA AATCATAGCA ATTTCTTTTG
501    GTTTAGCA
```

****************************************************************

Exon 26 (SEQ ID NO:31)

```
  1    AAAATTGGTA TGTAAACAAT TACAATTTAC ATTACAATTT TTTTTTAAAT
 51    TTCTTTTTAA GTCCCATAGT GCTGAGAACC CTGAAACTTT GGATGAAATT
101    TATAATAGAA AATCTGTTTT ACTGACGTTG ATAGCTGTGG TTTTATCCTG
151    TAGCCCTATC TGCGAAAAAC AGGCTTTGTT TGCCCTGTGT AAATCTGTGA
201    AAGAGAATGG ATTAGAACCT CACCTTGTGA AAAAGGTATA TATGGATGAG
251    TATTTTATTA GAAGCTTCCT TAGGTCACTG TGAAATAATT TAAAAAGTTA
301    AAGCTAGATT TTCTGAGTGG CACTTATTTA AGACTAGGAA ACAATTTTAT
351    TTTTTAGGTT GGGAATATTG GAAAGCAGTT ATACAAAAAC TATTCAAATG
401     GTATATTTAT GGTATGCACT GTTTCTTACA TTCCA
```

****************************************************************

Exon 27 (SEQ ID NO:32)

```
  1    TGCTATGtGT CAGATACTGT GCCAGTTGAG TACATTTTCT TAATTATTAT
 51    TCCCATCTCA TAGATGAGGA AATCAAGAAA AGTTGAATGA ATGTTGTTTC
101    TAGGTCCTAC TCTAAATAAT ATTAACAAGC ATTTAAATGA TTTATTTTTT
151    TCATTTTTCT TAACACATTG ACTTTTTGGT TCGTGCAGGT TTTAGAGAAA
201    GTTTCTGAAA CTTTTGGATA TAGACGTTTA GAAGACTTTA TGGCATCTCA
251    TTTAGATTAT CTGGTTTTGG AATGGCTAAA TCTTCAAGAT ACTGAATACA
301    ACTTATCTTC TTTTCCTTTT ATTTTATTAA ACTACACAAA TATTGAGGAT
351    TTCTATAGGT AAGTTTATAC ATGACATATG TGAAATTTGT TTAATTTAAA
401    ATTAGTTAAC AATACTTAGC AAGTCCCCTC ACCAGCAACA CACATACCAT
451    ACCCATACAC ATGTGTGTGT GGGAGCCTAC ATAGTATGAG AAGCAGGACA
501     GCTTCTTTTA ATAAGAATGT ATTGAAGGGA GTCACTGGAC  TTCAGATC
```

****************************************************************

Exon 28 (SEQ ID NO:33)

```
  1    ATTTTTTTAA TGTGACTATT TAGAATTTAC TTAATTTTTC CATTTATAAA
 51    ATTAAAGAAT GTTTAATAAT CTGGATAAAG TATGATACTT TAATGCTGAT
101    GGTATTAAAA CAGTTTTTAA GAACTATTTT ATAAAATTTT ACTTGGAAAA
151    GTTATATATA ACCTGTATTT TAAATTTTTC TATTTTTAGA TCTTGTTATA
201    AGGTTTTGAT TCCACATCTG GTGATTAGAA GTCATTTTGA TGAGGTGAAG
251    TCCATTGCTA ATCAGATTCA AGAGGACTGG AAAAGTCTTC TAACAGACTG
301    CTTTCCAAAG ATTCTTGTAA ATATTCTTCC TTATTTTGCC TATGAGGGTA
351    CCAGAGACAG TGGGATGGCA CAGCAAAGAG AGACTGCTAC CAAGGTCTAT
401    GATATGCTTA AAAGTGAAAA CTTATTGGGA AAACAGGTAT GGCTTCAATT
451    TTTATGTACT TTTCATTCCC TGAATGATAT GAGATATAAC CTTTAAGTTT
501    TAAGGCTATT TATTCGATTT ATTCGTATTT ATATATTGAA ACTTAGCTTG
```

TABLE 5-continued

GENOMIC ORGANIZATION
Each exon and its flanking intron sequences are listed
separately with the exon underlined. Exons are separated by a
row of ****. Example primers are in bold.

```
551 TGGTAATCAT TATCTAGCAT AGCCAACCCA TGAATTTTTT TGGTTATGTC
601 CGTGTTGTCTC CCTCTGATTG GCTTTTAACT  A
```

****************************************************************

Exon 29 (SEQ ID NO:34)

```
  1 GGGGGCCTTG TTTGGCTGAT TTTCATACTT TTTCCTCTCA GTCTACAGGT
 51 TGGCTGCATA GAAGAAAAAG GTAGAGTTAT TTATAATCTT GTAAATCTTG
101 GACTTTGAGT CATCTATTTT CTTTTACAGT CATCGAATAC TTTTGGAAAT
151 AAGGTAATAT ATGCCTTTTG AGCTGTCTTG ACGTTCACAG ATATAAAATA
201 TTAAATATAT TTTAATTTTG TGCCCTTGCA GATTGATCAC TTATTCATTA
251 GTAATTTACC AGAGATTGTG GTGGAGTTAT TGATGACGTT ACATGAGCCA
301 GCAAATTCTA GTGCCAGTCA GAGCACTGAC CTCTGTGACT TTTCAGGGTA
351 TGTACATTTT AAACTTAGAG AACTAGCTCT AACTTCACAA GTTTTTAAAG
401 AAGTTTATTG GTTGACACCT TCAATGTCTA TTTCAATTTA TAGACATCAC
451  TCTTTTTAAA AAATTTTCTT CAAAAATAGC CACCTTTGAA TTGAGGTAA
```

****************************************************************

Exons 30-31 (SEQ ID NO:35)

```
  1 TAATCTGATT TATATATCTG GACTGTGATA TGTCATTTGT GATTTTATTG
 51 AAAGTATAGT TTTTCAGTAG AAAAATGGTT TTTGAATTTG GGGGTTATTA
101 AAATCTAAAT TTTCATTTTG GAAGTTCACT GGCTATGAAC AAAACTTTTT
151 AAAACGATGA CTGTATTTTT TCCCTTAACT CTGTTAGGGA TTTGGATCCT
201 GCTCCTAATC CACCTCATTT TCCATCGCAT GTGATTAAAG CAACATTTGC
251 CTATATCAGC AATTGTCATA AAACCAAGTT AAAAAGCATT TTAGAAATTC
301 TTTCCAAAAG CCCTGTAAGT ATACATGATG AGTTTAATAA TAGAACATTC
351 CTTCTTTTTT AGCTAAAAAA ACTTTGTAAA TACATCTTAA AGAGGAAAAG
401 TAAACAAATG AAAAATTTAT CTCATAATTA AAAAGGAAAA CATTCATTTA
451 CAAGTTTAAA TGGTATTTTA CTTGTCAGCA TTAATTGAAA TATGTTACAT
501 ATGAGAACGA AATCTTGTGA CACTTTAGTG ATATATTAGC TCAGGGAATA
551 TATCTACTTT TTCATAGGAA TATACTATTT AATTGTAGTT TACTTTCTGA
601 AAATTAAATA AATTGGCAAT AGTTTAAGAT AGTAATTTTC TTAATGTAAC
651 ATTTTGTACT TGATATCAAA CCCAAATCTA AATTCTGTTA TTTAGTTATT
701 TTAAATATAA AATGTGTAGG TATTCAAATA TTTGAAGAAA AATATAAAG
751 TGTATTTATT GTAGCCGAGT ATCTAATTAA ACAAGTTTTT ACTAAATCTG
801 TTTATTTTCT TAGGATTCCT ATCAGAAAAT TCTTCTTGCC ATATGTGAGC
851 AAGCAGCTGA AACAAATAAT GTTTATAAGA AGCACAGAAT TCTTAAAATA
901 TATCACCTGT TTGTTAGTTT ATTACTGAAA GATATAAAAA GTGGCTTAGG
951 AGGAGCTTGG GCCTTTGTTC TTCGAGACGT TATTTATACT TTGATTCACT
1001 ATATCAACCA AAGGTAAATA ACATATTTAG ACCAATATAT AAGCAGTCTT
1051 TCTATCCTGT TCTTCCTGTT TTTTTGCTTT GTTTTGTTTT GTTTTGAGAC
1101 AAAGACTCAC TCTGTCCGCC CAGGCTGGGT GCAGTCACGG CTCACTGCAT
1151 CCTCAACCTC CTGGGTTCAG ATTATCCTTC CTCCTCACCC TGCCGGGTAG
1201  CTGGGGCTAC AGGAG
```

****************************************************************

Exons 32-33 (SEQ ID NO:36)

```
  1 ATGTTTCTAT TAAAGGATGG AAGCTTAGAG CTGCCTATTC TGCATTTTGC
 51 TGATGTGACT TCTCTTTTTG GCTTATAAGC CATTAAAATA TTTTNGTCAA
101 GGCATATAAG AATTAGAGAT GCTGAACCAA AGGACTTCTG AATGAATTTA
151 TTTCAGAGTA ATTTTCCAGA ACTTACTGGT TGTTGTTGTT TTTTTTTCTC
201 CCTATATTAG GCCTTCTTGT ATCATGGATG TGTCATTACG TAGCTTCTCC
251 CTTTGTTGTG ACTTATTAAG TCAGGTTTGC CAGACAGCCG TGACTTACTG
301 TAAGGATGCT CTAGAAAACC ATCTTCATGT TATTGTTGGT ACACTTATAC
351 CCCTTGTGTA TGAGCAGGTG GAGGTTCAGA AACAGGTAAT TTTCTGACTC
401 ATCTTCAAAA ATGGTATTTA AAATATATAA AGTATTGTTA GAAGGATTTG
451 AGTGTTTTAT GTTTATTTGG TATAATTGGT GATTTTATTG AGAATATTTT
501 TTGTAAAATG ATTGGAAAAA TATTCTTAAT GAATTAACCT TTGTAATCAA
551 TTACAGAGCA CTTGGTACTT TTGATAGTTT TATCTACTGT GCTGAAGTGG
601 AGAGGTAGTC AAAACTAGGG ATAGCAGTTC GCAACGTTAT GGTGGTATTT
651 GAGTTACTAC TTATATAAAC TGTTTCATTA ATATTGGCAT TTTTTTTAAC
701 CTCAGTACCC ATCTTGTAGT AGTACCTTAC ATAGTTATTG AATTATTTGA
751 AAACACAGAA ACTAAAAGCT GGGTATCTTA GACGTAATAA GAACATTTAA
801 TCTGATCTAG GTTAATAGAT TTTATCATTT ATTACAGTAA GTTTTGTTGG
851 CTTACTTTAA AATTATTTCT CTCCTTATAA TTTTTTCTTT TTAAATTATA
901 TTTAGGTATT GGACTTGTTG AAATACTTAG TGATAGATAA CAAGGATAAT
951 GAAAACCTCT ATATCACGAT TAAGCTTTTA GATCCTTTTC CTGACCATGT
1001 TGTTTTTAAG GATTTGCGTA TTACTCAGCA AAAAATCAAA TACAGTAGAG
1051 GACCCTTTTC ACTCTTGGAG GTAATAAAAA TTTCATCATC TACTATTTTT
```

TABLE 5-continued

GENOMIC ORGANIZATION
Each exon and its flanking intron sequences are listed
separately with the exon underlined. Exons are separated by a
row of ****. Example primers are in bold.

```
1101   TATTAGAGAA CATAGTAGTA CTTTTCAAAA ATCTGTAATG CTCTAGCAGT
1151   AAAAAATGGA ATCTTTTCTT TAATTGTGAT TAAAAATATA TACGTAGGCC
1201   AGGCACATTG GCTCATGCCT ATAATCTCAG CACTTT
```

****************************************************************

Exon 34 (SEQ ID NO:37)

```
  1    GACTCTGTCT AAAAAAGAGT ATTAAAACAT TGTAGGGTTT GCAGTGGAAG
 51    AAATCATTTA TTTCTTCCTT GATTAGTAGT AATAGAGACA TGAGTCAGTG
101    TCTATAAATG GCACTTAACT AATTTTTTTC TTTTATTAAG TTTTATTTCA
151    CAGGCTTAAC CAATACGTGT TAAAAGCAAG TTACATTTTC TCTTTTAGGA
201    AATTAACCAT TTTCTCTCAG TAAGTGTTTA TGATGCACTT CCATTGACAA
251    GACTTGAAGG ACTAAAGGAT CTTCGAAGAC AACTGGAACT ACATAAAGAT
301    CAGATGGTGG ACATTATGAG AGCTTCTCAG GGTGCTAATT TTAAATGACA
351    TGGGCTATTT CTACCTGTTT CTTTTTGGAA AGAATATTTT GCAAAGTCTT
401    GCTCTTGGTT TCATTGTCAC AGACTTAGTT CAGACTCTCA TCATTTAGTT
451    CAGACCCTCA TTTCTCATCT AACTGTAAAA CTGGTCCTAA CTGGTCTTCT
501    CACCCTGAAC TCTTCCTGTT TTATTCATCC TCTGCCAGAT G
```

****************************************************************

Exon 36 (SEQ ID NO:38)

```
  1    ACCTCTGTCT CCCAAAGTGC TGGGATTACA GTCGTGAGCC ACCGCACTCG
 51    GCCTTAAGGT TAATTCTTGA AGTACAGAAA AACAGCATTA TAGTTTGGAA
101    ATTAGAAAAT ATCAGTTTTA TGTATGATCT CTTACCTATG ACTCTACTGA
151    AATAGAATTT CTATATGTAG AGGCTGTTGG AAGCTGCTTG GGAGAAGTGG
201    GTCCTATAGA TTTCTCTACC ATAGCTATAC AACATAGTAA AGATGCATCT
251    TATACCAAGG CCCTTAAGTT ATTTGAAGAT AAAGAACTTC AGTGGACCTT
301    CATAATGCTG ACCTACCTGA ATAACACACT GGTAGAAGAT TGGTGAGTAT
351    TTATTGATAC CTTATATGTA ATCTCAATAT GACATTCATG GAGAATGATA
401    CTTCACACAA ATAGATATTC TCAGTAACTA AAGCTTTGTC CTTTTTTAAA
451    TCTCAGTGTC TTTATGAAAA TTCTTATATT TTTATTAATT CACATAATTA
501    TTTACCCTAC TATGTGCCAG ACACTTGATA TAATGGT
```

****************************************************************

Exon 37 (SEQ ID NO:39)

```
  1    GTTGCAGTGA TTAGTAATTC AAGTTTACTG AATGACTAGT GAAAGTCCTT
 51    TGATACTTTT ATTTGATATT GGAGAATTTT GTAAATGTAA AGTTTCCTAA
101    AACCAATTTT AAATTTTAGT TTTGAAATTT TTTCAGTGGA GGTTAACATT
151    CATCAAGATT AATAACTGGT GTACTTGATA GGCATTTGAA TTGTTTTTTT
201    CAGTGTCAAA GTTCGATCAG CAGCTGTTAC CTGTTTGAAA AACATTTTAG
251    CCACAAAGAC TGGACATAGT TTCTGGGAGA TTTATAAGAT GACAACAGAT
301    CCAATGCTGG CCTATCTACA GCCTTTTAGA ACATCAAGAA AAAAGGTCTC
351    TTAAGTAATA AATGTTTATT GAATACCCAG CATATCTAAA ACAGTTCTGT
401    TTGCTGTGGG TCATGACTGT TAAATTGCTT GAAATAGTAT TGTACTAACT
451    ATTAACCTTT CCTATAAGTA ATTTAAGCCA TATTTCATAA ATCCAGGGAA
501    TGTGTTATTT TTAATTTATT ATGGCAGTGT G
```

****************************************************************

Exon 38 (SEQ ID NO:40)

```
  1    AAACATAAAT GTTTTCATCT TAAAAGGTAA ACATTGCCTC CAGATTTAGT
 51    TTTAACTGTA TTTAGCTTTA TTCAGAAAGA TTTGTTATAC TCATTTTGTG
101    TAGGAAAGGT ACAATGATTT CCACTTCTCT TATTTACATT TTCTAATCCC
151    TTTCTTTCTA GTTTTTAGAA GTACCCAGAT TTGACAAAGA AAACCCTTTT
201    GAAGGCCTGG ATGATATAAA TCTGTGGATT CCTCTAAGTG AAAATCATGA
251    CATTTGGATA AAGACACTGA CTTGTGCTTT TTTGGACAGT GGAGGCACAA
301    AATGTGAAAT TCTTCAATTA TTAAAGCCAA TGTGTGAAGT AAGAAGATTA
351    ATTAGTCTGA TATAATTCCT TGTTTATGAC CTGTTTATCT AAAGAGTGCT
401    GTGATACTGC ACATCATCTT CACATAATAT CACCCCCACT CAAACTGTTG
451    TAAATTTATT AAAGTGAGCA TCCGTATTTA GTCATAACTT TATGCATTAG
501    GTTTCAGCTT CGGGATAGCA ACATACT
```

****************************************************************

Exon 39 (SEQ ID NO:41)

```
  1    CCTAGTGTGG TTTTTTAAAC ACCACCTAAT ACATGTTTTT TGTTTGTTTT
 51    TTTAGCAGTA TGTTGAGTTT ATGGCAGATT AATCTATCAT CTTTTAGAAA
```

TABLE 5-continued

GENOMIC ORGANIZATION
Each exon and its flanking intron sequences are listed
separately with the exon underlined. Exons are separated by a
row of ****. Example primers are in bold.

```
101  TTTAATATGT CAACGGGGCA TGAAAATTTT AAGTAAAATG TATTAATTTT
151  ACTCATTTTT ACTCAAACTA TTGGGTGGAT TTGTTTGTAT ATTCTAGGTG
201  AAAACTGACT TTTGTCAGAC TGTACTTCCA TACTTGATTC ATGATATTTT
251  ACTCCAAGAT ACAAATGAAT CATGGAGAAA TCTGCTTTCT ACACATGTTC
301  AGGGATTTTT CACCAGCTGT CTTCGACACT TCTCGCAAAC GAGCCGATCC
351  ACAACCCCTG CAAACTTGGA TTCAGGTATT CTATTAAATT TTTAACATTA
401  ATACTGTAAA CTCAGTTCTA GAGAAAGATG GATTTAAGAT GGAATCCCAC
451  TAAAAGCACT TTACAGGATT AAATCTATAA CCTCTAAATT TGTTTCTTCA
501  TCTATGGAAT GGAGATAAAA GTTGCCAACA GTTGCAACAA GTTTTCAATG
551   AAATAATGTG TGTAAG
```

****************************************************************

Exon 40 (SEQ ID NO:42)

```
  1  TAAGTTCTCA CTTTTTTTAA GATAACAGTT TCTTTTAAAA GCAAAAGAAA
 51  TCCTATTAAA TTCCTTCAGA ACCAATTTTG TGTTAGGTAC TGCCCACCAG
101  AACCTTATAG CATAGTGGGA GACAGACACA TAAACAAGAA GGAAGAAGGT
151  GTGTAAGCAA GAATGCCTGG GACTGAGGGG AGATATTTTT GTTTGTCAGA
201  GTCAGAGCAC TTTTTCCGAT GCTCTTTGGA TAAAAAATCA CAAAGAACAA
251  TGCTTGCTGT TGTGGACTAC ATGAGAAGAC AAAAGAGGTA ATGTAATGAG
301  TGTTGCTTCT TACGTTTAGG ATCTAGAGTG TAACTTGTTA ACTATCGGCT
351  GAATTTTAAC ATGATTATTT TAGGTGAAGG TGTTGCAAAG TGTTATATTT
401  AATTTGTGTG ATATTTATAT CTCCTTGCAG tAATCCATAT TCAGGATAGC
451   AGTTTGGTTA AATCAGTGTC AAGAA
```

****************************************************************

Exon 41 (SEQ ID NO:43)

```
  1  TTAATTAAAT AGGACTCTTC AGCCATGTTA TCTTATAATG TTTATAGGTA
 51  TATATTGGGG AAATGTGGTT TTTGGGAATT TGTAATTTTC TGTTAAGCAG
101  TCACTACCAT TGTATTCTAT ATCAACATGC TTTTATTTTG ATATTGAAGT
151  TTAAAAAAGT GAATGACATT ATATCTCATT TTTCTTTAGA CCTTCTTCAG
201  GAACAATTTT TAATGATGCT TTCTGGCTGG ATTTAAATTA TCTAGAAGTT
251  GCCAAGGTAG CTCAGTCTTG TGCTGCTCAC TTTACAGCTT TACTCTATGC
301  AGAAATCTAT GCAGATAAGA AAAGTATGGA TGATCAAGAG AAAAGGTAAT
351  GGAATTTAGA ATTTTTGGTT TTTAAAATTA ATGTTGGCAT TGTCTCAATA
401  AGGGTATATA GTAAAGATTT ATTTTGCCTC CTGTTCCCCA TTTAAAAGAT
451  ATTTTAGATA GAAATTTTGT TTTAAAGTGA AATTATAATA AATTTTTAAA
501   AAGGAATATG TAATTCCTGT TCTGAAAT
```

****************************************************************

Exon 42 (SEQ ID NO:44)

```
  1  CTTTTCCATC CTAGGTATAA ATGGTATTAT GTTTTAAAGT ATAAGTGATT
 51  TATTCTGTTT TGTTTGCCAC CTTCATTAGT TTTTTTCTGT CAAAGTCTAT
101  AGTATATGTA TTCAGGAGCT TCCAAATAGT ATGTTCTCAT TAAAAGAGGT
151  GTTCTTGTGA CAAACAGAAGTCTTGCATTTGAAGAAGGAAGCCAGAGTAC
201  AACTATTTCTAGCTTGAGTGAAAAAAGTAAAGAAGAAACTGGAATAAGTT
251  TACAGGTAAA TATTAGAGGC TCTATTATTT ATGACAGTAT TTATCTCATA
301  CTTTGGGTTA TTTTGTTATA GACACTGTAC AGATGCCATG TGATTTTTAA
351  ACTGAATTTA CTTACTGGAC TAAGCATCAT ATATATAAAA TTATGGTCTG
401   AAGCTTAAGC CTTAGAGTAG ACAGACTTGA GTTCTAATAC  TGAC
```

****************************************************************

Exons 43–44 (SEQ ID NO:45)

```
  1  TTGTCCTGCA CAGTTCAAAC TCGTGTTGTT TGAACTGTAT TTCAGAACTG
 51  TATTTCAGAA TCATTACATT TTATTTCTAT AACATAACAT TTAGAGTTGG
101  GAGTTACATA TTGGTAATGA TACAATTTAA AATTTGCTAA ATTTATAGAC
151  CGATTTTTTT TCCTTCTTCA ATTTTTGTTG TTTCCATGTT TTCAGGATCT
201  TCTCTTAGAA ATCTACAGAA CTATAGGGGA GCCAGATAGT TTGTATGGCT
251  GTGGTGGAGG GAAGATGTTA CAACCCATTA CTAGGTAAAT TGCATTTTTC
301  TAAACAACGG TATAGTAATT CTGTTTATGA AGGAGTTATG TGTGTGTTAA
351  ACCCAAAGCT ATTTTCACAA TCTTTTCTTA TAGACTACGA ACATATGAAC
401  ACGAAGCAAT GTGGGCAAA GCCCTAGTAA CATATGACCT CGAAACAGCA
451  ATCCCCTCAT CAACACGCCA GGCAGGAATC ATTCAGGTAC ATTTTTTCCC
501  AGATTTGGTA AAGCCATCAC TAGTGTAGTG CTGAGGTTAT TTCAGTATGT
551  TGGTGGATAT TTACACAGCC AGATAAACTC TAGAGATAAG ACTAGAACTT
601  ATCTGTTTTT CAGAGGATTA GGCTAAACAT TCAGGGATAC TCCTGAAGCA
651   GAGGGATGCA AAAAAAGAG AAAAAATTCA  GGGAGACA
```

TABLE 5-continued

GENOMIC ORGANIZATION
Each exon and its flanking intron sequences are listed
separately with the exon underlined. Exons are separated by a
row of ****. Example primers are in bold.

****************************************************************

Exon 45 (SEQ ID NO:46)

```
  1  CCTCCTGCCT CAGCCTCCCA AAGTGCTGAG ATTACAGGCA TGAGCCACCA
 51  CACCCAGCTG ATATTTTGGG ATTTTAAATG ATATTGTGAA CTAAAATTTG
101  TCTAAGTTAA TTTGTATCTT TGCTGTTTTT TTCTCTGTT TTCTGTTGAT
151  ATCTTTGATT ACTTAACTTA AAAACAAAAT AACTCCTGTT TAGGCCTTGC
201  AGAATTTGGG ACTCTGCCAT ATTCTTTCCG TCTATTTAAA AGGATTGGAT
251  TATGAAAATA AAGACTGGTG TCCTGAACTA GAAGAACTTC ATTACCAAGC
301  AGCATGGAGG AATATGCAGT GGGACCATTG CACTTCCGTC AGGTAAGAAA
351  TTTGACTTGA TTTTTTTTTT TTTGCCTCTC TCCTCATTCT AAACAACAAC
401   TGTTTTCTC TTCTATGA
```

****************************************************************

Exon 46 (SEQ ID NO:47)

```
  1  TTTTTCTGCT TAAAGAATTT AAATGACTCA TAAAATTTGT ATTTCTTACC
 51  AAAAATTCTA GAAATGCATT TTTTAGAATG GAGAAATGTT AATTTAAAAA
101  TTTTGTCCTT TGGTGAAGCT ATTTATACAT GTATATCTTA GGGTTCTGTT
151  TTTAAGTATA TTTTTTTCTT TGACTTATCT CACAGCAAAG AAGTAGAAGG
201  AACCAGTTAC CATGAATCAT TGTACAATGC TCTACAATCT CTAAGAGACA
251  GAGAATTCTC TACATTTTAT GAAAGTCTCA AATATGCCAG GTATTATGAA
301  AAGACAAAGT TACTGTATTT TAACATTTAA TGTCATGGCT TCTTTTCTGA
351  AAACTTGAGA AACAATTTTA ATGTAAGGAT TTGCATTGAT GAAGAGATAA
401  AGACTTGGTG GCTGTGATCA GATGTTTCCT TGTAATTCTC TGCCCTCCTT
451  CAAAACAAAT TGTTTCTGGG ATTCCAGGTT CATTCTTTAC CCTGACCCTT
501   CAAGAAAGTT TTG
```

****************************************************************

Exon 47 (SEQ ID NO:48)

```
  1  AGTGTAAGTG GACCATGCAT TTAAATTTGT GTTGTTCAAG GGTCAGTTGT
 51  ATTCTGTTTC CACTGCTATT TTGTACTCAC TGCTGCTTGT TAGTATTATT
101  AGATCAGTAG CATAGCCTAT GATGAGAACT CTTTAACAAC AAATTTAAAC
151  ATTTATTTCC CTGCAAACCT CTTCTTTATT TTCAGAGTGT CTTTTCTTTT
201  TTGCTACTAG AGTAAAAGAA GTGGAAGAGA TGTGTAAGCG CAGCCTTGAG
251  TCTGTGTATT CGCTCTATCC CACACTTAGC AGGTTGCAGG CCATTGGAGA
301  GCTGGAAAGC ATTGGGGAGC TTTTCTCAAG GTATGTAATT CGTATGACTT
351  TGTTATCCTA AAGTGCAGCT TTTCTGTTAC CAATAGTGAC TTTAAAAAAT
401  AAAAACTATA GGCCGGGCAC GGTGGCTCAT GCCTGTAATC CTAGCACTTT
451  AGAAGGCTGA AGTGGGTGGA TCACTTGAGG TCAGGAGTTC AAGACCAGCC
501   TGGCCAACAT GGT
```

****************************************************************

Exons 48–49 (SEQ ID NO:49)

```
   1  TGTATTATTA TAATATTATA TCGTAAGTTC CAGGACTTAC ATAGTTTTTT
  51  TTTTTTTTTT TTCATTTCTC TTGCTTACAT GAACTCTATG TCGTGGCATT
 101  CAGATCAGTC ACACATAGAC AACTCTCTGA AGTATATATT AAGTGGCAGA
 151  AACACTCCCA GCTTCTCAAG GACAGTGATT TTAGTTTTCA GGAGCCTATC
 201  ATGGCTCTAC GCACAGTCAT TTTGGAGATC CTGATGGAAA AGGAAATGGA
 251  CAACTCACAA AGAGAATGTA TTAAGGACAT TCTCACCAAA CACCTTGTAG
 301  AACTCTCTAT ACTGGCCAGA ACTTTCAAGA CACTCAGGT AAATACAATT
 351  TAAAACTATG TCATCTTACC TCTTGACTTT CCTTTTATTA TTTAAAAAAC
 401  TGAAAGCCTG AGGGAAAAAG AAATGTCATT AAGAGATAGA GATCTCTATT
 451  AATATATAGT AAAAATAATT GTTTAAGAGT TCCCATTTTG GAATTAGATC
 501  TGACTTTTAA GCCTTGGGCA AGGGTACTTA ATCTTTTCTC AACCTCAATT
 551  TCCTGGTTAT AAAATGAGAA GATACCTAAC TTACTATATT GATAACAATT
 601  CAGTGATTTT ATATACTGTG TGTATGTACA CACAGATACA CATACATACA
 651  TATAGAGAGA GACAGACAGA CAGACAGATA GGCAGACGTG GGGTGGGGAG
 701  ATTGTCAATG CAGACAGAGA GGGTCCTTAA AGATAGTCCC TGACAAGTAG
 751  TTAAAGTCCT CAAATGAATG GTAGTTGCTG CTTTCATTAT TATTATTATT
 801  CAAGGTAGTA GTATCAAGTA GTAAAAGTAT TTATTCCCAT ATGTCATTTT
 851  CATTTCAGCT CCCTGAAAGG GCAATATTTC AAATTAAACA GTACAATTCA
 901  GTTAGCTGTG GAGTCTCTGA GTGGCAGCTG GAAGAAGCAC AAGTATTCTG
 951  GGCAAAAAAG GAGCAGAGTC TTGCCCTGAG TATTCTCAAG CAAATGATCA
1001  AGAAGTTGGA TGCCAGCTGT GCAGCGGTTT GTTTTTTTTA TTGGCTGGAT
1051  TAGTGTTTTA CTGTTATTTA AAAAAACACA AATGTACTTT AAAATATTTT
1101  TAATAACAAT TTTATTGAG CCTTGAAATT AGTAATTTAT TAACAAGATA
```

TABLE 5-continued

GENOMIC ORGANIZATION
Each exon and its flanking intron sequences are listed
separately with the exon underlined. Exons are separated by a
row of ****. Example primers are in bold.

```
   1151   TTGTAAAACT AGTCTTGAAA ATTAATTTGT AAATGAAGTT TAGAAACTTT
   1201   TTCCTATATA TCACAATTCT ATCAGTCCAT CATGTGGTCG ATTCATTTAA
   1251   TATA
```

****************************************************************

Exon 50 (SEQ ID NO:50)

```
      1   TAATAATAAT AAACAGAGGA TGATCATTTC CtACATGGGA TTATTAAAAT
     51   AGTTGTATGG CAAAAGCAGA TGAGGAAAAA CTTTTTTTTT CCCACCCACC
    101   AAGGAAAAAC ATTTTTAACC TGCTTTTTTC CCCCGTACAT GAAGGGCAGT
    151   TGGGTACAGT CATGGTAATG CATTATATTT TAAGATTTTG CCTTTCTTAT
    201   ACAGAACAAT CCCAGCCTAA AACTTACATA CACAGAATGT CTGAGGGTTT
    251   GTGGCAACTG GTTAGCAGAA ACGTGCTTAG AAAATCCTGC GGTCATCATG
    301   CAGACCTATC TAGAAAAGGT AAGATTTTTG GAGCAACCCT TAAGATAGTT
    351   ACTTAGCATG AATATGCTTC ATCTTTTCAT CAAGATCAAT ATATTTCCAA
    401   AGCAAATAAA AGTATGGTTT TATTTTTCTA TATATTATTA CTGTTGTAGC
    451   TCTGTATAGT CTCTAGGGTG GAGTGAAACA TTGTTACAAA ACAAAGCAGC
    501    CAATTTGAAA AGTAAGCCCA AGTATAGTAT  CTCTTCT
```

****************************************************************

Exon 51 (SEQ ID NO:51)

```
      1   TTTAAGAAAA TGTACGAATT TGTGTTGGGC CACATTCAAA GCCGTCCTGG
     51   GCCACATGCG GCCCATGGGC CGTGGGTTGG ACAAGTTTGC AATAGTTCAT
    101   ATAATTTAGC TAGCTTTTAT ATGTATATAA GTTAAATTTT AGTGTATTAC
    151   CTTAATTTGA GTGATTCTTT AGATGTATTT AGTATTTGTA AATATAATTT
    201   AAATTGGTTG TGTTTTCTTG AAGGCAGTAG AAGTTGCTGG AAATTATGAT
    251   GGAGAAAGTA GTGATGAGCT AAGAAATGGA AAAATGAAGG CATTTCTCTC
    301   ATTAGCCCGG TTTTCAGATA CTCAATACCA AAGAATTGAA AACTACATGA
    351   AATCATCGGA ATTTGAAAAC AAGCAAGCTC TCCTGAAAAG AGCCAAAGAG
    401   GAAGTAGGTC TCCTTAGGGA ACATAAAATT CAGACAAACA GGTAACTAGG
    451   TTTCTACAAG TGACAATTTT ATGTTCACCA GTTAACTGAG TGAGTGTTTT
    501   TGCATAGAAA GAGTGACTTG GTCTTTTTAT CTGATATAGT TTTGAGCTCT
    551   AAAGGTCGGC TTAACTATAT ATAGATTATC TTGGTCTTTT GGGTTCTTTT
    601   CGGTTTTTGT TTTTTGTGTT TTTTTTGAG ACAAGGTCTC ACTCTGTCAC
    651    CCAGGCTGGA GTACAgtGGc GTGATCACT
```

****************************************************************

Exon 52 (SEQ ID NO:52)

```
      1   TCCCCTTTGT CCTTTGATGC TTAGGAAGGT GTGTGAATTG CACAGTTAAG
     51   ACAAAAGTAA GTTTATTCCC TTTATAATCC TTAGAAGTTT GCTTTTTTCC
    101   CTGGGATAAA AACCCAACTT TTTTCATTAA ATGTTGTATA TCATGTGTGA
    151   TTTTTGTAGTT CTGTTAAAGT TCATGGCTTT TGTGTTTTAC CTTAATTATT
    201   CTATGCAAGA TACACAGTAA AGGTTCAGCG AGAGCTGGAG TTGGATGAAT
    251   TAGCCCTGCG TGCACTGAAA GAGGATCGTA AACGCTTCTT ATGTAAAGCA
    301   GTTGAAAATT ATATCAACTG CTTATTAAGT GGAGAAGAAC ATGATATGTG
    351   GGTATTCCGG CTTTGTTCCC TCTGGCTTGA AAATTCTGGA GTTTCTGAAG
    401   TCAATGGCAT GATGAAGGCA AGTGTTACTC AGCCCAATAT TCTACCCTGT
    451   GCTTGAAAAA CTTAGACATA AGCCCCTTGA TGTCAGGAAT CGTGTATACC
    501   TCTTTGTATT CCTAGCACTT GGTCCAGTGC TCTACACATA AGTAGCATTT
    551   TGTAGTTTTC TAAACTTTGA TCCATATTTA GGATTATTTA CAAGTTCTAG
    601    TCTTGTTTCT
```

****************************************************************

Exon 53-54 (SEQ ID NO:53)

```
      1   AATCCAGTTT AATTTAGGAC CCAATATTTT GATTTACCAA TGCATTAATC
     51   TAGAGTACCC ATTAGAAAGA CCTTCAGATA AGAAAAGAAA TGAAGGAAAA
    101   CAATATAGTT AGTGAAGTTT TGTTAACCAC TTGTGCTAAT AGAGGAGCAC
    151   TGTCTTAAAA TAACTTACTT GCTTAGATGT GAGAATATTT GAAATACCTT
    201   GTTTCTTAAT TTTGTGTCTT TTTTTTAATG GTAGAGAGAC GGAATGAAGA
    251   TTCCAACATA TAAATTTTTG CCTCTTATGT AGGAATTGGC TGCTAGAATG
    301   GGGACCAAGA TGATGGGAGG CCTAGGATTT CATGAAGTCC TCAATAATGT
    351   AAGTAAACCT GAAAATCAAA CCACAATAAT TATTTTTATT CTATTATTAC
    401   TATATATTAT ATAAAGTATA TATACCATTC CCTCTAAGAA ATGGAAATAC
    451   AAAATTTTGT ATTTTTTGTC TTCTCACATC ACATAAGTTA CTCATTTTCT
    501   CTCTCTAATT CCTCATAGGC CTCTGCCTTT TTCTCACACA TGCAGGCATA
    551   CACGCTCTAC CCACTGCAGT ATCTAGACAG TAATACACAT TTTAATGTTA
    601   AGCAAAATGA AAAATATGGA TTATATTTTT TTGTTTATTT GCATAAATCT
```

TABLE 5-continued

GENOMIC ORGANIZATION
Each exon and its flanking intron sequences are listed
separately with the exon underlined. Exons are separated by a
row of ****. Example primers are in bold.

```
    651  AATAGTTCTT TTCTTACAGC TAATCTCTAG AATTTCAATG GATCACCCCC
    701  ATCACACTTT GTTTATTATA CTGGCCTTAG CAAATGCAAA CAGAGATGAA
    751  TTTCTGACTA AACCAGAGGT AGCCAGAAGA AGCAGAATAA CTAAAAATGT
    801  GCCTAAACAA AGCTCTCAGC TTGATGAGGT ATTGGGATTA ACCATACGTA
    851  CCTTTTAGAA GTGTGATATT CAGTCTTTCC TAGAATATTT CTTTTTAAAA
    901  TCTTGTGTTA TTAAGATGCC ATCTAAAATC GGTTCAAGGC TGGCACGGTG
    951  GCTCACGCCT GTAATCCCAG CACTTTGGGA GGCTGAGG
```

****************************************************************

Exon 55 (SEQ ID NO:54)

```
      1  GAAAGGCACC TAAGTCATTG ACGAGAGTAT GTATCTTTGA TGTATTTCAT
     51  TTATGACTGT TTTGTTTGTA TCTGAGGAAT TATAATCATT CCATAGTCTA
    101  GATTTGTGCA TAAATTCTGT TTTTCTCTTT GTTTTTCTAA CTCTGAGAAG
    151  TTTAAATGTT GGGTAGTTCC TTATGTAATG TTTTTTGTTT TTTATTAATA
    201  GGATCGAACA GAGGCTGCAA ATAGAATAAT ATGTACTATC AGAAGTAGGA
    251  GACCTCAGAT GGTCAGAAGT GTTGAGGCAC TTTGTGATGA TTATATTATA
    301  TTAGCAAACT TAGATGCCAC TCAGTGGAAG ACTCAGAGAA GTATGTTTTT
    351  TTTAAAGAAG AAACGTTACT TTCTTGCTGT GTTACTCTCT GTAGAGATAT
    401  ATTAGTTATA GAGCCTAATA AGTAAATCTG CTTAAAATCA CAAACGTAAT
    451  CCAAAAGCTT AATTTATATC TGATGGCTTC AACATTCCCT GGTTACTTTT
    501   TCACTTAATA TCTCTTAATA GAACTGGTAA  TAGGTGA
```

****************************************************************

Exon 56 (SEQ ID NO:55)

```
      1  CTGTTGAGCT TTGACTCTGA GCTGCATAGT GGCCAAAGCC CAGAGTCTTC
     51  ATTTCTCAAT CAGAGCCTGA ACCACAGATT AGCAACAAGT TGGGGCCAGT
    101  GGTATCTGCT GACTATTCCT GCTTGACCTT CAATGCTGTT CCTCAGTTTG
    151  TCACTAAAAT CTCTTCATTT TTAAATACAG AAGGCATAAA TATTCCAGCA
    201  GACCAGCCAA TTACTAAACT TAAGAATTTA GAAGATGTTG TTGTCCCTAC
    251  TATGGAAATT AAGGTAATTT GCAATTAACT CTTGATTTTT TTTAAACTAA
    301  ATTTTTTTTA TTAGATTGAA CCATTTGAAA TAGTATTTTT ATGTAGGTCA
    351  AAATTGGTTA AATATTGGCA AATTTCATAT GTTTCAACCT ATAATTTCTC
    401   AGTATTATAT TTCCTTTGCC C
```

****************************************************************

Exon 57 (SEQ ID NO:56)

```
      1  ATATTAGTGA ATCTTTGATG AAACAGTAGT TAAACTTACG AGCGTGAGCC
     51  ACCACACCCG GCCTAAAGTT GTAGTTCTTA ACCACTATCA CATCGTCATT
    101  TGTTTCTCTG TTTAATATTA AAATTGCCAT TTATAATGTA TTGTGCTTTA
    151  AGTGCAAATA GTGTATCCGA CCTATTAGCA ATCATGTTTA TACTTTTATT
    201  AGGTGGACCA CACAGGAGAA TATGGAAATC TGGTGACTAT ACAGTCATTT
    251  AAAGCAGAAT TTCGCTTAGC AGGAGGTGTA AATTTACCAA AAATAATAGA
    301  TTGTGTAGGT TCCGATGGCA AGGAGAGGAG ACAGCTTGTT AAGGTGAGCC
    351  TTCCCTTCTC TGGCTTAGCC CTTAGAGTTT TAGTGATGAA AATTTTTAGT
    401   TCATATTTCT TTCTGCTTTA TTGGGGATTT GGGTCTTTAT TTGGGAATA
```

****************************************************************

Exon 58 (SEQ ID NO:57)

```
      1  GGGAAACTTT CTAAATCAGT GTAAATGTTG TAGCTTATTC TAAATGAAAG
     51  AATGGCAGTA GGTATTTAAT TATTTGGGAG ACTGTCAAGA GGTGCACAGA
    101  TGCTCAGATT GGTTTGAGTG CCCTTTGCTA TTCTCAGATG ACTCTGTGTT
    151  TTTATAATAA AATAAACTGT ACTTGTTTAT TCATGCTTAA TTATTCTGAA
    201  GGGCCGTGAT GACCTGAGAC AAGATGCTGT CATGCAACAG GTCTTCCAGA
    251  TGTGTAATAC ATTACTGCAG AGAAACACGG AAACTAGGAA GAGGAAATTA
    301  ACTATCTGTA CTTATAAGGT AACTATTTGT ACTTCTGTTA GTTCACCAAA
    351  AACATATAAA AGATGCCATT TGGTTGGGTG AAGTGGCTCA TGCCCATATT
    401  CATAATGCTT TGGGAGGCCA AGGTGGGAGG ATTGCTTGAG GCCAGGAGTT
    451  CGAGACCAGC CTCAGCAACA TAGTGAGACC CCATCTTGAC AAAAAGTTAA
    501  AAAAAAAAAA AAAACCAGAG
```

****************************************************************

Exon 59 (SEQ ID NO:58)

```
      1  TTCTTTGAGC TTAAGTTTAT TTCCGATTGG TTTCCTCCAA GGAGCTTTGT
     51  CTTCTATGGA CAGAGAAATA TTAATACAAC TTGAAAAAAA ATGCTTTGCA
```

TABLE 5-continued

GENOMIC ORGANIZATION
Each exon and its flanking intron sequences are listed
separately with the exon underlined. Exons are separated by a
row of ****. Example primers are in bold.

```
    101  CTGACTCTGA TAGCTGAATG ATCATCAAAT GCTCTTTAAT GGCCTTTTAA
    151  AAGTAAAAGG TATTTAATCT GTAACTCCAG GTGGTTCCCC TCTCTCAGCG
    201  AAGTGGTGTT CTTGAATGGT GCACAGGAAC TGTCCCCATT GGTGAATTTC
    251  TTGTTAACAA TGAAGATGGT GCTCATAAAA GATACAGGCC AAATGATTTC
    301  AGTGCCTTTC AGTGCCAAAA GAAAATGATG GTGAGTGACA CCCAAAATTA
    351  AAGGTTATTG TAAGATTATT TAATGGCTTA TTAAAGCTGA CAGCTGTCAG
    401  ATATTATAGA ATACAAAAAA ACTTTAATTT CATCAGGTAA TTGTCAAAGA
    451  TACTAAGTAA AAGAAAAACT CATCAGAATG AAAGTGTGTG AGTGAAAAAG
    501   GAAGGATTTT AAACTACAT
```

****************************************************************

Exon 60 (SEQ ID NO:59)

```
      1  ATCACTTGTA ATTAATTGCT TCCCTGTCCA GACTGTTAGC TTCTTGTAGG
     51  TAATGTATCC TGTTCATCTT TATTGCCCCT ATATCTGTCA TATTTTTATA
    101  TAAAAATGTG TATATTAGTT TAATTGAACA CAATATTGAA AAATAATTAT
    151  ATATATTCTC TATTTAAAGG AGGTGCAAAA AAAGTCTTTT GAAGAGAAAT
    201  ATGAAGTCTT CATGGATGTT TGCCAAAATT TTCAACCAGT TTTCCGTTAC
    251  TTCTGCATGG AAAAATTCTT GGATCCAGCT ATTTGGTTTG AGAAGCGATT
    301  GGCTTATACG CGCAGTGTAG CTACTTCTTC TATTGGTAAT CTTCTTGTAC
    351  ATATAGTAGA TTGAGCACTT TGTTGTTTGG CAGGTTTTAT TTTTGTTTGA
    401  TTCAGCACTT TTTCTACATT CTGAGTTGCA GGGGGATGAT AGTGATGATG
    451  TGGTTAGTAA CCATCCCATC TTCATTATTA AATCATATGT TTCTTGTTCA
    501  TCCTGATTCT TAGTGTCTAC CTTTTTATAA CTTATGCAGA AGAGAATTCT
```

****************************************************************

Exon 61 (SEQ ID NO:60)

```
      1  AATCATCTAG GATTTGTAAA ATGCAATATG CATTAAAATA GCTGGCAAGA
     51  TTTGAGTTAA ACTCaACATG GCCGGTTATG CACATCATTT AAGTAGGCTA
    101  AAAATCCTAA ACTACTTAAA GATTATACCA AGTCAGTGGT CTTAATTGAA
    151  ATTATGGCTA TATATTAGAA AGAGATGGAA TCAGTGATTT CAGATTGTTT
    201  GTTTCTTTTT TCTCCAGTTG GTTACATACT TGGACTTGGT GATAGACATG
    251  TACAGAATAT CTTGATAAAT GAGCAGTCAG CAGAACTTGT ACATATAGAT
    301  CTAGGTAAGT AATAAAATCT ATGTATCTAT TCTTTTTAGT AAATATTTGG
    351  TCATCATGGA ATGTTGTTTG CCTACCAAGA TATTACAAAT ATAAGAGACA
    401  GATAAATCGA AGCAGTAAAT ATTGGGTTTT TTTGTTTTCA GCATAAACAG
    451   TTGTCCTAGA AGAAACAGTT AACT
```

****************************************************************

Exon 62 (SEQ ID NO:61)

```
      1  GATTTGAGGT GGATCTCACA GACAGTGACA AAGATGAGGA AGGCAGCCAG
     51  AGCAGAAGTA AACTACTGTA CATACTAGTG TTCATAGAAC GTAGGTAACA
    101  TGTGGTTTCT TGCCTTTGTA AAGTTCACAT TCTAACTGGA AAGAAAGTAA
    151  ATTAGCTGTC AAACCTCCTA ACTTCACTGT ATTCTTTACT TTAGGTGTTG
    201  CTTTTGAACA GGGCAAAATC CTTCCTACTC CTGAGACAGT TCCTTTTAGA
    251  CTCACCAGAG ATATTGTGGA TGGCATGGGC ATTACGGGTG TTGAAGGTGT
    301  CTTCAGAAGG TAAGTGATAT GAAGTAAAGG AGGGAAATAA TTTTTGATGT
    351  CAAAATTACA TGGGCTGGGC ATGGTTCTTT GCACCTGTAA TCCCAGCTAC
    401  TCAAGAGGCT GAAGTGGGAG GATTGTTTGA GCCCAGGAGT TTGAGTCCAG
    451   CCTAGGCAAT ACAGCAAGAC CCTGTATCTA AAA
```

****************************************************************

Exon 63 (SEQ ID NO:62)

```
      1  TTCTTGTAAA TGCCAAGCTT GTGAAATAGT CAAATACATA TTTGTATTCA
     51  TTTCAAACGT CTAATGAAAG CCCACTCTGC CAAGTATTAT GCTATTTTGA
    101  GATACAGATA TGTAGATTAT TAAGCATAGG CTCAGCTAC TACACATGAG
    151  AGTATACAGA TAAAGATATG TTGACAACAT TGGTGTGTAA CAAAATCCGT
    201  ATTTATAATG TGTTTGACTC TAGATGCTGT GAGAAAACCA TGGAAGTGAT
    251  GAGAAACTCT CAGGAACTC TGTTAACCAT TGTAGAGGTA AAGTATTTTA
    301   TAAGGAAGAC TTTATTTT
```

****************************************************************

Exons 64–65 (SEQ ID NO:63)

```
      1  AAGAACAGAT GTTCTCTCTG TTTAGGTCCT TCTATATGAT CCACTCTTTG
     51  ACTGGACCAT GAATCCTTTG AAAGCTTTGT ATTTACAGCA GAGGCCGGAA
```

TABLE 5-continued

GENOMIC ORGANIZATION
Each exon and its flanking intron sequences are listed
separately with the exon underlined. Exons are separated by a
row of ****. Example primers are in bold.

```
101  GATGAAACTG AGCTTCACCC TACTCTGAAT GCAGATGACC AAGAATGCAA
151  ACGAAATCTC AGGTGAGCAG TATTTTAAGA AGGTCCTGTT GTCAGTATTT
201  CAGATTTTCT TATTCCCAAG GCCTTTAAAC TGGTCACCTG GACTGGAACC
251  TTTGTGTTTT TGTCCTTAGT GATATTGACC AGAGTTTCGA CAAAGTAGCT
301  GAACGTGTCT TAATGAGACT ACAAGAGAAA CTGAAAGGAG TGGAAGAAGG
351  CACTGTGCTC AGTGTTGGTG GACAGGTGAA TTTGCTCATA CAGCAGGCCA
401  TAGACCCCAA AAATCTCAGC CGACTTTTCC CAGGATGGAA AGCTTGGGTG
451  TGA (stop codon) Exon 65 continues beyond the TGA stop
     codon into the 3'UTR (SEQ ID NO:8)
```

****************************************************************

REFERENCES

Aicardi et al., "Ataxia-ocularmotor apraxia: A syndrome mimicking ataxia-telangiectasia" Ann. Neurol. 24:497–502 (1988).

Aksentijevitch et al., "Familial Mediterranean fever in Moroccan Jews: Demonstration of a founder effect by extended haplotype analysis" Am. J. Hum. Genet., 53:644–651 (1993).

Ambrose et al., "A physical map across chromosome 11q22-23 containing the major locus for ataxia-telangiectasia. Genomics, 21:612–619 (1994a).

Ambrose et al., 1994b. Structure and expression of the Huntington's disease gene: evidence against simple inactivation due to an expanded CAG repeat. Som. Cell Mol. Genet. 20:27–38.

Anderson and Kunkel, "The molecular and biochemical basis of Duchenne muscular dystrophy" Trends Biochem. Sci. 17:289–292 (1992).

Attree et al., "The Lowe's oculocerebrorenal syndrome gene encodes protein highly homologous to inositol polyphosphate-5-phosphatase" Nature, 358:239–242 (1992).

Ballabio et al., "Molecular heterogeneity of steroid sulfatase deficiency: a multicenter study on 57 unrelated patients, at DNA and protein levels" Genomics 4:36–40 (1989).

Barker, "A more robust, rapid alkaline denaturation sequencing method", BioTechniques, Vol. 14, No. 2, pp. 168–169 (1993).

Barnes, 1994. PCR amplification of up to 35-kb DNA with high fidelity and high yield from lambda bacteriophage templates. Proc. Natl. Acad. Sci. 91:2216–2220.

Berger et al., "Isolation of a candidate gene for Norrie disease by positional cloning" Nature Genet. 1:199–203, (1992).

Beaudet and Tsui, "A suggested nomenclature for designating mutations" Hum. Mutat. 2:245–248 (1993).

Broughton et al., "Mutations in the xeroderma pigmentosum group D DNA repair/transcription gene in patients with trichothiodystrophy" Nature Genet. 7:189–194 (1994).

Broughton et al., "Molecular and cellular analysis of the DNA repair defect in a patient in xeroderma pigmentosum group D who has the clinical features of xeroderma pigmentosum and Cockayne's syndrome" Am. J. Hum. Genet. 56:167–174 (1995).

Brown et al., "Control of p70 S6 kinase by kinase activity of FRAP in vivo" Nature 377:441–446 (1995).

Buckler et al., "Exon amplification: a strategy to isolate mammalian genes based on RNA splicing" Proc. Natl. Acad. Sci. USA, 88:4005–4009 (1991).

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251–270 (1991).

Byrne et al., "Ataxia-without-telangiectasia" J Neurol. Sci. 66:307–317 (1984).

Capecchi, "Altering the genome by homologous recombination" Science 244:1288–1292 (1989).

Chakravarti et al., "Nonuniform recombination within the human beta-globin gene cluster" Am. J. Hum. Genet., 36:1239–1258 (1984).

Chelly et al., "Isolation of a candidate gene for Menkes disease that encodes a potential heavy metal binding protein" Nature Genet. 3:14–19 (1993).

Cheng et al., 1994. Effective amplification of long targets from cloned inserts and human genomic DNA. Proc. Natl. Acad. Sci. 91:5695–5699.

Chessa et al., "Heterogeneity in ataxia telangiectasia: classical phenotype associated with intermediate cellular radiosensitivity" Am. J. Med. Genet. 42:741–746 (1992).

Chillon et al., "Mutations in the cystic fibrosis gene in patients with congenital absence of the vas deferens" New Engl. J. Med. 332:1475–1480 (1995).

Church et al., "Isolation of genes from complex sources of mammalian genomic DNA using exon amplification" Nature Genet. 6:98–104 (1993).

Church et al., 1994. Isolation of genes from complex sources of mammalian genomic DNA using exon amplification. Nature Genet. 6:98–94.

Collins, F. S. "Positional cloning: let's not call it reverse anymore" Nature Genet., 1:3–6 (1992).

Cooper and Krawczak, Human gene mutation. BIOS Scientific Publishers, London (1993).

Davies et al., "Targeted alterations in yeast artificial chromosomes for inter-species gene transfer", Nucleic Acids Research, Vol. 20, No. 11, pp. 2693–2698 (1992).

Derry et al., "WSP gene mutations in Wiskott-Aldrich syndrome and X-linked thrombocytopenia" Hum. Mol. Genet. 4:1127–1135 (1995).

Dickinson et al., "High frequency gene targeting using insertional vectors", Human Molecular Genetics, Vol. 2, No. 8, pp. 1299–1302 (1993).

Dietz and Kendzior, "Maintenance of an open reading frame as an additional level of scrutiny during splice site selection" Nature Genet. 8:183–188 (1994).

Duyk et al., "Exon trapping: A genetic screen to identify candidate transcribed sequences in cloned mammalian genomic DNA" Proc. Natl. Acad. Sci. USA, 87:8995–8999 (1990).

Fiorilli et al., "Variant of ataxia-telangiectasia with low-level radiosensitivity" *Hum. Genet.* 70:274–277 (1985).

Fodor et al, "Multiplexed biochemical assays with biological chips", *Nature* 364:555–556 (1993).

Foord and Rose, 1994. Long-distance PCR. PCR Methods Appl. 3:S149–S161.

Foroud et al. "Localization of the AT locus to an 8 cM interval defined by STMY and S132" *Am. J. Hum. Genet.,* 49:1263–1279 (1991).

Friedman and Weitberg, "Ataxia without telangiectasia" *Movement Disorders* 8:223–226 (1993).

Frohman, M. A. "On beyond classic RACE (rapid amplification of cDNA ends)" *PCR Methods and Applications,* 4:S40–S58 (1994).

Frohman et al., "Rapid production of full-length cDNAs from rare transcripts: Amplification using a single gene-specific oligonucleotide primer" *Proc. Natl. Acad. Sci. USA,* 85:8998–9002 (1988).

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization of an ataxia-telangiectasia gene to chromosome 11q22-23" *Nature,* 336: 577–580 (1988).

Gibson et al., "A nonsense mutation and exon skipping in the Fanconi anaemia group C gene" *Hum. Mol. Genet.* 2:797–799 (1993).

Gilboa et al. "Transfer and expression of cloned genes using retroviral vectors" *BioTechniques* 4(6):504–512 (1986).

Gottlieb and Jackson, "Protein kinases and DNA damage" *Trends Biochem. Sci.* 19:500–503 (1994).

Greenwell et al., "TEL1, a gene involved in controlling telomere length in *Saccharomyces cerevisiae,* is homologous to the human ataxia telangiectasia (ATM) gene" Cell 82:823–829 (1995).

Hastbacka et al., "Linkage disequilibrium mapping in isolated founder populations: diastrophic dysplasia in Finland" *Nature Genet.,* 2:204–211 (1992).

Harding, "Clinical features and classification of inherited ataxias" *Adv. Neurol.* 61:1–14 (1993).

Harnden, "The nature of ataxia-telangiectasia: problems and perspectives" *Int. J. Radiat. Biol.* 66:S13–S19 (1994).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics,* 9:742–750 (1991).

Jackson, 1991. A reappraisal of non-consensus mRNA splice sites. Nucleic Acids Res. 19:3795–3798.

Jakobovits et al., "Germ-line transmission and expression of a human-derived yeast artificial chromosome", *Nature,* Vol. 362, pp. 255–261 (1993).

James et al., "A radiation hybrid map of 506 STS markers spanning human chromosome 11", *Nature Genet.* 8:70 (1994).

Jarvi et al., Cystic fibrosis transmembrane conductance regulator and obstructive azoospermia" *The Lancet* 345:1578 (1995).

Jaspers et al., "Genetic complementation analysis of Ataxia-Telangiectasia and Nijmegen breakage syndrome: A survey of 50 patients", *Cytogenet. Cell Genet.,* 49:259 (1988).

Kawasaki, E. S. Amplification of RNA. In: PCR protocols: A Guide to Methods and Applications, Innis, M. A., Gelfand, D. H., Sninsky, J. J., White, T. J., eds. Academic Press, 1990, pp21–27.

Kerem et al., "Identification of the cystic fibrosis gene: genetic analysis" *Science,* 245:1073–1080 (1989).

Kolluri et al., "Identification of WASP mutations in patients with Wiskott-Aldrich syndrome and isolated thrombocytopenia reveals allelic heterogeneity at the WAS locus" *Hum. Mol. Genet.* 4:1119–1126 (1995).

Lamb et al., "Introduction and expression of the 400 kilobase precursor amyloid protein gene in transgenic mice", *Nature Genetics,* Vol. 5, pp. 22–29 (1993).

Lange et al., "Localization of an ataxia-telangiectasia gene to a 850 kb interval on chromosome 11q23.1 by linkage analysis of 176 families in an international consortium" *Am. J. Hum. Genet.* (1995).

Lehesjoki et al., "Localization of the EPM1 gene for progressive myoclonus epilepsy on chromosome 21: linkage disequilibrium allows high resolution mapping" *Hum. Mol. Genet.,* 2:1229–1234 (1993).

Lichter et al., "High-resolution mapping of human chromosome 11 by in situ hybridization with cosmid clones" *Science* 247:64–69 (1990).

Litt and Luty, "A hypervariable microsatellite revealed by in vitro amplification of a dinucleotide repeat within the cardiac muscle actin gene" *Am. J. Hum. Genet.,* 44:397–401 (1989).

Liu and Sommer, "Restriction endonuclease fingerprinting (REF): a sensitive method for screening mutations in long, contiguous segments of DNA" *BioTechniques* 18:470–477 (1995).

Llerena et al., "Spontaneous and induced chromosome breakage in chorionic villus samples: a cytogenetic approach to first trimester prenatal diagnosis of ataxia-telangiectasia syndrome" *J. Med. Genet.,* 26:174–178 (1989).

Lovett et al., "Direct selection: A method for the isolation of cDNA encoded by large genomic regions", *Proc. Natl. Acad. Sci. USA* 88, 9628 (1991).

Maserati et al., "Ataxia-without-telangiectasia in two sisters with rearrangements of chromosomes 7 and 14" *Clin. Genet.* 34:283–287 (1988).

McConville et al., "Genetic and physical mapping of the ataxia-telangiectasia locus on chromosome 11q22-23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22-23" *Hum. Mol. Genet.,* 2:969–974 (1993).

McConville et al., "Fine mapping of the chromosome 11q22-23 region using PFGE, linkage and haplotype analysis; localization of the gene for ataxia telangiectasia to a 5 cM region flanked by NCAM/DRD2 and STMY/CJ52.75, phi2.22" *Nucleic Acids Res.,* 18:4335–4343 (1990).

Miki et al. "A strong candidate for the breast and ovarian cancer susceptibility gene BRCA1" *Science,* 266:66–71 (1994).

Mitchison et al., "Fine genetic mapping of the Batten Disease locus (CLN3) by haplotype analysis and demonstration of allelic association with chromosome 16p microsatellite loci" *Genomics,* 16:455–460 (1993).

Morgan et al., "The selective isolation of novel cDNAs encoded by the regions surrounding the human interleukin 4 and 5 genes" *Nucleic Acids Res.,* 20:5173–5179 (1992).

Nehls et al., 1994a. Exon amplification from complete libraries of genomic DNA using a novel phage vector with automatic plasmid excision facility: application to the mouse neurofibromatosis-1 locus. Oncogene 9:2169–2175.

Nehls et al., 1994b. The sequence complexity of exons trapped from the mouse genome. Current Biology 4:983–989.

Orita et al. Detection of polymorphisms of human DNA by gel electrophoresis as single-strand conformation polymorphisms. Proc Natl Acad Sci USA 1989; 86:2766–2770.

Oskato et al., "Ataxia-telangiectasia: allelic association with 11q22-23 markers in Moroccan-Jewish patients. 43rd Annual Meeting of the American Society of Human Genetics, New Orleans, La. (1993).

Ozelius et al., "Strong alleleic association between the torsion dystonia gene (DYT1) and loci on chromosome 9q34 in Ashkenazi Jews" Am. J. Hum. Genet. 50:619–628 (1992).

Parimoo et al., "cDNA selection: Efficient PCR approach for the selection of cDNAs encoded in large chromosomal DNA fragments" Proc. Natl. Acad. Sci. USA, 88:9623–9627 (1991).

Pease et al., "Light-generated oligonucleotide arrays for rapid DNA sequence analysis", Proc. Natl. Acad. Sci. USA 91(11):5022–5026 (1994).

Richard et al., "A radiation hybrid map of human chromosome 11q22-23 containing the Ataxia-Telangiectasia disease locus", Genomics 17, 1 (1993).

Roberts et al., 1993. Exon structure of the human dystrophin gene. Genomics 16:536–538.

Rothstein, "Targeting, disruption, replacement, and allele rescue: integrative DNA transformation in yeast" in Methods in Enzymology, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" Human Molecular Genetics (1994b).

Rotman et al., "A YAC contig spanning the ataxia-telangiectasia locus (groups A and C) on chromosome 11q22-23. Genomics (1994c).

Rotman et al., "Physical and genetic mapping of the ATA/ATC locus in chromosome 11q22-23" Int. J. Radiat. Biol. (1994d).

Rotman et al., "Rapid identification of polymorphic CA-repeats in YAC clones" Molecular Biotechnology (1995).

Savitsky et al., "A single gene with homologies to phosphatidylinositol 3-kinases and rad3+ is Mutated in all complementation groups of ataxia-telangiectasia" Science, 268:1749–1753 (June 23, 1995a).

Savitsky et al., "The complete sequence of the coding region of the ATM gene reveals similarity to cell cycle regulators in different species" Hum. Mol. Genet. 4:2025–2032 (1995b).

Schedl et al., "A yeast artificial chromosome covering the tyrosinase gene confers copy number-dependent expression in transgenic mice", Nature, Vol. 362, pp. 258–261 (1993).

Sirugo et al., "Friedreich ataxia in Louisiana Acadians: Demonstration of a founder effect by analysis of microsatellite-generated extended haplotypes" Am. J. Hum. Genet., 50:559–566 (1992).

Shiloh, "Ataxia-telangiectasia: closer to unraveling the mystery" European Journal of Human Genetics (1995) Shiloh et al., Am. J. Hum. Genet. 55 (suppl.), A49 (1994a).

Shiloh, et al., 1994b. Genetic, physical and functional analysis of the ataxia-telangiectasia locus on chromosome 11q22-23. 44th Annual Meeting of the American Society of Human Genetics, Montreal. Am. J. Hum. Genet. 55:A49.

Sommer, "Recent human germ-line mutation: Inferences from patients with hemophilia B" Trends Gene. 11:141–147 (1995).

Steingrimsdottir et al., "Mutations which alter splicing in the human hypoxanthine-guanine phosphoribosyl-transferase gene" Nucleic Acids Res. 6:1201–1208 (1992).

Strauss et al., "Germ line transmission of a yeast artificial chromosome spanning the murine $\alpha_1$ (I) collagen locus", Science, Vol. 259, pp. 1904–1907 (1993).

Tagle et al., "Magnetic capture of expressed sequences encoded within large genomic segments" Nature, 361:751–753 (1993).

Taylor et al., "Genetic and cellular features of ataxia telangiectasia" Int. J. Radiat. Biol. 65:65–70 (1994).

Taylor et al., Variant forms of ataxia telangiectasia. J. Med. Genet. 24, 669–677 (1987).

The European Polycystic Kidney Disease Consortium, "The polycystic kidney disease 1 gene encodes a 14 kb transcript and lies within a duplicated region on chromosome 16" Cell, 77:881–894 (1994).

The Huntington's Disease Collaborative Research Group, "A novel gene containing a trinucleotide repeat that is expanded and unstable on Huntington's disease chromosomes" Cell, 72:971–983 (1993).

Trofatter et al., "A novel moesin-, ezrin-, radixin-like gene is a candidate for the neurofibromatosis 2 tumor suppressor" Cell, 72:791–800 (1993).

Vanagaite et al., "Physical localization of microsatellite markers at the ataxia-telangiectasia locus at 11q22-23. Genomics, 22:231–233 (1994a).

Vanagaite et al., "High-density microsatellite map of ataxia-telangiectasia locus" Human Genetics 95:451–453 (1995).

Vetrie et al., "The gene involved in X-linked agammaglobulinemia is a member of the src family of protein-tyrosine kinases" Nature, 361:226–233 (1993).

Weber and May, "Abundant class of human DNA polymorphisms which can be typed using the polymerase chain reaction" Am. J. Hum. Genet., 44:388–396 (1989).

Weemaes et al., "Nijmegen breakage syndrome: A progress report" Int. J. Radiat. Biol. 66:S185–S188 (1994).

Ying and Decoteau, "Cytogenetic anomalies in a patient with ataxia, immune deficiency, and high alpha-fetoprotein in the absence of telangiectasia" Cancer Genet. Cytogenet. 4:311–317 (1983).

Zakian, "ATM-related genes: What do they tell us about functions of the human gene?" Cell 82:685–687 (1995).

Ziv et al., "Ataxia-telangiectasia: linkage analysis in highly inbred Arab and Druze families and differentiation from an ataxia-microcephaly-cataract syndrome" Hum. Genet., 88:619–626 (1992).

Ziv et al., "The ATC (ataxia-telangiectasia complementation group C) locus localizes to 11q22-q23. Genomics, 9:373–375 (1991).

Ziv et al., "Ataxia telangiectasia: a variant with altered in vitro phenotype of fibroblast cells" Mutation Res. 210:211–219 (1989).

I claim:

1. A mutated form of the nucleic acid sequence in SEQ ID No:11 wherein a mutation event selected from the group consisting of point mutations, deletions, insertions and rearrangements has occurred such that the resulting sequence is altered to produce a truncated protein or no protein initiation occurs and thereby ataxia-telangiectasia.

2. The mutated nucleic acid sequence of claim 1 wherein the mutation events are those set forth in Table 3.

3. The mutated nucleic acid sequence of claim 1 wherein a mutation event selected from the group consisting of point mutations, deletions and insertions has occurred such that the encoded amino acid sequence is truncated to produce ataxia-telangiectasia.

4. The mutated nucleic acid sequence of claim 1 wherein a mutation event selected from the group consisting of point mutations, deletions, insertions and rearrangements has occurred within the regulatory sequences of ATM such that regulation of ATM is altered to produce a truncated protein or that no initiation of protein synthesis occurs and thereby ataxia-telangiectasia is produced.

5. A method of screening subjects exhibiting a partial A-T phenotype for ATM mutant genes for genetic counseling including the steps of:

(a) assaying a nucleic acid specimen from a subject exhibiting partial A-T phenotype for mutations of the ATM gene wherein the mutated nucleic acid sequence of claim 1 with mutations is identified by restriction endonuclease fingerprinting and (b) offering genetic counseling to subjects identified in step a to have a mutation of the ATM gene.

* * * * *